US006761737B2

(12) United States Patent
Zadno-Azizi et al.

(10) Patent No.: US 6,761,737 B2
(45) Date of Patent: Jul. 13, 2004

(54) TRANSLATION MEMBER FOR INTRAOCULAR LENS SYSTEM

(75) Inventors: Gholam-Reza Zadno-Azizi, Fremont, CA (US); Tuan Anh Nguyen, Orange, CA (US); Valdemar Portney, Tustin, CA (US); Albert C. Ting, Laguna Niguel, CA (US)

(73) Assignee: Visiogen, Inc., Irvine, CA (US)

( * ) Notice: Subject to any disclaimer, the term of this patent is extended or adjusted under 35 U.S.C. 154(b) by 0 days.

(21) Appl. No.: 10/017,915

(22) Filed: Dec. 11, 2001

(65) Prior Publication Data

US 2002/0116059 A1 Aug. 22, 2002

Related U.S. Application Data

(60) Provisional application No. 60/337,343, filed on Nov. 9, 2001, provisional application No. 60/283,856, filed on Apr. 13, 2001, and provisional application No. 60/264,179, filed on Jan. 25, 2001.

(51) Int. Cl.[7] .................................................. A61F 2/14
(52) U.S. Cl. ...................................................... 623/6.37
(58) Field of Search .............................. 623/4.1, 6.11, 623/6.22, 6.24, 6.34, 6.37

(56) References Cited

U.S. PATENT DOCUMENTS

| 4,409,691 A | 10/1983 | Levy |
| 4,666,445 A | 5/1987 | Tillay |
| 4,790,847 A | 12/1988 | Woods |
| 4,842,601 A | 6/1989 | Smith |
| 4,888,012 A | 12/1989 | Horn et al. |
| 4,892,543 A | 1/1990 | Turley |
| 4,963,148 A | 10/1990 | Sulc et al. |
| 4,994,082 A | 2/1991 | Richards et al. |
| 5,275,623 A | 1/1994 | Sarfarazi |
| 5,354,335 A | 10/1994 | Lipshitz et al. |

(List continued on next page.)

FOREIGN PATENT DOCUMENTS

| DE | 195 01 444 A1 | 1/1995 | |
| EP | 0 337 390 A2 | 11/1989 | |
| EP | 0 336 877 B1 | 10/1993 | |
| FR | 2 784 575 | 10/1998 | |
| JP | 02-126847 | * 5/1990 | ............. A61F/2/16 |
| WO | WO 99/20206 | 10/1998 | |
| WO | WO 99/03427 | 1/1999 | |
| WO | WO 00/27315 A1 | 5/2000 | |
| WO | WO 00/61036 | 10/2000 | |
| WO | WO 01/34067 A1 | 10/2000 | |
| WO | WO 00/66037 | 11/2000 | |

OTHER PUBLICATIONS

"Accommodative Intraocular Lens with Spring Action Part 1. Design and Placement in an Excised Animal Eye," Opthalmic Surgery, Feb. 1990, vol. 21, No. 2.
U.S. patent application Ser. No. 10/207,708, filed Jul. 25, 2002.
U.S. patent application Ser. No. 10/207,716, filed Jul. 25, 2002.
U.S. patent application Ser. No. 10/207,701, filed Jul. 25, 2002.

(List continued on next page.)

*Primary Examiner*—David H. Willse
*Assistant Examiner*—William H. Matthews
(74) *Attorney, Agent, or Firm*—Knobbe Martens Olson & Bear, LLP

(57) ABSTRACT

There is disclosed an accommodating intraocular lens for implantation in an eye having an optical axis. The lens comprises an anterior portion which in turn comprises an anterior viewing element and an anterior biasing element. The lens further comprises a posterior portion which in turn comprises a posterior viewing element in spaced relationship to the anterior viewing element and a posterior biasing element. The anterior portion and posterior portion meet at first and second apices of the intraocular lens. The anterior portion and the posterior portion and/or the apices are responsive to force thereon to cause the separation between the viewing elements to change. Additional embodiments and methods are also disclosed.

49 Claims, 47 Drawing Sheets

U.S. PATENT DOCUMENTS

| | | |
|---|---|---|
| 5,476,514 A | 12/1995 | Cumming |
| 5,496,366 A | 3/1996 | Cumming |
| 5,578,081 A | 11/1996 | McDonald |
| 5,674,282 A | 10/1997 | Cumming |
| 5,968,094 A | 10/1999 | Werblin et al. |
| 6,013,101 A | 1/2000 | Israel |
| 6,176,878 B1 | 1/2001 | Gwon et al. |
| 6,197,058 B1 | 3/2001 | Portney |
| 6,197,059 B1 | 3/2001 | Cumming |
| 6,217,612 B1 | 4/2001 | Woods |
| 6,231,603 B1 | 5/2001 | Lang et al. |
| 6,423,094 B1 | 7/2002 | Sarfarazi |
| 6,464,725 B2 | 10/2002 | Skotton |
| 6,488,708 B2 | 12/2002 | Sarfarazi |
| 6,503,276 B2 | 1/2003 | Lang et al. |
| 6,524,350 B2 | 2/2003 | Israel |
| 6,558,420 B2 | 5/2003 | Green |
| 2002/0002404 A1 | 1/2002 | Sarfarazi |
| 2002/0138140 A1 | 9/2002 | Hanna |
| 2002/0193876 A1 | 12/2002 | Lang et al. |
| 2003/0018384 A1 | 1/2003 | Valyunin et al. |
| 2003/0109926 A1 | 6/2003 | Portney |

OTHER PUBLICATIONS

U.S. patent application Ser. No. 10/207,688, filed Jul. 25, 2002.
U.S. patent application Ser. No. 10/207,717, filed Jul. 25, 2002.
U.S. patent application Ser. No. 10/016,705, filed Dec. 11, 2001.
U.S. patent application Ser. No. 10/017,753, filed Dec. 11, 2001.
U.S. patent application Ser. No. 10/017,916, filed Dec. 11, 2001.
U.S. patent application Ser. No. 10/017,920, filed Dec. 11, 2001.
U.S. patent application Ser. No. 10/020,002, filed Dec. 11, 2001.
U.S. patent application Ser. No. 10/020,853, filed Dec. 11, 2001.
U.S. patent application Ser. No. 10/020,858, filed Dec. 11, 2001.
U.S. patent application Ser. No. 10/021,795, filed Dec. 11, 2001.
U.S. patent application Ser. No. 10/021,797, filed Dec. 11, 2001.
U.S. patent application Ser. No. 10/207,688, filed Jul. 25, 2002.
U.S. patent application Ser. No. 10/207,701, filed Jul. 25, 2002.
U.S. patent application Ser. No. 10/207,708, filed Jul. 25, 2002.
U.S. patent application Ser. No. 10/207,717, filed Jul. 25, 2002.
U.S. patent application Ser. No. 10/207,718, filed Jul. 25, 2002.
U.S. patent application Ser. No. 10/635,423, filed Aug. 6, 2003, Valdemar Portney et al.

* cited by examiner

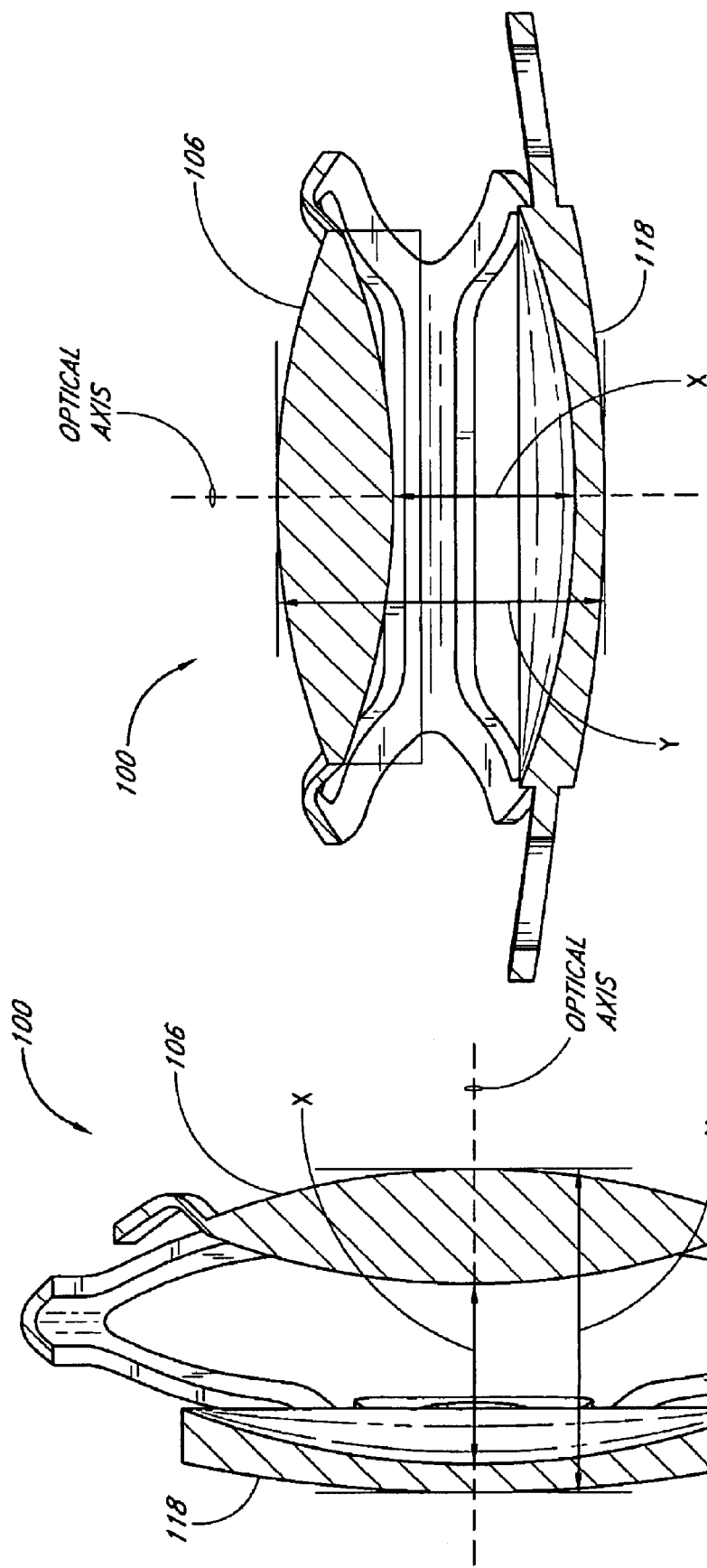

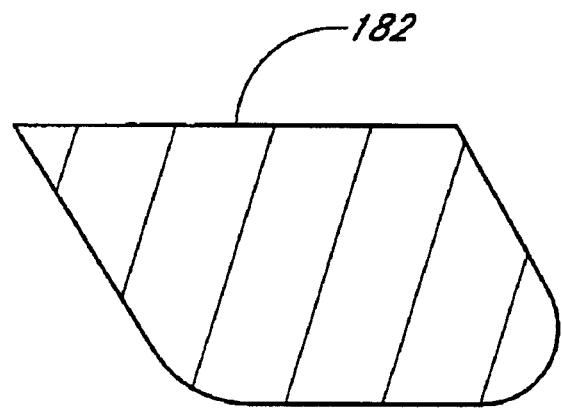
FIG. 17.1
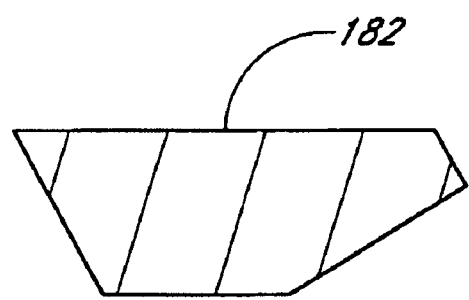
FIG. 17.2

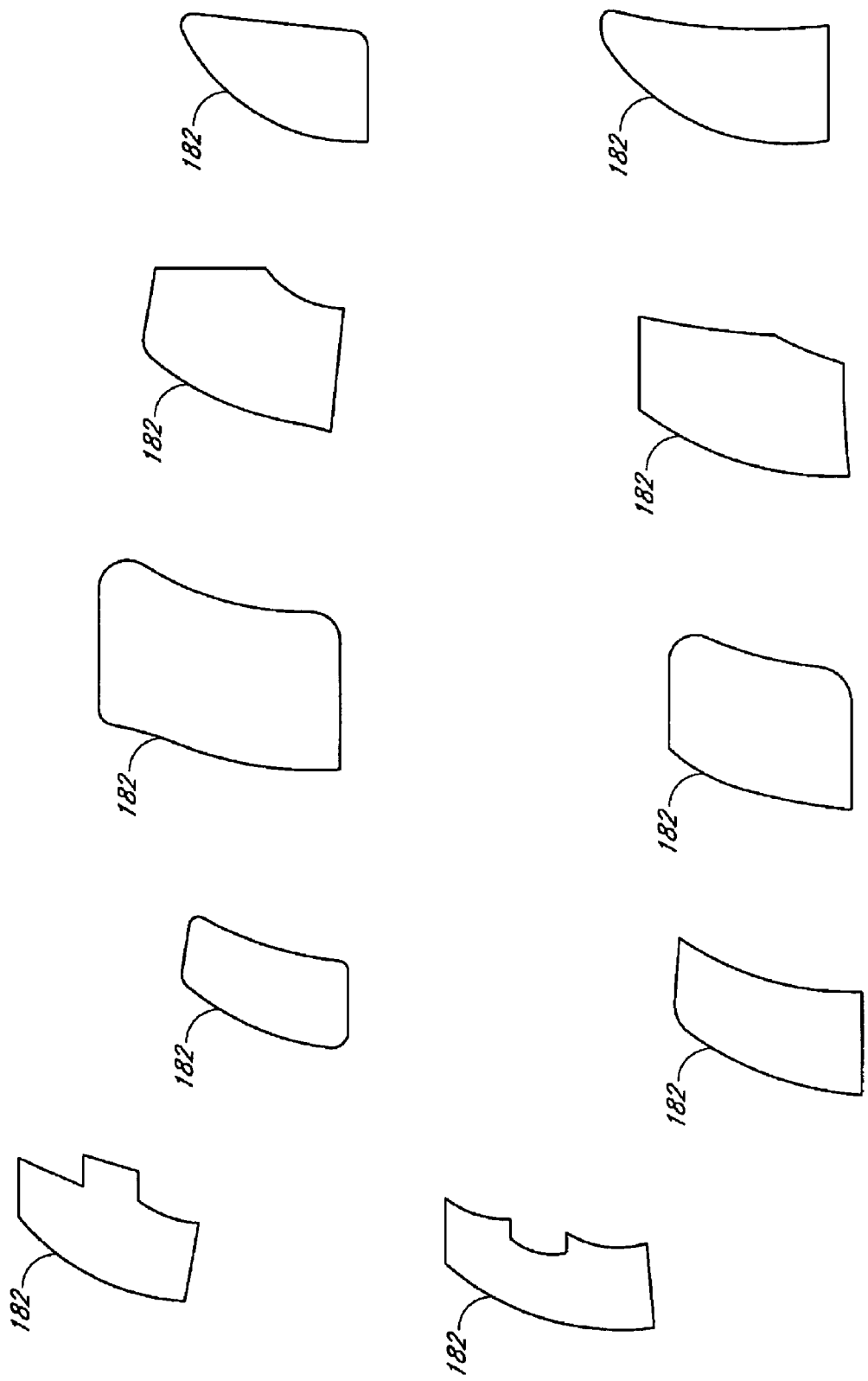
FIG. 17.3

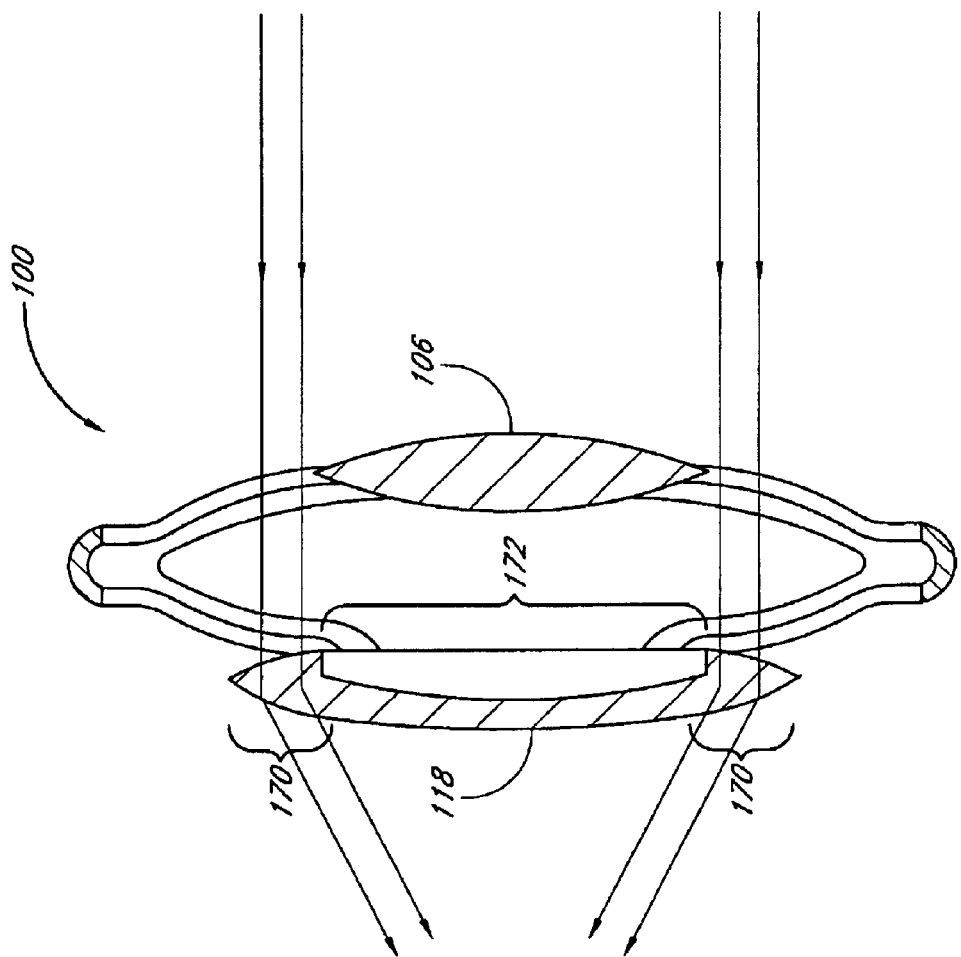
FIG. 17.4

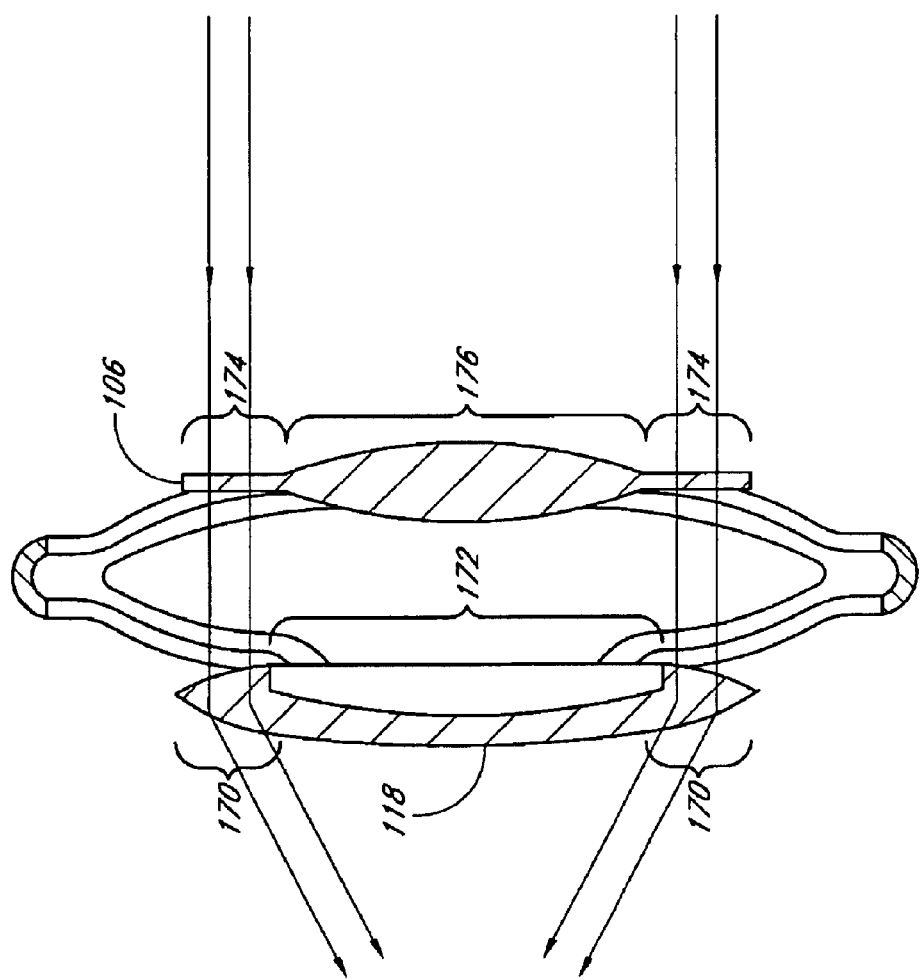
FIG. 17.5

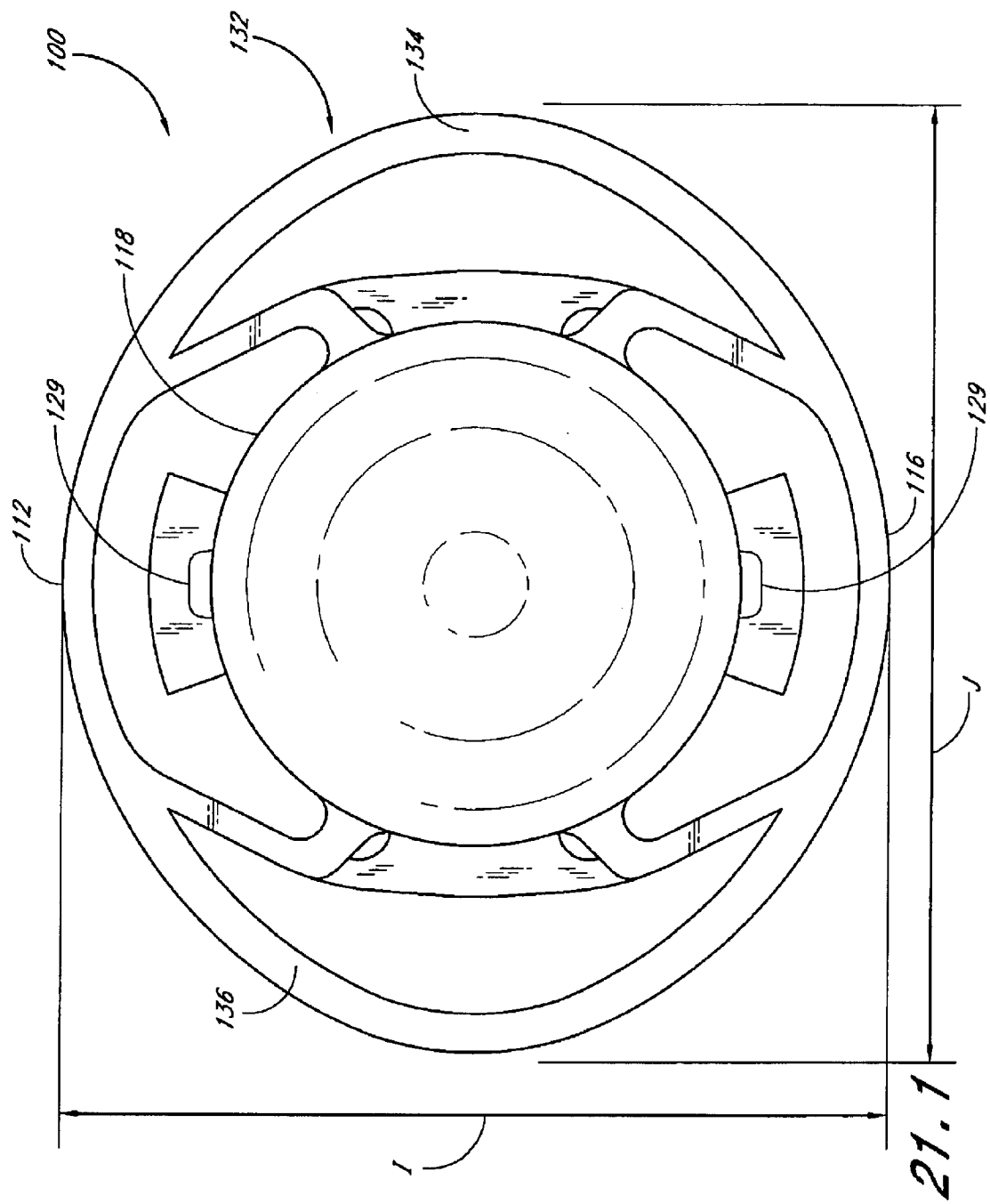
FIG. 21.1

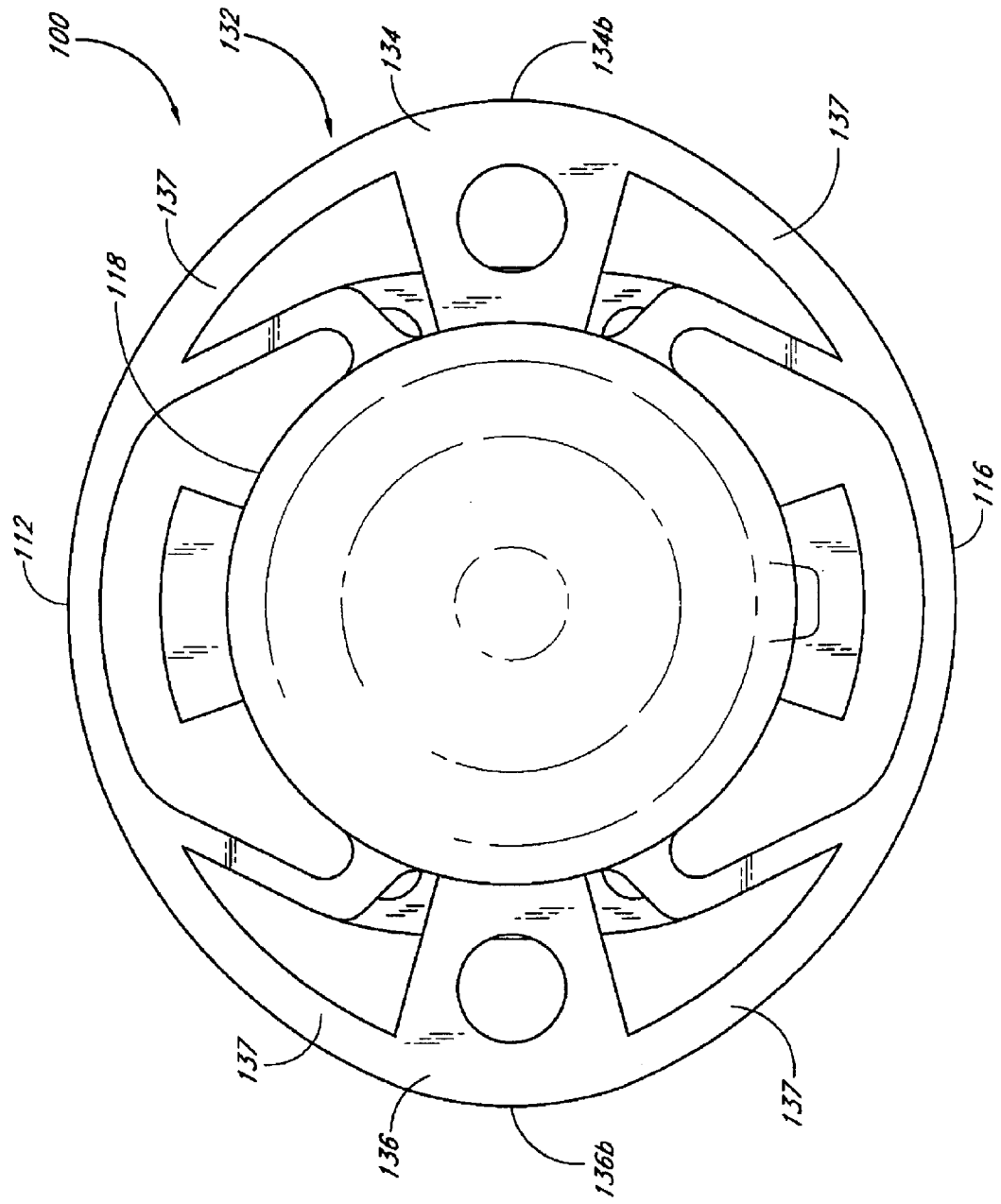
FIG. 21.2

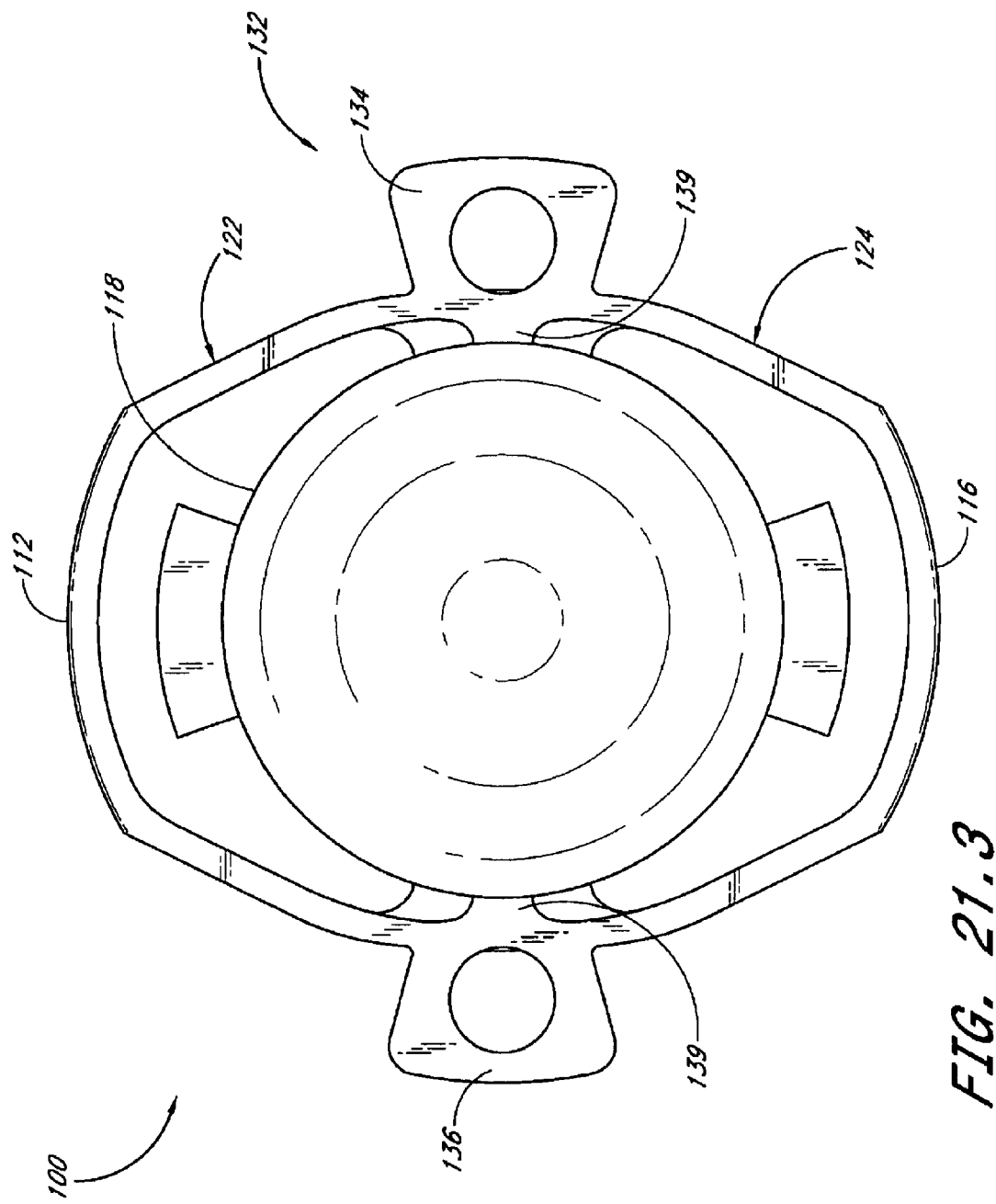
FIG. 21.3

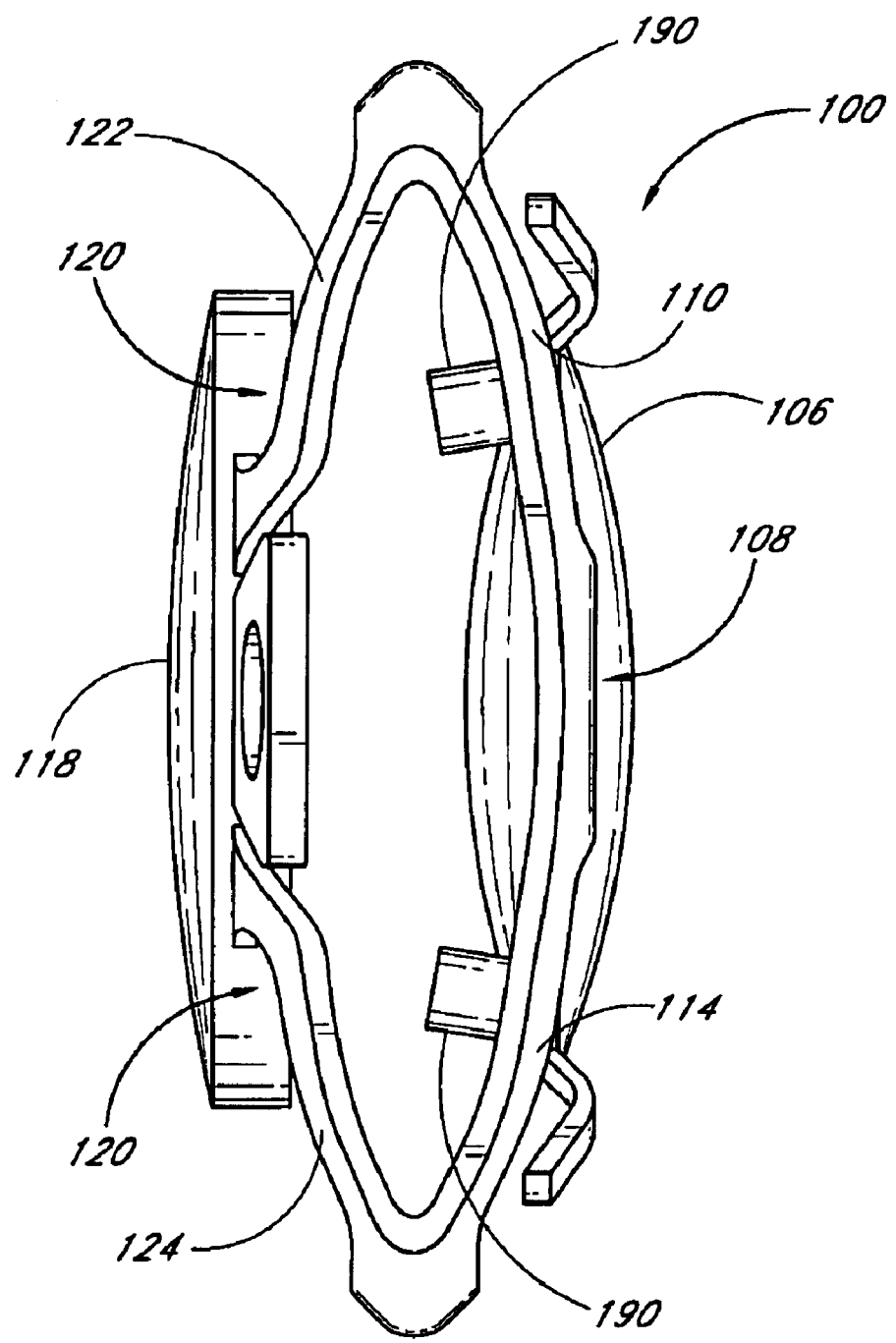
FIG. 22.1

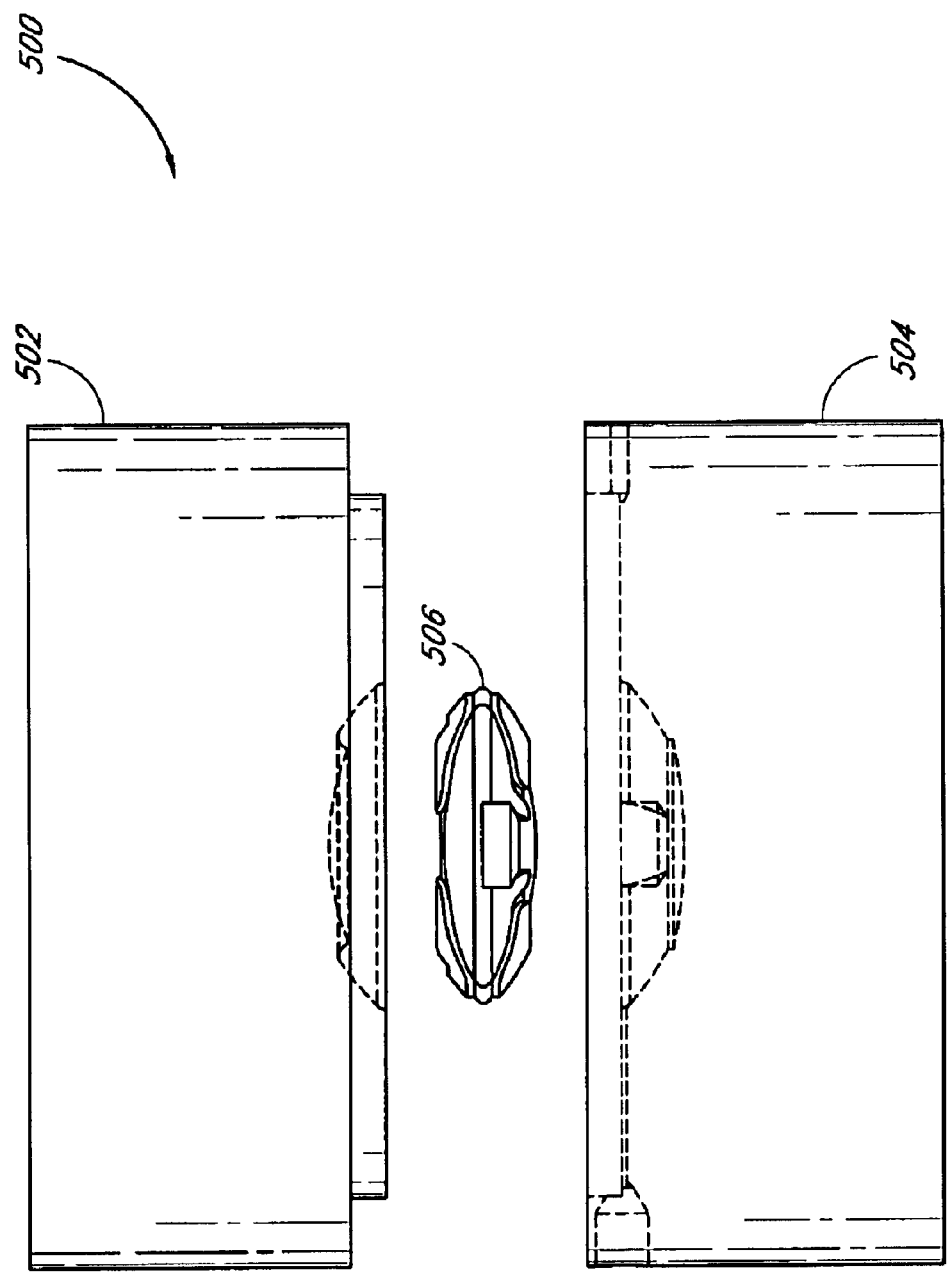

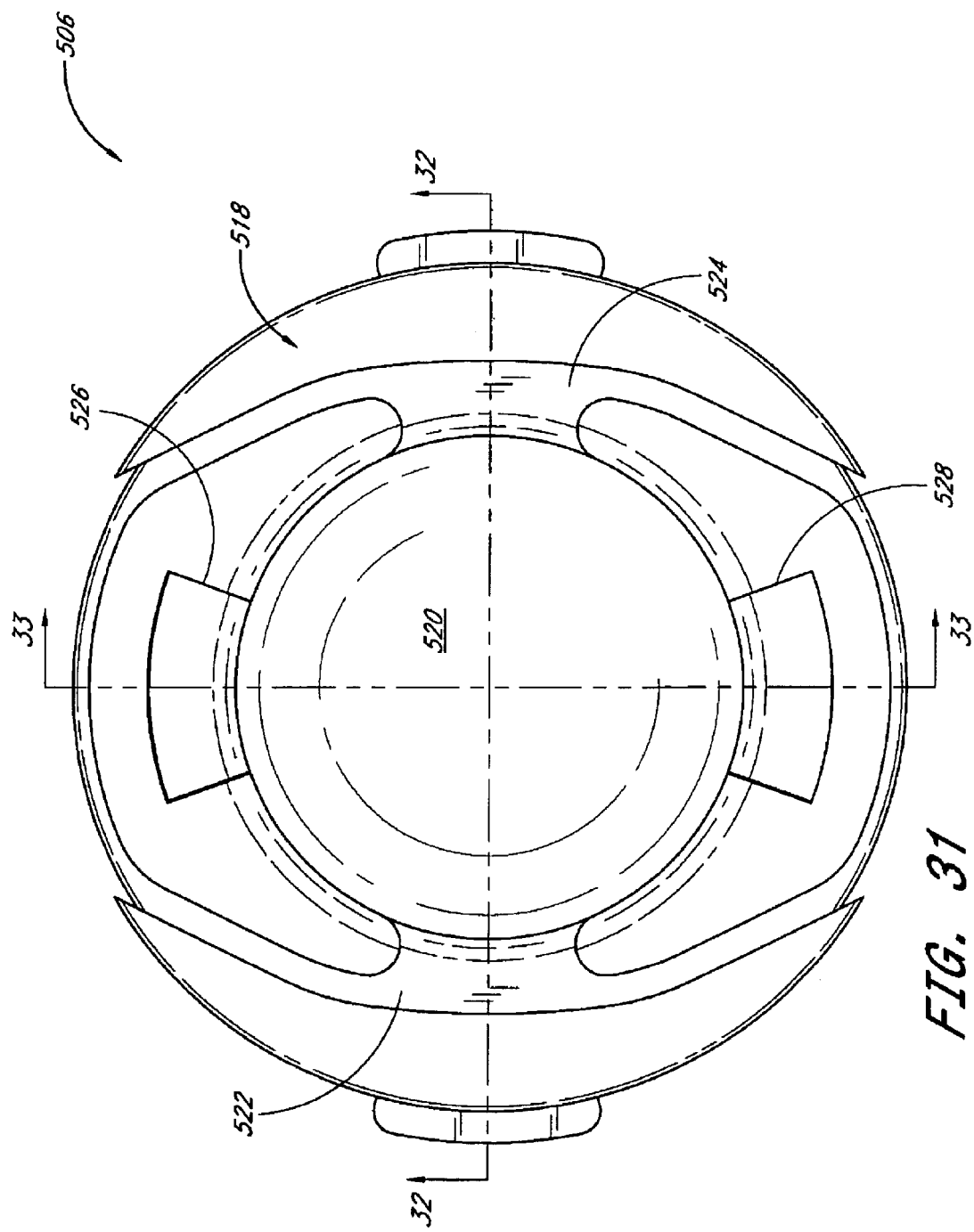

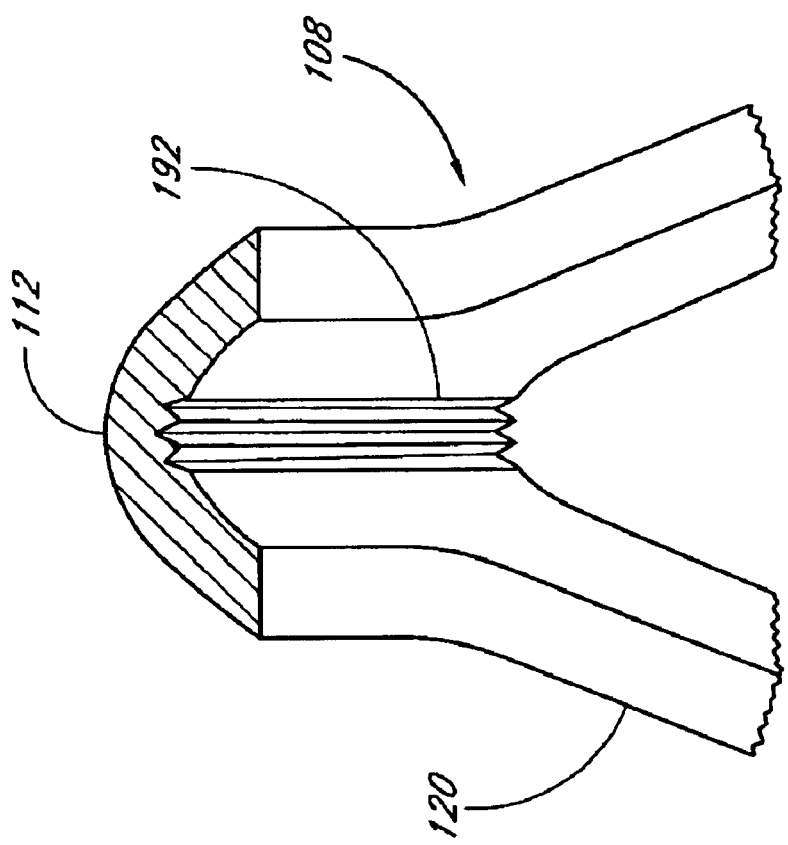
FIG. 34.1

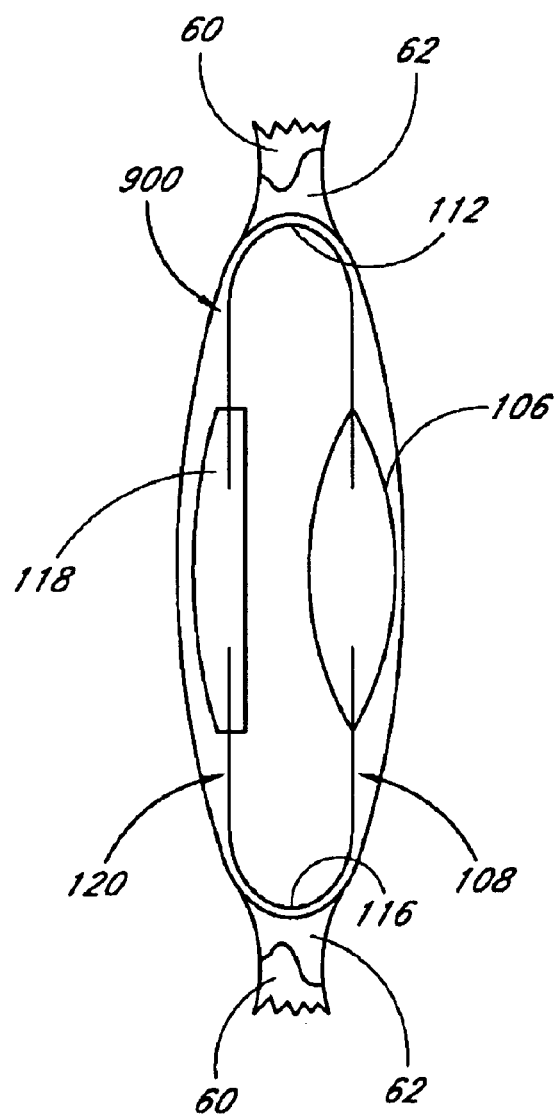
FIG. 38.1

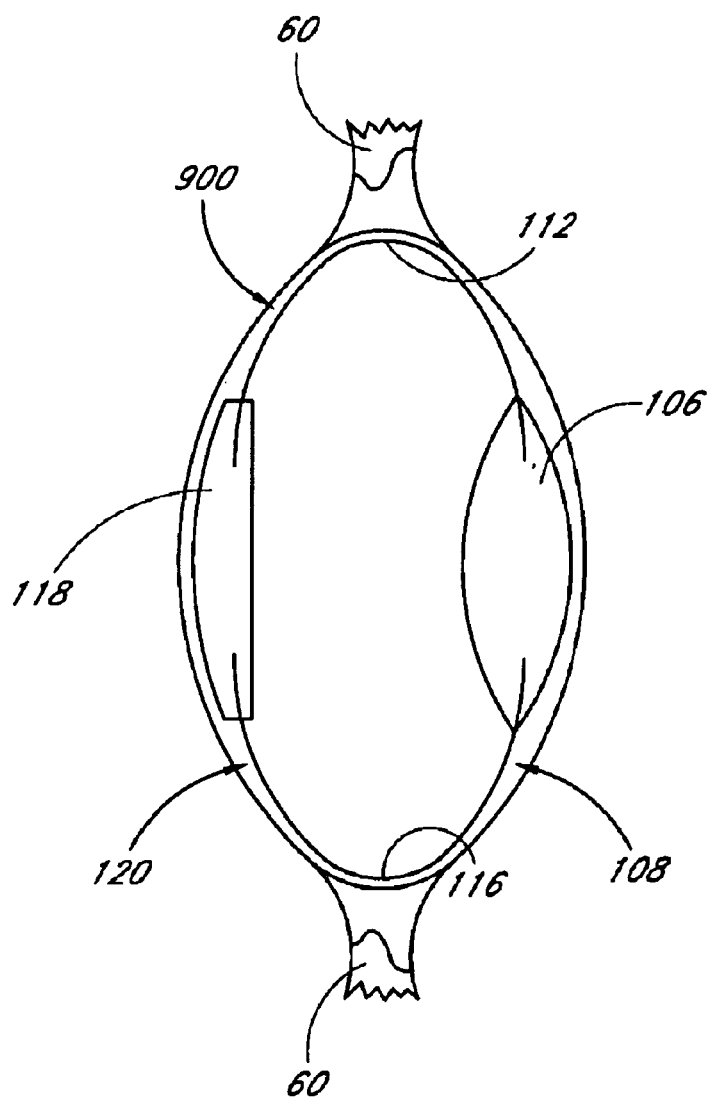
FIG. 38.2

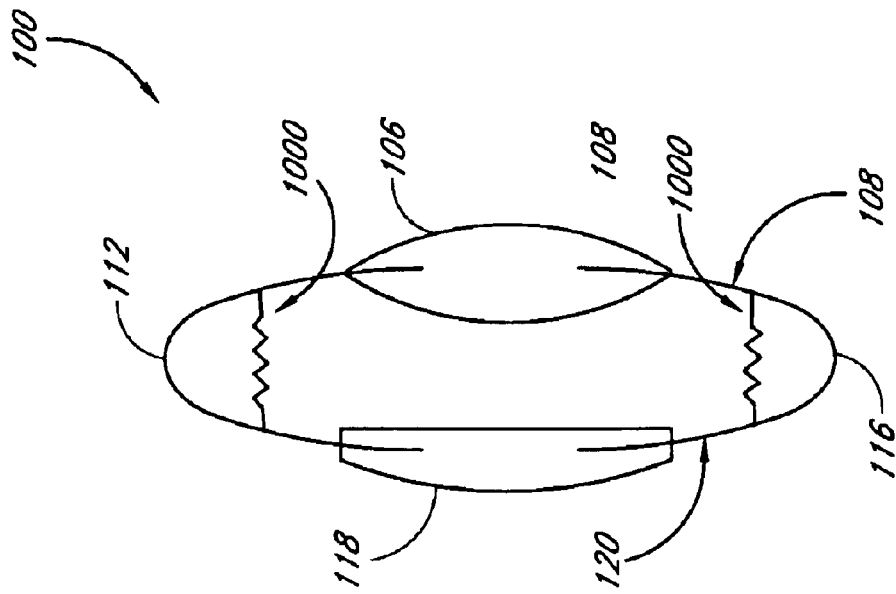
FIG. 38.4
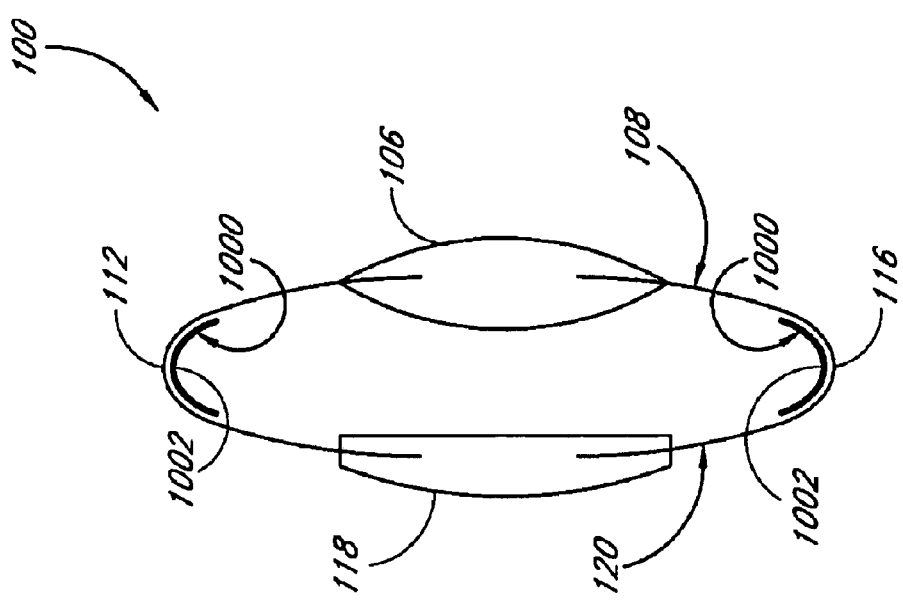
FIG. 38.3

TRANSLATION MEMBER FOR INTRAOCULAR LENS SYSTEM

RELATED APPLICATIONS

The present application claims the benefit of U.S. Provisional Patent Application No. 60/337,343, filed Nov. 9, 2001 and titled ACCOMMODATING INTRAOCULAR LENS SYSTEM; and of U.S. Provisional Patent Application No. 60/264,179, filed Jan. 25, 2001 and titled ACCOMMODATING INTRAOCULAR LENS SYSTEM; and of U.S. Provisional Patent Application No. 60/283,856, filed Apr. 13, 2001 and titled ACCOMMODATING INTRAOCULAR LENS SYSTEM. The entire disclosure of all these provisional patent applications is incorporated by reference herein and made a part of this specification.

BACKGROUND OF THE INVENTION

1. Field of the Invention

This invention relates to intraocular lenses and, more particularly, to intraocular lenses that alter the refractive power of the eye in response to changes in the tension of the ciliary muscle of the eye.

2. Description of the Related Art

The vast majority of cataract operations involve the implantation of an artificial lens following cataract removal. Typically these lenses have a fixed focal length or, in the case of bifocal or multifocal lenses, have several different fixed focal lengths. Such fixed focal-length lenses lack the ability of the natural lens to dynamically change the refractive power of the eye. The various embodiments of the intraocular lens disclosed herein provide an accommodating lens system which alters the refractive power of the eye in response to changes in tension of the ciliary muscle, thereby allowing the lens system to bring into focus on the retina images of objects that are both near and far from the eye.

SUMMARY OF THE INVENTION

One aspect of the invention is an accommodating intraocular lens for implantation in an eye having an optical axis. The lens comprises an anterior portion which in turn comprises an anterior viewing element comprised of an optic having refractive power and an anterior biasing element comprising first and second anterior translation members extending from the anterior viewing element. The lens further comprises a posterior portion which in turn comprises a posterior viewing element in spaced relationship to the anterior viewing element and a posterior biasing element comprising first and second posterior translation members extending from the posterior viewing element. The anterior portion and posterior portion meet at first and second apices of the intraocular lens such that a plane perpendicular to the optical axis and passing through the apices is closer to one of said viewing elements than to the other of said viewing elements. The anterior portion and the posterior portion are responsive to force thereon to cause the separation between the viewing elements to change.

Another aspect of the invention is an accommodating intraocular lens for implantation in an eye having an optical axis. The lens comprises an anterior portion, which in turn comprises an anterior viewing element comprised of an optic having refractive power, and an anterior biasing element comprising first and second anterior translation members extending from the anterior viewing element. The lens further comprises a posterior portion which in turn comprises a posterior viewing element in spaced relationship to the anterior viewing element, and a posterior biasing element comprising first and second posterior translation members extending from the posterior viewing element. The anterior portion and posterior portion meet at first and second apices of the intraocular lens. The anterior portion and the posterior portion are responsive to force thereon to cause the separation between the viewing elements to change. The first anterior translation member forms a first anterior biasing angle, as the lens is viewed from the side, with respect to a plane perpendicular to the optical axis and passing through the apices. The first posterior translation member forms a first posterior biasing angle, as the lens is viewed from the side, with respect to the plane. The first anterior biasing angle and the first posterior biasing angle are unequal.

Another aspect of the invention is an accommodating intraocular lens comprising an anterior viewing element comprised of an optic having refractive power of less than 55 diopters and a posterior viewing element comprised of an optic having refractive power. The optics provide a combined power of 15–25 diopters and are mounted to move relative to each other along the optical axis in response to a contractile force by the ciliary muscle of the eye upon the capsular bag of the eye. The relative movement corresponds to change in the combined power of the optics of at least one diopter. Alternatively, the accommodating intraocular lens can further comprise a posterior viewing element comprised of an optic having a refractive power of zero to minus 25 diopters.

A further aspect of the invention is an accommodating intraocular lens comprising an anterior portion which in turn comprises an anterior viewing element which has a periphery and is comprised of an optic having refractive power. The anterior portion further comprises an anterior biasing element comprising first and second anterior translation members extending from the anterior viewing element. The lens further comprises a posterior portion which in turn comprises a posterior viewing element having a periphery, the posterior viewing element being in spaced relationship to the anterior viewing element, and a posterior biasing element comprising first and second posterior translation members extending from the posterior viewing element. The first anterior translation member and the first posterior translation member meet at a first apex of the intraocular lens, and the second anterior translation member and the second posterior translation member meet at a second apex of the intraocular lens, such that force on the anterior portion and the posterior portion causes the separation between the viewing elements to change. Each of the translation members is attached to one of the viewing elements at at least one attachment location. All of the attachment locations are further away from the apices than the peripheries of the viewing elements are from the apices.

A further aspect of the invention is an accommodating intraocular lens comprising an anterior portion comprised of a viewing element. The viewing element is comprised of an optic having refractive power. The lens further comprises a posterior portion comprised of a viewing element. The viewing elements are mounted to move relative to each other along the optical axis in response to force generated by the ciliary muscle of the eye. The lens further comprises a distending portion comprised of a distending member having a fixed end attached to the posterior portion and a free end sized and oriented to distend a portion of the lens capsule such that coupling of forces between the lens capsule and the intraocular lens is modified by the distending portion.

A further aspect of the invention is an accommodating intraocular lens. The lens comprises an anterior portion comprised of an anterior viewing element and an anterior biasing element connected to the anterior viewing element. The anterior viewing element is comprised of an optic having refractive power. The lens further comprises a posterior portion comprised of a posterior viewing element and a posterior biasing element connected to the posterior viewing element. The lens has an optical axis which is adapted to be substantially coincident with the optical axis of the eye upon implantation of the lens. The anterior and posterior viewing elements are mounted to move relative to each other along the optical axis in response to force generated by the ciliary muscle of the eye. The biasing elements are joined at first and second apices which are spaced from the optical axis of the lens. The lens further comprises a distending member extending between the first and second apices.

A further aspect of the invention is an accommodating intraocular lens comprising an anterior portion comprised of a viewing element. The viewing element is comprised of an optic having refractive power. The lens further comprises a posterior portion comprised of a viewing element. The viewing elements are mounted to move relative to each other along the optical axis in response to force generated by the ciliary muscle of the eye. The lens further comprises a retention portion comprised of a retention member having a fixed end attached to the anterior portion and a free end sized and oriented to contact a portion of the lens capsule such that extrusion of the implanted lens through the lens capsule opening is inhibited.

A further aspect of the invention is an accommodating intraocular lens. The lens comprises an anterior portion comprised of a viewing element, the viewing element comprised of an optic having refractive power, and a posterior portion comprised of a viewing element. The viewing elements are mounted to move relative to each other along the optical axis in response to force generated by the ciliary muscle of the eye. The lens further comprises a distending portion comprised of a distending member attached to one of the portions, and oriented to distend the lens capsule such that the distance between a posterior side of the posterior viewing element and an anterior side of the anterior viewing element along the optical axis is less than 3 mm when the ciliary muscle is relaxed and the lens is in an unaccommodated state.

A further aspect of the invention is an accommodating intraocular lens. The lens comprises an anterior portion comprised of a viewing element, the viewing element comprised of an optic having refractive power, and a posterior portion comprised of a viewing element. The viewing elements are mounted to move relative to each other along the optical axis in response to force generated by the ciliary muscle of the eye. The lens further comprises a distending portion comprised of a distending member attached to one of the portions, and oriented to distend the lens capsule. The distending causes the lens capsule to act on at least one of the posterior and anterior portions such that separation between the viewing elements is reduced when the ciliary muscle is relaxed and the lens is in an unaccommodated state.

A further aspect of the invention is an accommodating intraocular lens. The lens comprises an anterior portion comprised of a viewing element, the viewing element comprised of an optic having refractive power, and a posterior portion comprised of a viewing element. The viewing elements are mounted to move relative to each other along the optical axis in response to force generated by the ciliary muscle of the eye. The lens further comprises a distending member attached to the posterior portion. The distending member is separate from the biasing members and reshapes the lens capsule such that force coupling between the ciliary muscle and the lens is modified to provide greater relative movement between the viewing elements when the lens moves between an unaccommodated state and an accommodated state in response to the ciliary muscle.

A further aspect of the invention is an accommodating intraocular lens. The lens comprises an anterior portion comprised of an anterior viewing element and an anterior biasing element connected to the anterior viewing element, the anterior viewing element being comprised of an optic having refractive power. The lens further comprises a posterior portion comprised of a posterior viewing element and a posterior biasing element connected to the posterior viewing element. The lens has an optical axis which is adapted to be substantially coincident with the optical axis of the eye upon implantation of the lens. The anterior and posterior viewing elements are mounted to move relative to each other along the optical axis in response to force generated by the ciliary muscle of the eye. The biasing elements are joined at first and second apices which are spaced from the optical axis of the lens. The lens further comprises first and second distending members. Each of the members is attached to one of the anterior and posterior portions and extends away from the optical axis. The first member is disposed between the apices on one side of the intraocular lens and the second member is disposed between the apices on the opposite side of the intraocular lens. The distending members are oriented to distend portions of the lens capsule such that the viewing elements are relatively movable through a range of at least 1.0 mm in response to contraction of the ciliary muscle.

A further aspect of the invention is an accommodating intraocular lens comprising an anterior portion which is in turn comprised of a viewing element. The anterior viewing element is comprised of an optic having a diameter of approximately 3 mm or less and a refractive power of less than 55 diopters. The lens further comprises a posterior portion comprised of a viewing element. The viewing elements are mounted to move relative to each other along the optical axis in response to force generated by the ciliary muscle of the eye. The lens further comprises a distending portion comprised of a distending member having a fixed end attached to the posterior portion and a free end sized and oriented to distend a portion of the lens capsule such that coupling of forces between the lens capsule and the intraocular lens is increased.

A further aspect of the invention is an accommodating intraocular lens. The lens comprises an anterior portion comprised of a viewing element, the anterior viewing element being comprised of an optic having a refractive portion with a refractive power of less than 55 diopters. The lens further comprises a posterior portion comprised of a viewing element. The lens has an optical axis which is adapted to be substantially coincident with the optical axis of the eye upon implantation of the lens. The posterior viewing element comprises an optic arranged substantially coaxially with the anterior optic on the optical axis of the lens. The posterior optic has a larger diameter than the refractive portion of the anterior optic. The posterior optic comprises a peripheral portion having positive refractive power and extending radially away from the optical axis of the lens beyond the periphery of the refractive portion of the anterior optic, so that at least a portion of the light rays incident upon the posterior optic can bypass the refractive portion of the anterior optic.

A further aspect of the invention is an accommodating intraocular lens. The lens comprises an anterior portion comprised of a viewing element, the anterior viewing element being comprised of an optic having a refractive power of less than 55 diopters. The lens further comprises a posterior portion comprised of a viewing element. The lens has an optical axis which is adapted to be substantially coincident with the optical axis of the eye upon implantation of the lens. The posterior viewing element comprises an optic arranged substantially coaxially with the anterior optic on the optical axis of the lens. The posterior optic has a larger diameter than the anterior optic. The posterior optic comprises a peripheral portion having positive refractive power and extending radially away from the optical axis of the lens beyond the periphery of the anterior optic, so that at least a portion of the light rays incident upon the posterior optic can bypass the anterior optic.

A further aspect of the invention is an intraocular lens. The lens comprises an optic and a pair of elongate members extending from the optic. The members are comprised of a shape memory alloy.

A further aspect of the invention is an accommodating intraocular lens for implantation in an eye having an optical axis and a lens capsule having a capsule opening for receiving the lens. The lens comprises a posterior portion comprised of a posterior viewing element, and an anterior portion comprised of an anterior viewing element. The anterior viewing element is comprised of an optic having refractive power. The viewing elements are mounted to move relative to each other along the optical axis in response to force generated by the ciliary muscle of the eye. The anterior portion is adapted to contact portions of the lens capsule while being spaced from the lens capsule in at least one location so as to provide a fluid flow channel that extends from a region between the viewing elements to a region outside the capsule.

A further aspect of the invention is an accommodating intraocular lens. The lens comprises an anterior portion which in turn comprises an anterior viewing element having a periphery and comprised of an optic having refractive power, and an anterior biasing element comprising at least one anterior translation member attached to a first attachment area on the periphery of the anterior viewing element. The first attachment area has a thickness in a direction substantially perpendicular to the periphery and a width in a direction substantially parallel to the periphery. The ratio of the width to the thickness is equal to or greater than 3.

A further aspect of the invention is a method of manufacturing an intraocular lens having anterior and posterior viewing elements arranged along a common optical axis. The method comprises defining an anterior viewing element mold space and a posterior viewing element mold space, arranging the anterior viewing element mold space and the posterior viewing element mold space along a mold axis substantially coincident with the optical axis of the lens, and molding the anterior viewing element in the anterior viewing element mold space while the anterior viewing element mold space and the posterior viewing element mold space are arranged substantially along the mold axis.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention, certain preferred embodiments and modifications thereof will become apparent to those skilled in the art from the detailed description herein having reference to the figures that follow, of which:

FIG. 9 is a side sectional view of the lens system.

FIG. 10 is a top sectional view of the lens system.

FIG. 17.1 is a sectional view of an arm of the lens system.

FIG. 17.2 is a sectional view of another embodiment of the arm of the lens system.

FIG. 17.3 a sectional view of other embodiments of the arm of the lens system.

FIG. 17.4 is a side sectional view of another embodiment of the lens system.

FIG. 17.5 is a side sectional view of another embodiment of the lens system.

FIG. 21.1 is a front view of another embodiment of the lens system.

FIG. 21.2 is a front view of another embodiment of the lens system.

FIG. 21.3 is a front view of another embodiment of the lens system.

FIG. 22.1 is a side view of a stop member system employed in one embodiment of the lens system.

FIG. 23 is a side view of a mold system for forming the lens system.

FIG. 31 is a top view of the center mold portion.

FIG. 34.1 is a partial cross sectional view of an apex of the lens system, showing a set of expansion grooves formed therein.

FIG. 38.1 is a schematic view of another embodiment of the lens system, as implanted in the capsular bag.

FIG. 38.2 is a schematic view of the embodiment of FIG. 38.1, in the accommodated state.

FIG. 38.3 is a schematic view of biasers installed in the lens system.

FIG. 38.4 is a schematic view of another type of biasers installed in the lens system.

DETAILED DESCRIPTION OF THE PREFERRED EMBODIMENT

I. THE HUMAN EYE AND ACCOMMODATION

Figure 1:
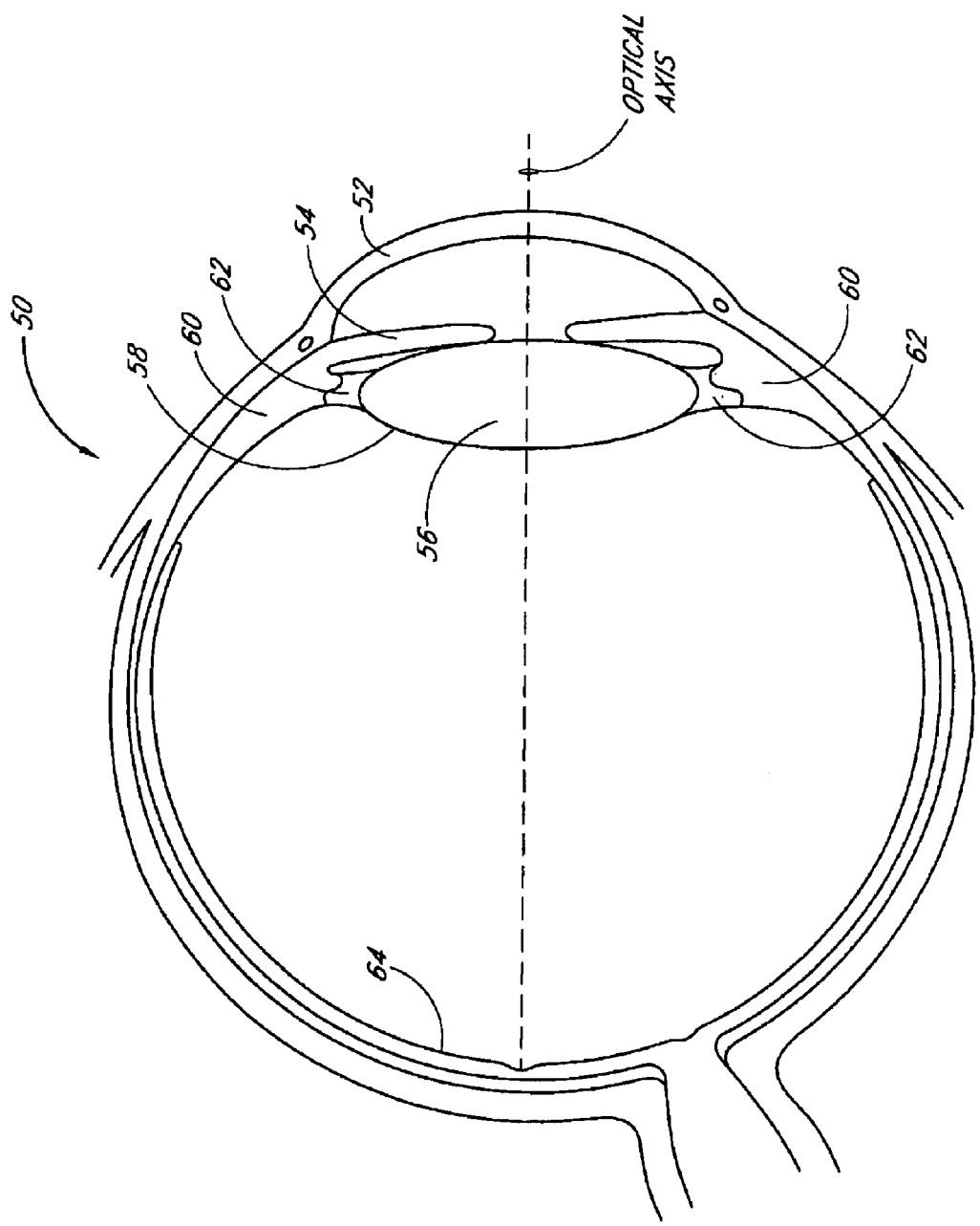
FIG. 1 is a sectional view of the human eye, with the lens in the unaccommodated state.
Figure 2:
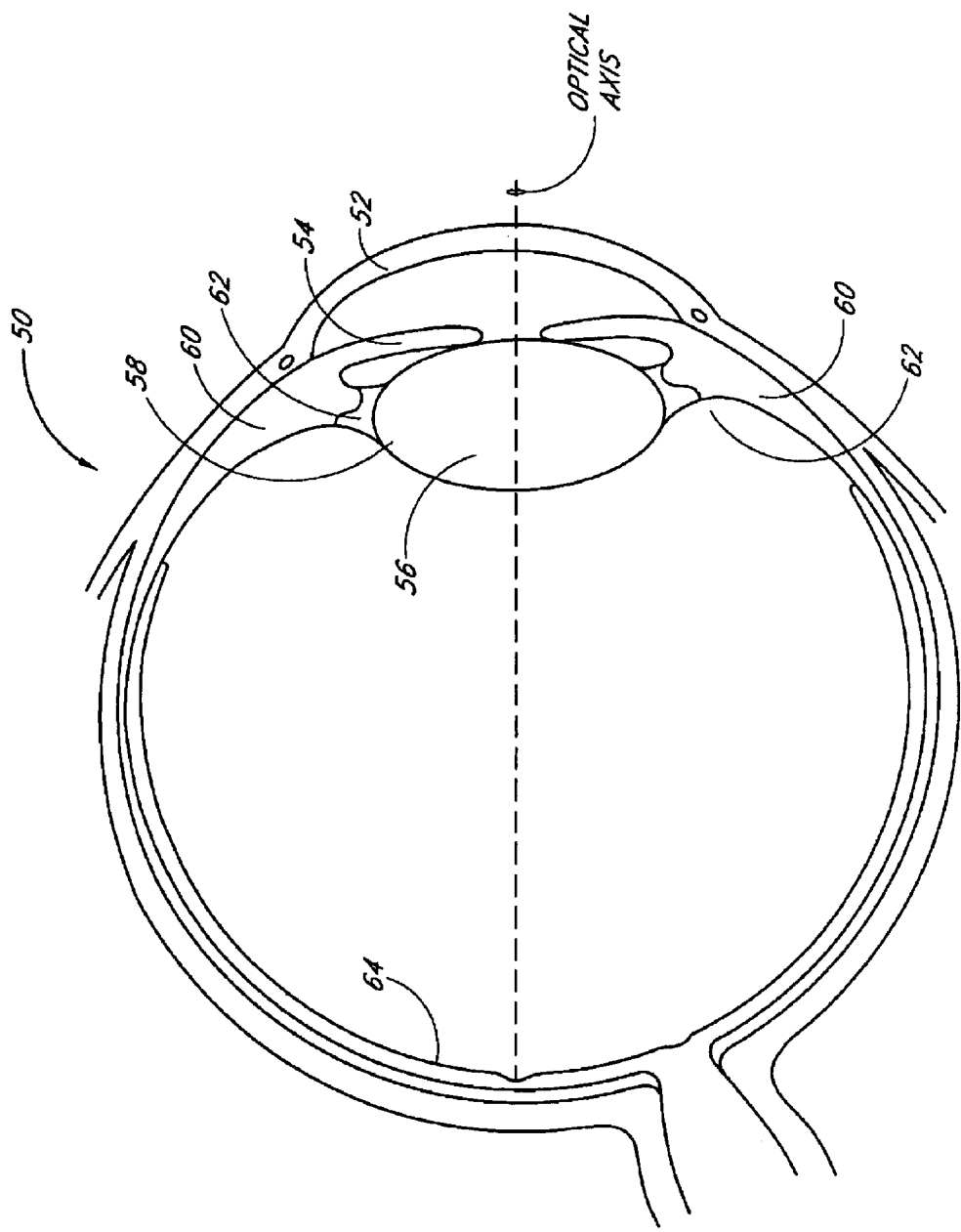
FIG. 2 is a sectional view of the human eye, with the lens in the accommodated state.

FIGS. 1 and 2 show the human eye 50 in section. Of particular relevance to the present disclosure are the cornea 52, the iris 54 and the lens 56, which is situated within the elastic, membranous capsular bag or lens capsule 58. The capsular bag 58 is surrounded by and suspended within the ciliary muscle 60 by ligament-like structures called zonules 62.

As light enters the eye 50, the cornea 52 and the lens 56 cooperate to focus the incoming light and form an image on the retina 64 at the rear of the eye, thus facilitating vision. In the process known as accommodation, the shape of the lens 56 is altered (and its refractive properties thereby adjusted) to allow the eye 50 to focus on objects at varying distances. A typical healthy eye has sufficient accommodation to enable focused vision of objects ranging in distance from infinity (generally defined as over 20 feet from the eye) to very near (closer than 10 inches).

The lens 56 has a natural elasticity, and in its relaxed state assumes a shape that in cross-section resembles a football. Accommodation occurs when the ciliary muscle 60 moves the lens from its relaxed or "unaccommodated" state (shown in FIG. 1) to a contracted or "accommodated" state (shown in FIG. 2). Movement of the ciliary muscle 60 to the relaxed/unaccommodated state increases tension in the zonules 62 and capsular bag 58, which in turn causes the lens 56 to take on a thinner (as measured along the optical axis) or taller shape as shown in FIG. 1. In contrast, when the ciliary muscle 60 is in the contracted/accommodated state, tension in the zonules 62 and capsular bag 58 is decreased and the lens 56 takes on the fatter or shorter shape shown in FIG. 2. When the ciliary muscles 60 contract and the capsular bag 58 and zonules 62 slacken, some degree of tension is maintained in the capsular bag 58 and zonules 62.

II. THE LENS SYSTEM: STRUCTURE

Figure 3:
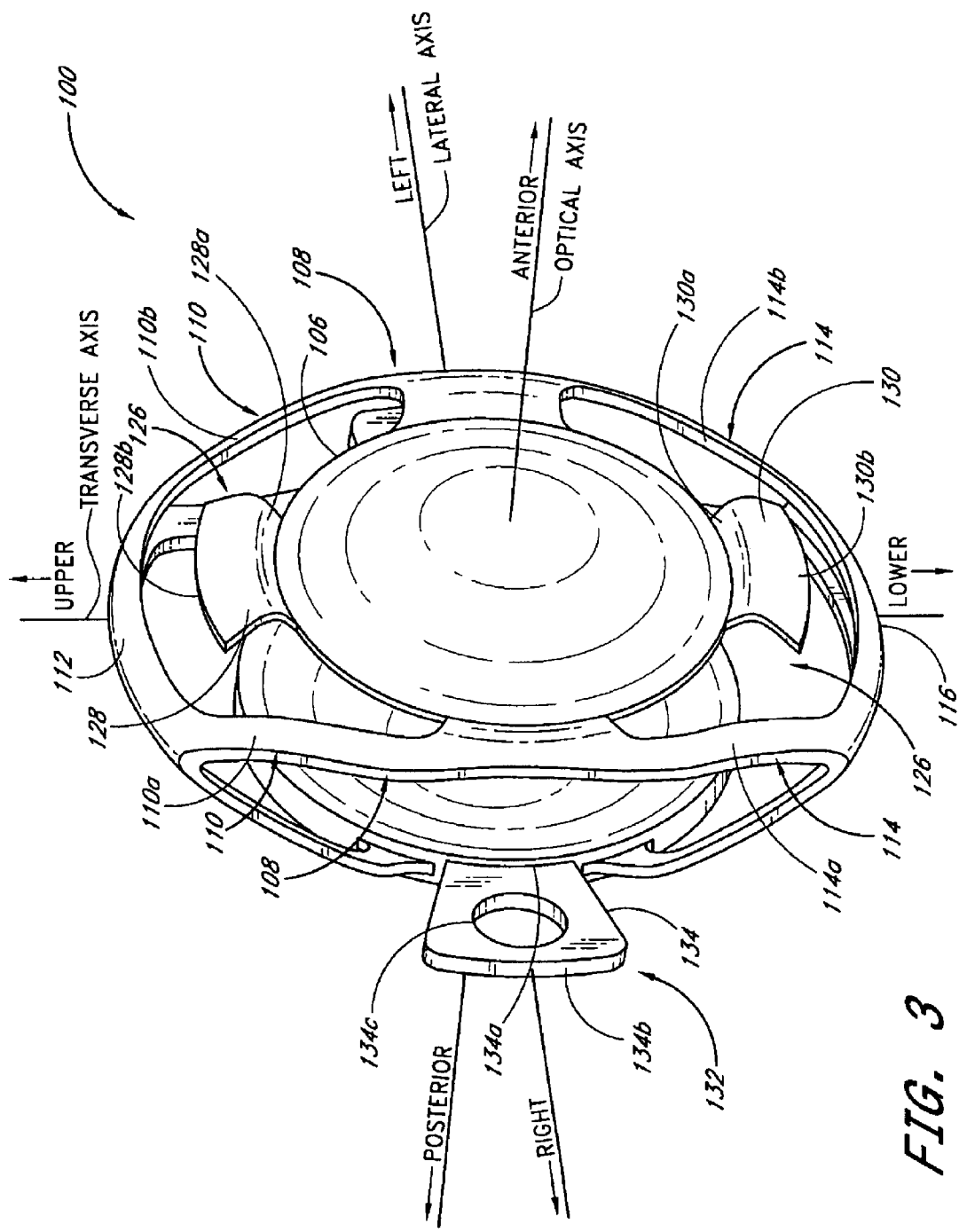
FIG. 3 is a perspective view of one embodiment of an intraocular lens system.

FIGS. 3–17 depict one embodiment of an intraocular lens system 100 which is configured for implantation into the capsular bag 58 in place of the natural lens 56, and is further configured to change the refractive properties of the eye in response to the eye's natural process of accommodation. With reference to FIG. 3, a set of axes is included to illustrate the sense of directional terminology which will be used herein to describe various features of the lens system 100. The terms "anterior" and "posterior" refer to the depicted directions on the optical axis of the lens 100 shown in FIG. 3. When the lens 100 is implanted in an eye, the anterior direction extends toward the cornea and the posterior direction extends toward the retina, with the optical axis of the lens substantially coincident with the optical axis of the eye shown in FIGS. 1 and 2. The terms "left" and "right" refer to the directions shown on the lateral axis, which is orthogonal to the optical axis. In addition, the terms "upper" and "lower" refer to the directions depicted on the transverse axis which is orthogonal to both of the optical axis and the lateral axis.

This system of axes is depicted purely to facilitate description herein; thus, it is not intended to limit the possible orientations which the lens system 100 may assume during use. For example, the lens system 100 may rotate about, or may be displaced along, the optical axis during use without detracting from the performance of the lens. It is clear that, should the lens system 100 be so rotated about the optical axis, the transverse axis may no longer have an upper-lower orientation and the lateral axis may no longer have a left-right orientation, but the lens system 100 will continue to function as it would when oriented as depicted in FIG. 3. Accordingly, when the terms "upper," "lower," "left" or "right" are used in describing features of the lens system 100, such use should not be understood to require the described feature to occupy the indicated position at any or all times during use of the lens system 100. Similarly, such use should not be understood to require the lens system 100 to maintain the indicated orientation at any or all times during use.

Figure 4:
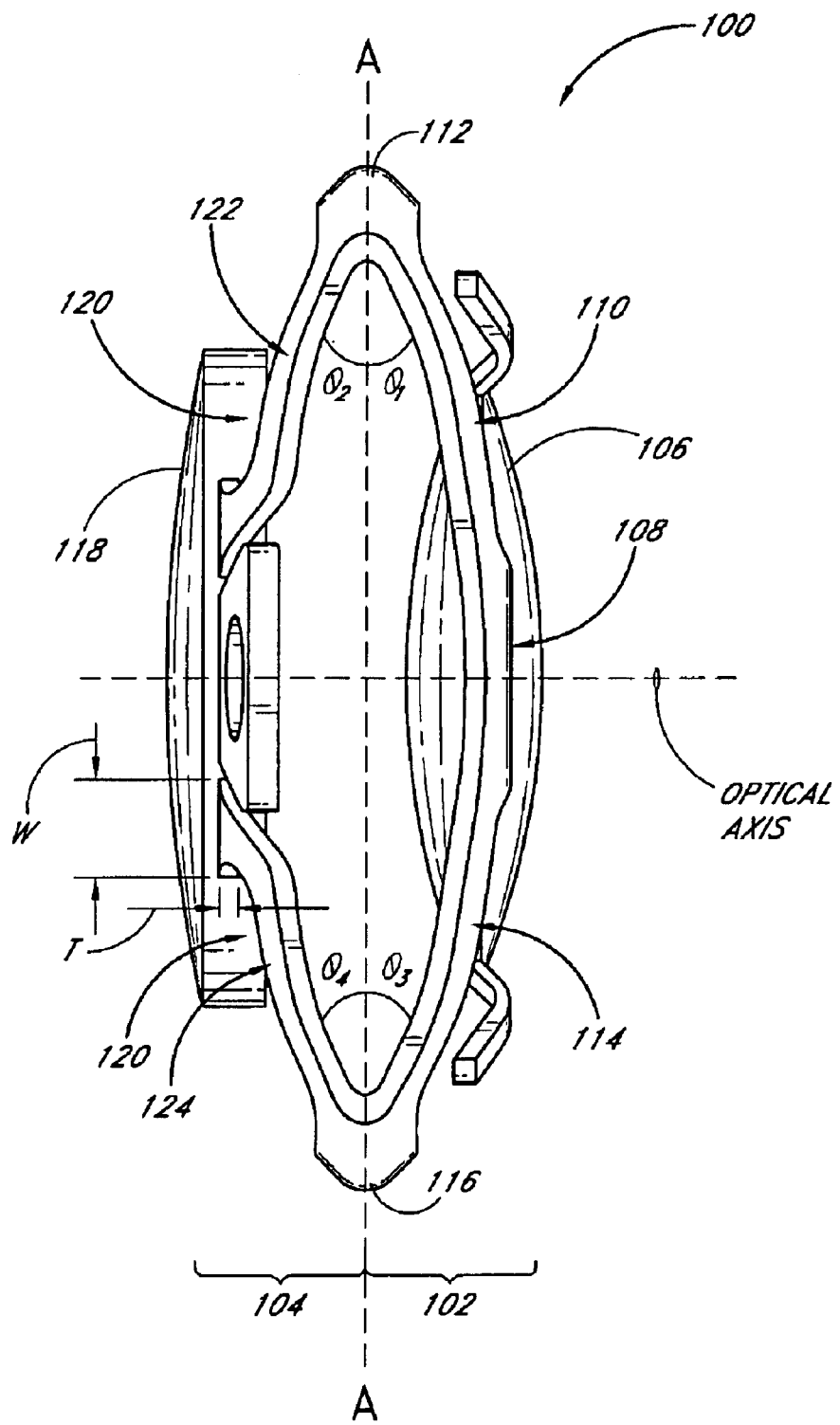
FIG. 4 is a side view of the lens system.

As best seen in FIG. 4, the lens system 100 has an anterior portion 102 which is anterior or forward of the line A—A (which represents a plane substantially orthogonal to the optical axis and intersecting first and second apices 112, 116) and a posterior portion 104 which is posterior or rearward of the line A—A. The anterior portion 102 comprises an anterior viewing element 106 and an anterior biasing element 108. The anterior biasing element 108 in turn comprises a first anterior translation member 110 which extends from the anterior viewing element 106 to the first apex 112 and a second anterior translation member 114 which extends from the anterior viewing element 106 to the second apex 116. In the illustrated embodiment the first anterior translation member 110 comprises a right arm 110a and a left arm 110b (see FIG. 3). In addition, the depicted second anterior translation member 114 comprises a right arm 114a and a left arm 114b. However, in other embodiments either or both of the first and second anterior translation members 110, 114 may comprise a single arm or member, or more than two arms or members.

Figure 5:
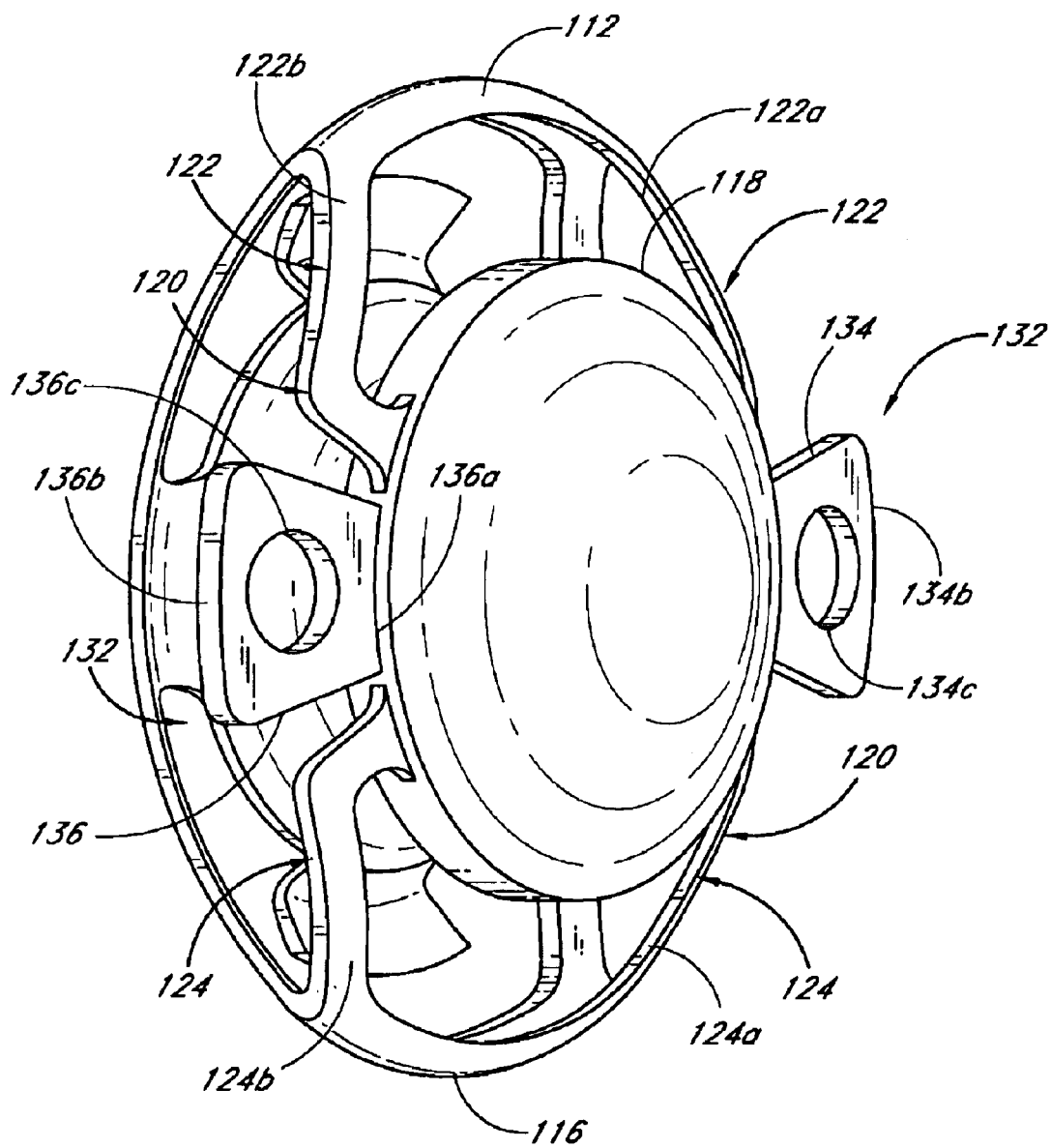
FIG. 5 is a rear perspective view of the lens system.
Figure 7:
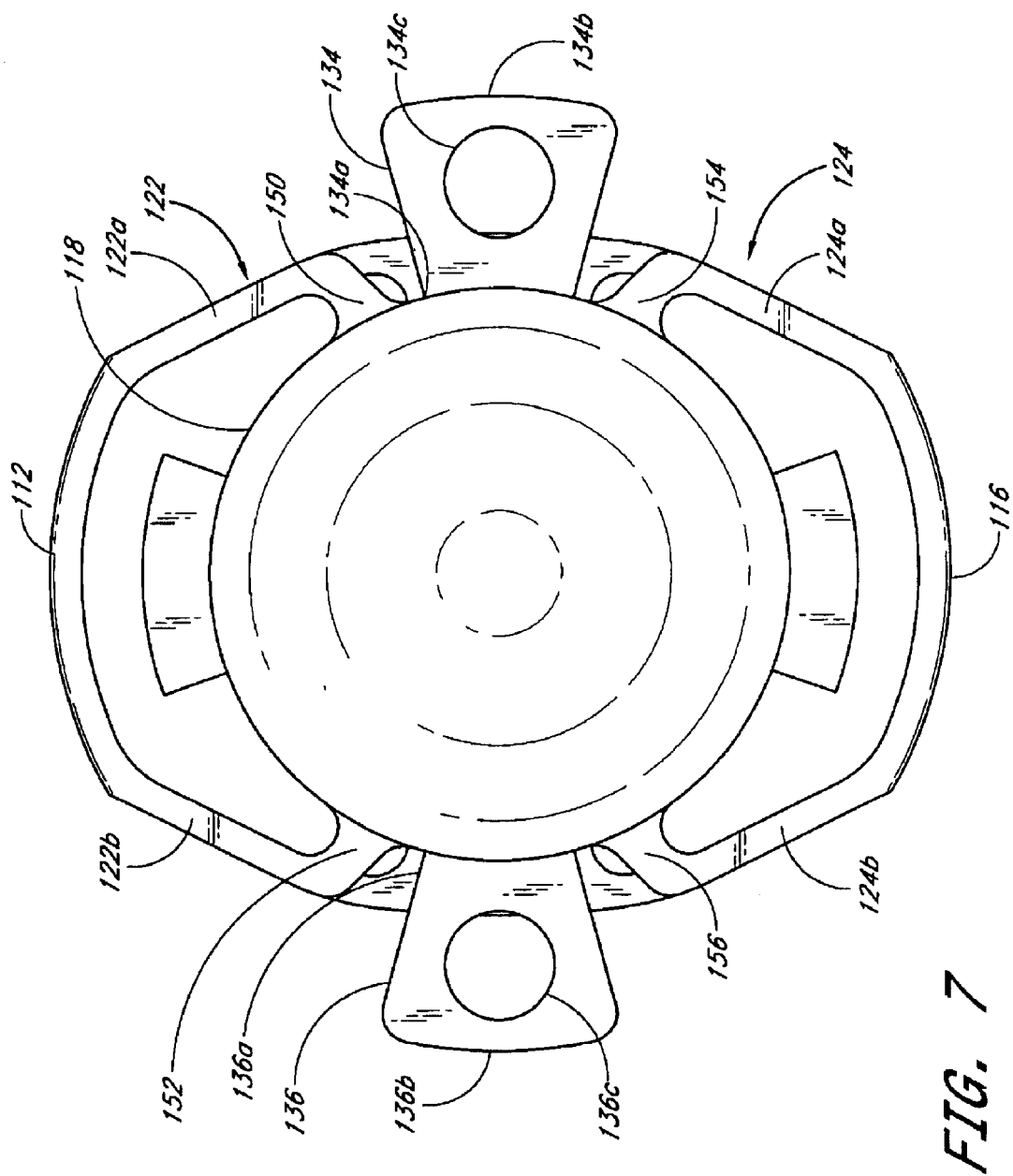
FIG. 7 is a rear view of the lens system.
Figure 8:
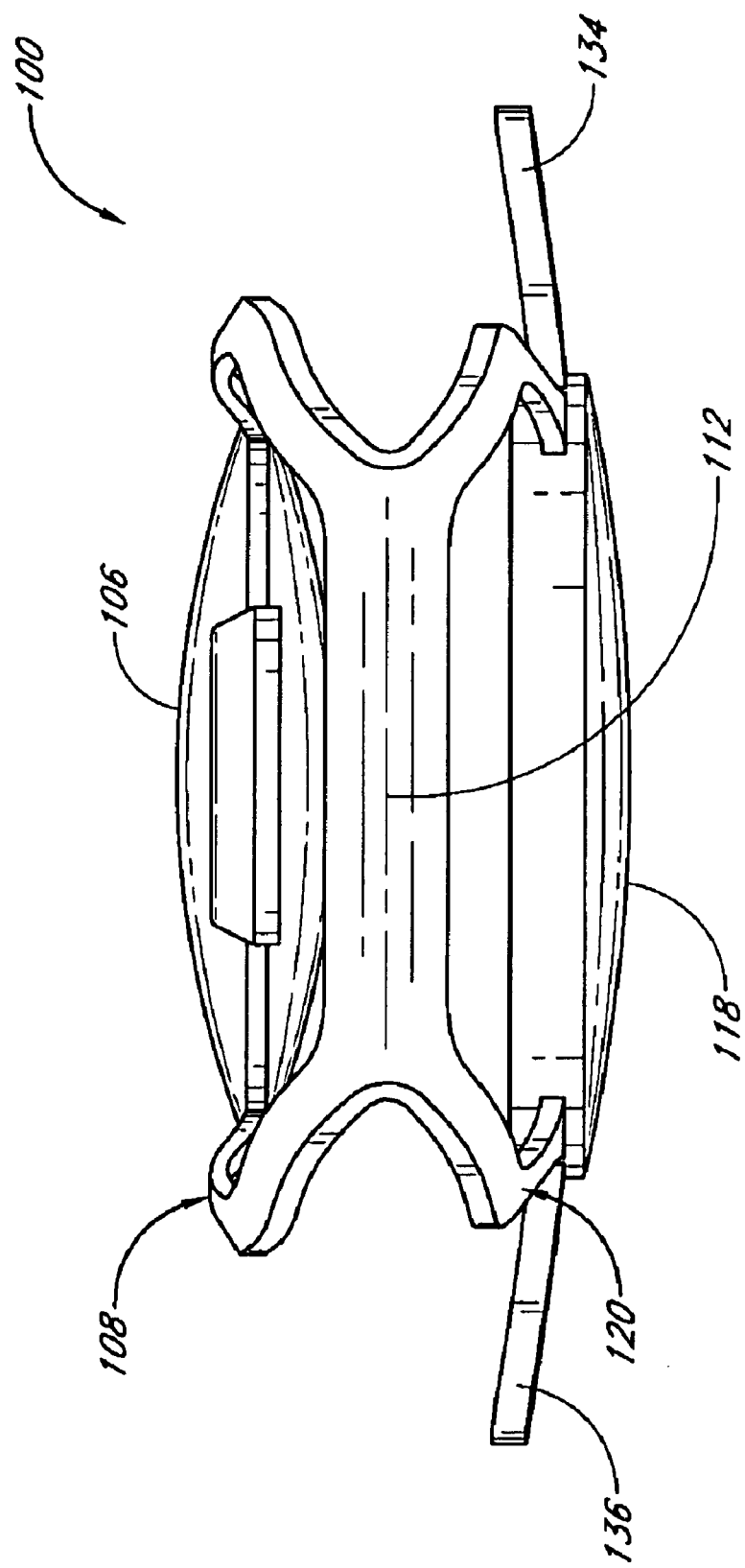
FIG. 8 is a top view of the lens system.
Figure 11:
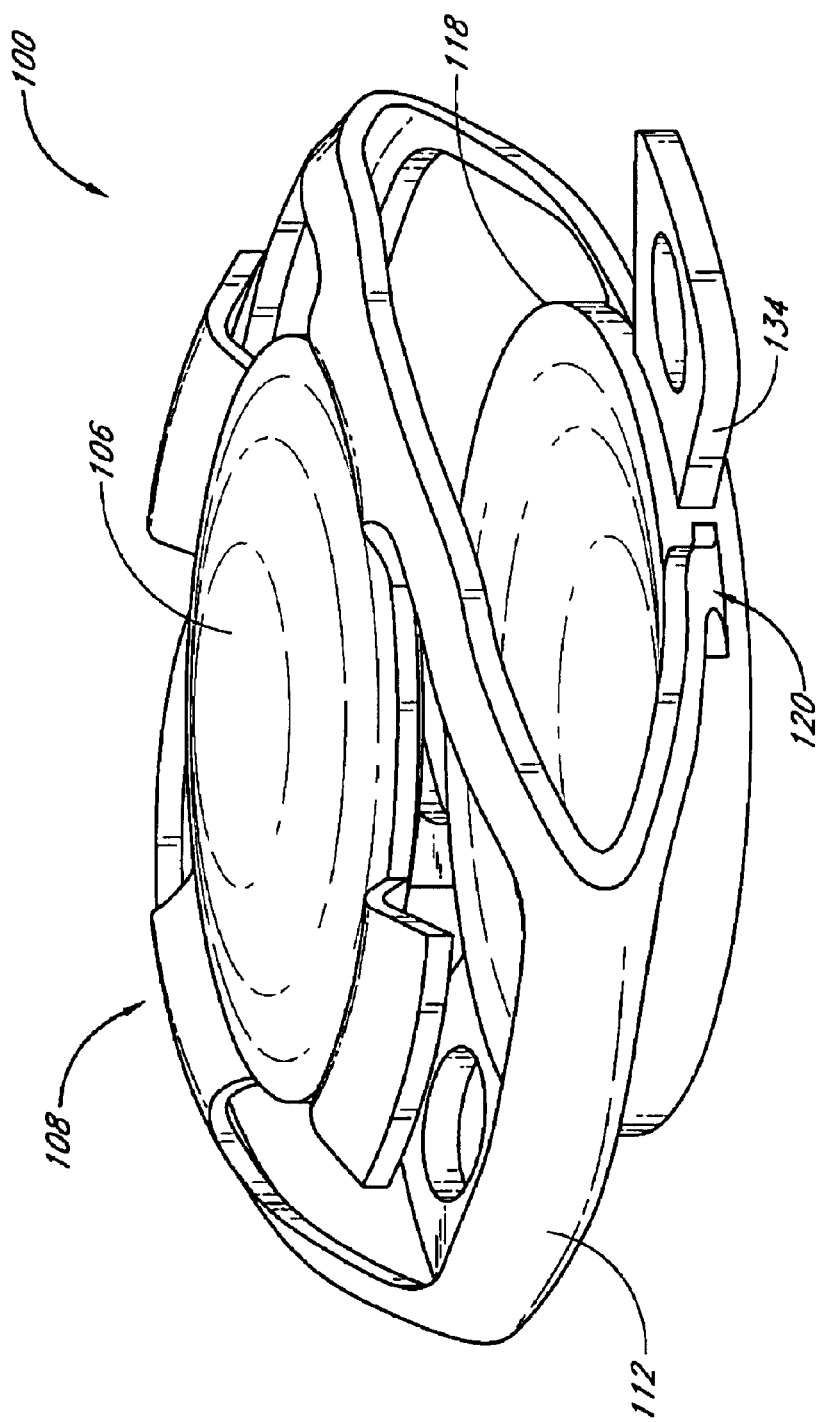
FIG. 11 is a second perspective view of the lens system.
Figure 12:
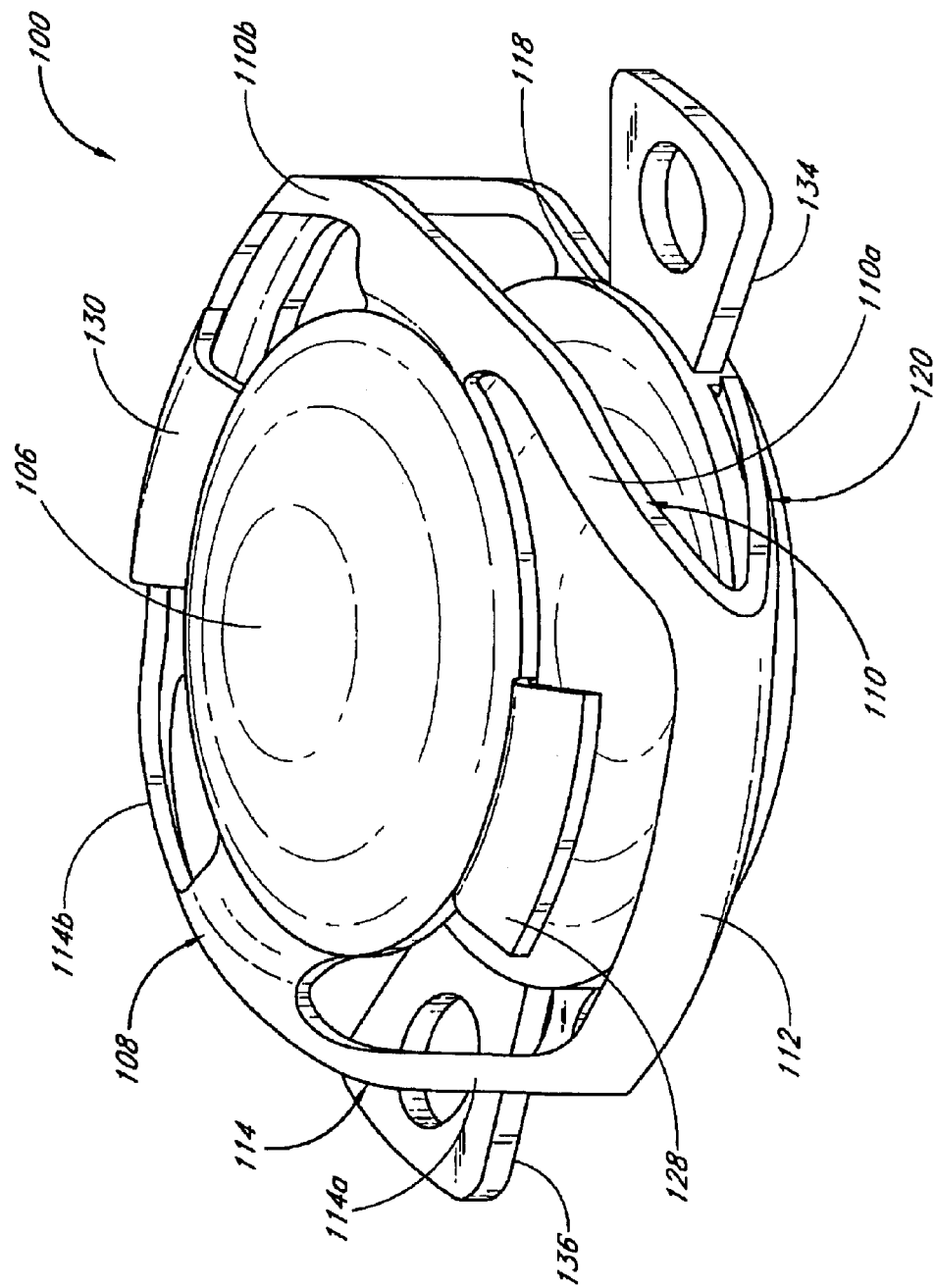
FIG. 12 is a third perspective view of the lens system.
Figure 14:
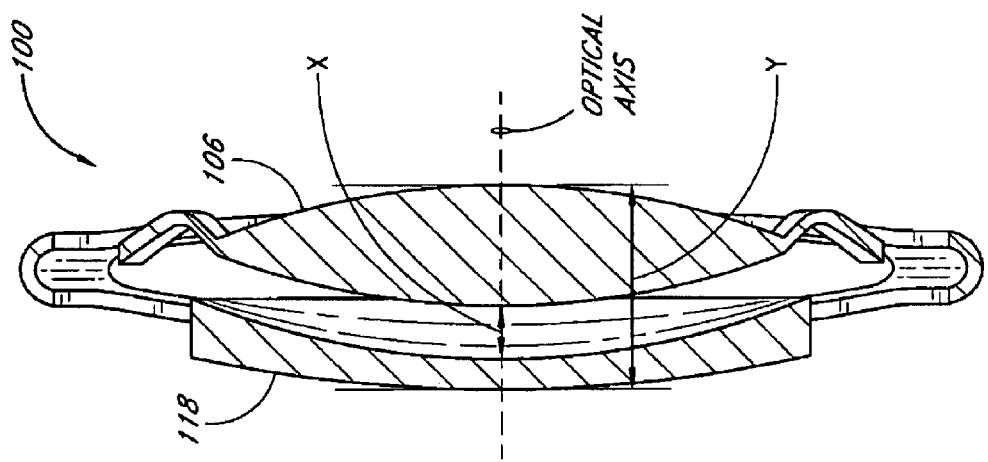
FIG. 14 is a side sectional view of the lens system in the unaccommodated state.
Figure 13:
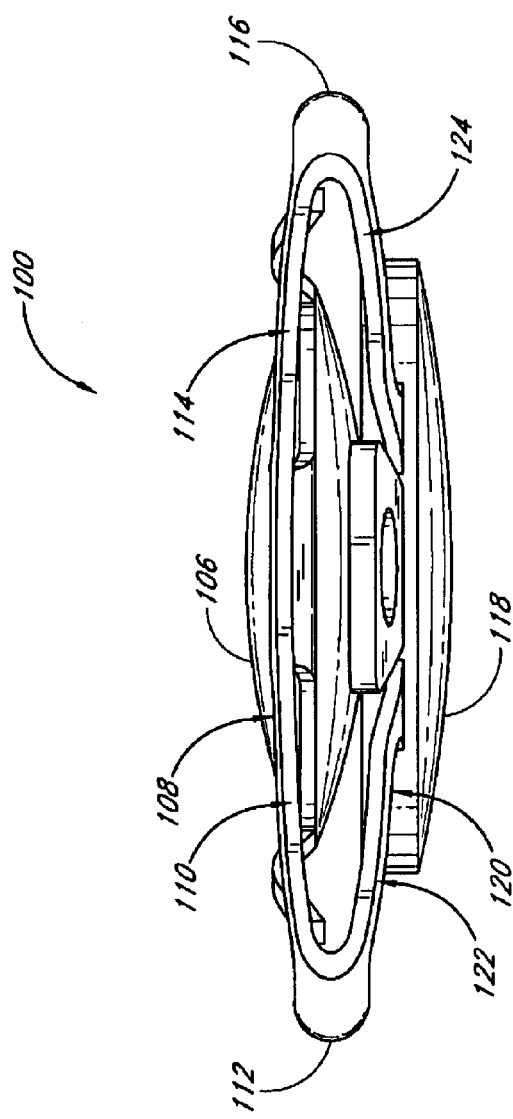
FIG. 13 is a side view of the lens system in the unaccommodated state.
Figure 15:
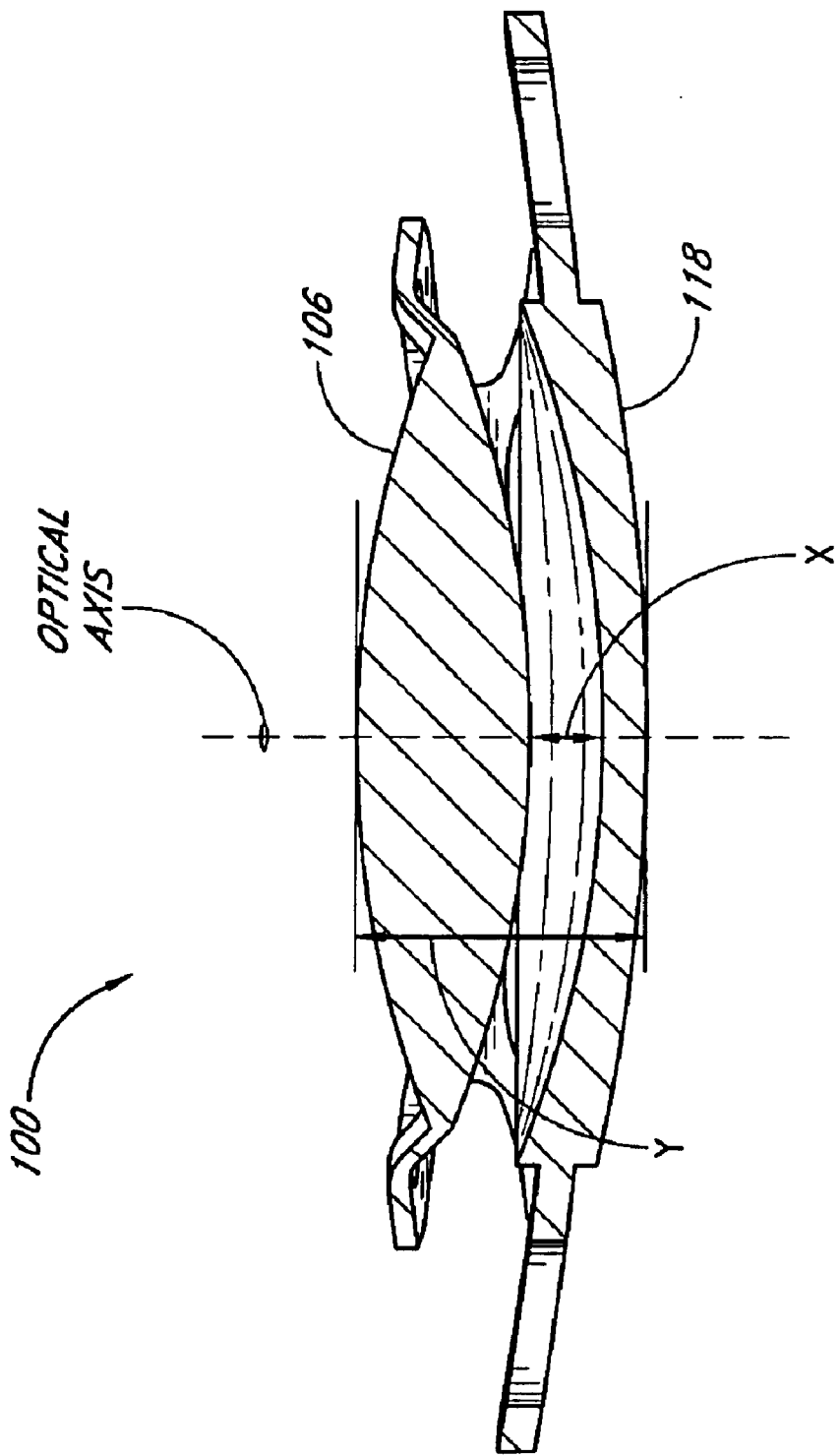
FIG. 15 is a top sectional view of the lens system in the unaccommodated state.
Figure 16:
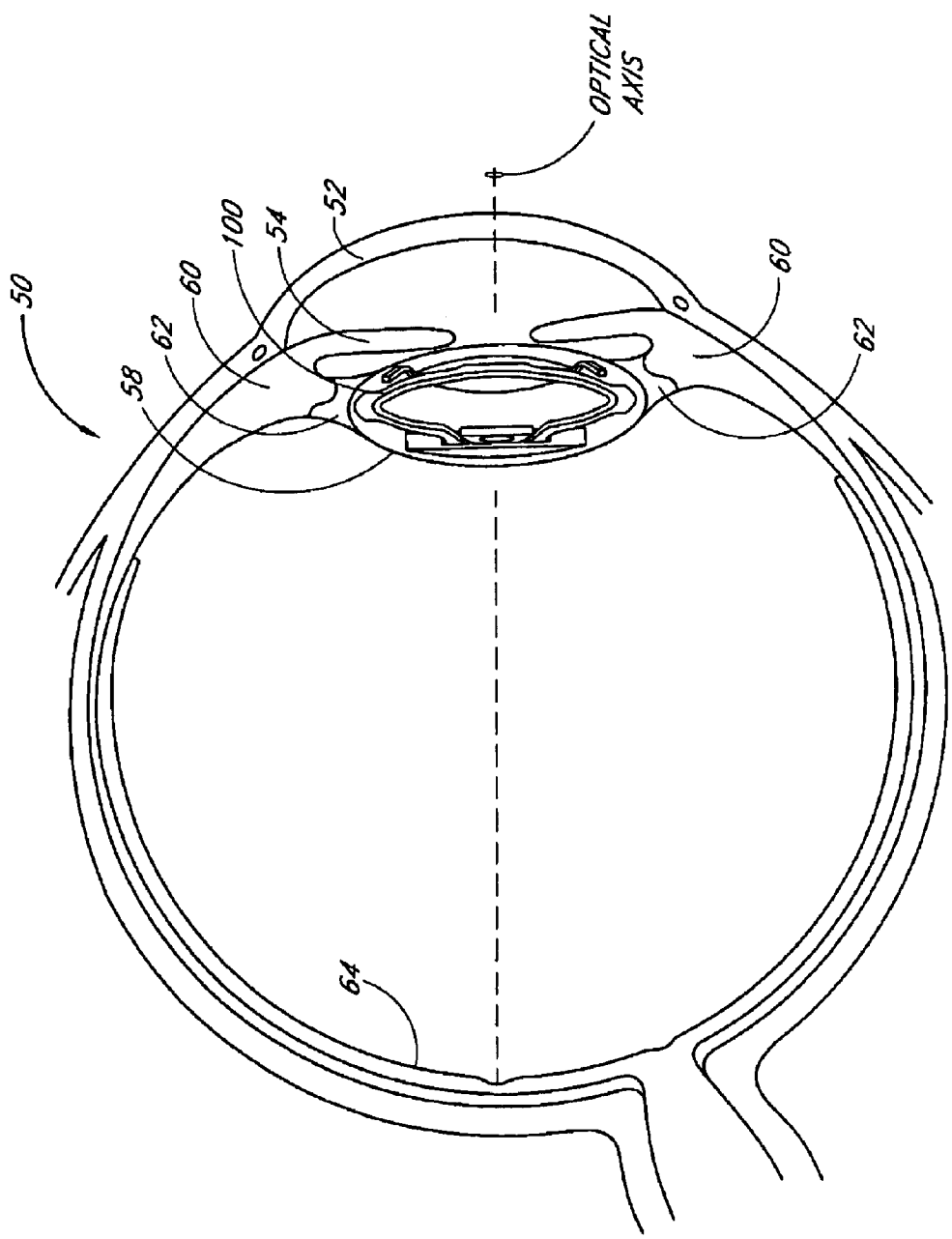
FIG. 16 is a sectional view of the human eye with the lens system implanted in the capsular bag and the lens system in the accommodated state.

As best seen in FIGS. 4, 5 and 7, the posterior portion 104 includes a posterior viewing element 118 and a posterior biasing element 120. The posterior biasing element 120 includes a first posterior translation member 122 extending from the posterior viewing element 118 to the first apex 112 and a second posterior translation member 124 extending from the posterior viewing element 118 to the second apex 116. In the illustrated embodiment, the first posterior translation member comprises a right arm 122a and a left arm 122b. Likewise, the depicted second posterior translation member 124 comprises a right arm 124a and a left arm 124b. However, in other embodiments either or both of the first and second posterior translation members 122, 124 may comprise a single arm or member, or more than two arms or members.

In the embodiment shown in FIG. 4, the anterior biasing element 108 and the posterior biasing element are configured symmetrically with respect to the plane A—A as the lens system 100 is viewed from the side. As used herein to describe the biasing elements 108, 120, "symmetric" or "symmetrically" means that, as the lens system 100 is viewed from the side, the first anterior translation member 110 and the first posterior translation member 122 extend from the first apex 112 at substantially equal first anterior and posterior biasing angles $\theta_1$, $\theta_2$ with respect to the line A—A (which, again, represents the edge of a plane which is substantially orthogonal to the optical axis and intersects the first and second apices 112, 116) and/or that the second anterior translation member 114 and the second posterior translation member 124 extend from the second apex 116 at substantially equal second anterior and posterior biasing angles $\theta_3$, $\theta_4$ with respect to the line A—A. Alternative or asymmetric configurations of the biasing elements are possible, as will be discussed in further detail below. It should be further noted that a symmetric configuration of the biasing elements 108, 120 does not dictate symmetric positioning of the viewing elements with respect to the line A—A; in the embodiment shown in FIG. 4 the anterior viewing element 106 is closer to the line A—A than is the posterior viewing element.

Preferably, both the anterior viewing element 106 and the posterior viewing element 118 comprise an optic or lens having refractive power. (As used herein, the term "refractive" or "refractive power" shall include "diffractive" or "diffractive power".) The preferred power ranges for the optics are discussed in detail below. In alternative embodiments one or both of the anterior and posterior viewing elements 106, 118 may comprise an optic with a surrounding or partially surrounding perimeter frame member or members, with some or all of the biasing elements/translation members attached to the frame member(s). As a further alternative, one of the viewing elements 106, 118 may comprise a perimeter frame with an open/empty central portion or void located on the optical axis (see FIG. 20 and discussion below), or a perimeter frame member or members with a zero-power lens or transparent member therein. In still further variations, one of the viewing elements 106, 118 may comprise only a zero-power lens or transparent member.

In a presently preferred embodiment, a retention portion 126 is coupled to the anterior portion 102, preferably at the anterior viewing element 106. The retention portion 126 preferably includes a first retention member 128 and a second retention member 130, although in alternative embodiments the retention portion 126 may be omitted altogether, or may comprise only one retention member or more than two retention members. The first retention member 128 is coupled to the anterior viewing element 106 at a fixed end 128a and also includes a free end 128b opposite the fixed end 128a. Likewise, the second retention member 130 includes a fixed end 130a and a free end 130b. The retention members 128, 130 are illustrated as being coupled to the anterior viewing element 106 at the upper and lower edges thereof; however, the retention members 128, 130 may alternatively be attached to the anterior viewing element 106 at other suitable edge locations.

In the preferred embodiment, the posterior portion 104 includes a distending portion 132, preferably attached to the posterior viewing element 118. The preferred distending portion 132 includes a first distending member 134 which in turn includes a fixed end 134a, a free end 134b opposite the fixed end 134a and preferably also includes an opening 134c formed therein. The preferred distending portion 132 also comprises a second distending member 136 with a fixed end 136a, a free end 136b and preferably an opening 136c formed therein. In alternative embodiments, the distending portion 132 may be omitted altogether, or may comprise a single distending member or more than two distending members. To optimize their effectiveness, the preferred location for the distending members 134, 136 is 90 degrees away (about the optical axis) from the apices 112, 116 on the posterior portion 104. Where the biasing elements form more than two apices (or where two apices are not spaced 180 degrees apart about the optical axis), one or more distending members may be positioned angularly midway between the apices about the optical axis. Alternatively, the distending member(s) may occupy other suitable positions relative to the apices (besides the "angularly midway" positions disclosed above); as further alternatives, the distending member(s) may be located on the anterior portion 102 of the lens system 100, or even on the apices themselves. The functions of the retention portion 126 and the distending portion 132 will be described in greater detail below.

III. THE LENS SYSTEM: FUNCTION/OPTICS

The anterior and posterior biasing elements 108, 120 function in a springlike manner to permit the anterior viewing element 106 and posterior viewing element 118 to move relative to each other generally along the optical axis. The biasing elements 108, 120 bias the viewing elements 106, 118 apart so that the elements 106, 108 separate to the accommodated position or accommodated state shown in FIG. 4. Thus, in the absence of any external forces, the viewing elements are at their maximum separation along the optical axis. The viewing elements 106, 118 of the lens system 100 may be moved toward each other, in response to a ciliary muscle force of up to 2 grams, to provide an unaccommodated position by applying appropriate forces upon the anterior and posterior portions 102, 104 and/or the apices 112, 116.

When the lens system 100 is implanted in the capsular bag 58 (FIGS. 16–17) the above described biasing forces cause the lens system 100 to expand along the optical axis so as to interact with both the posterior and anterior aspects of the capsular bag. Such interaction occurs throughout the entire range of motion of the ciliary muscle 60. At one extreme the ciliary muscle is relaxed and the zonules 62 pull the capsular bag 58 radially so as to cause the bag to become more disk shaped. The anterior and posterior sides of the bag, in turn, apply force to the anterior and posterior portions 102, 104 of the lens system 100, thereby forcing the viewing elements 106, 118 toward each other into the accommodated position. At the other extreme, the ciliary muscle contracts and the zonules 62 move inwardly to provide slack in the capsular bag 58 and allow the bag to become more football-shaped. The slack in the bag is taken up by the lens system due to the biasing-apart of the anterior and posterior viewing elements 106, 118. As the radial tension in the bag is reduced, the viewing elements 106, 118 move away from each other into an accommodated position. Thus, the distance between the viewing elements 106, 118 depends on the degree of contraction or relaxation of the ciliary muscle 60. As the distance between the anterior and posterior viewing elements 106, 118 is varied, the focal length of the lens system 100 changes accordingly. Thus, when the lens system 100 is implanted into the capsular bag (see FIGS. 16–17) the lens system 100 operates in conjunction with the natural accommodation processes of the eye to move between the accommodated (FIG. 16) and unaccommodated (FIG. 17) states in the same manner as would a healthy "natural" lens. Preferably, the lens system 100 can move between the accommodated and unaccommodated states in less than about one second.

The lens system 100 has sufficient dynamic range that the anterior and posterior viewing elements 106, 118 move about 0.5–4 mm, preferably about 1–3 mm, more preferably about 1–2 mm, and most preferably about 1.5 mm closer together when the lens system 100 moves from the accommodated state to the unaccommodated state. In other words the separation distance X (see FIGS. 9–10, 14–15) between the anterior and posterior viewing elements 106, 118, which distance may for present purposes be defined as the distance along the optical axis (or a parallel axis) between a point of axial intersection with the posterior face of the anterior viewing element 106 and a point of axial intersection with the anterior face of the posterior viewing element 118, decreases by the amount(s) disclosed above upon movement of the lens system 100 to the unaccommodated state. Simultaneously, in the preferred mode the total system thickness Y decreases from about 3.0–4.0 mm in the accommodated state to about 1.5–2.5 mm in the unaccommodated state.

Figure 6:
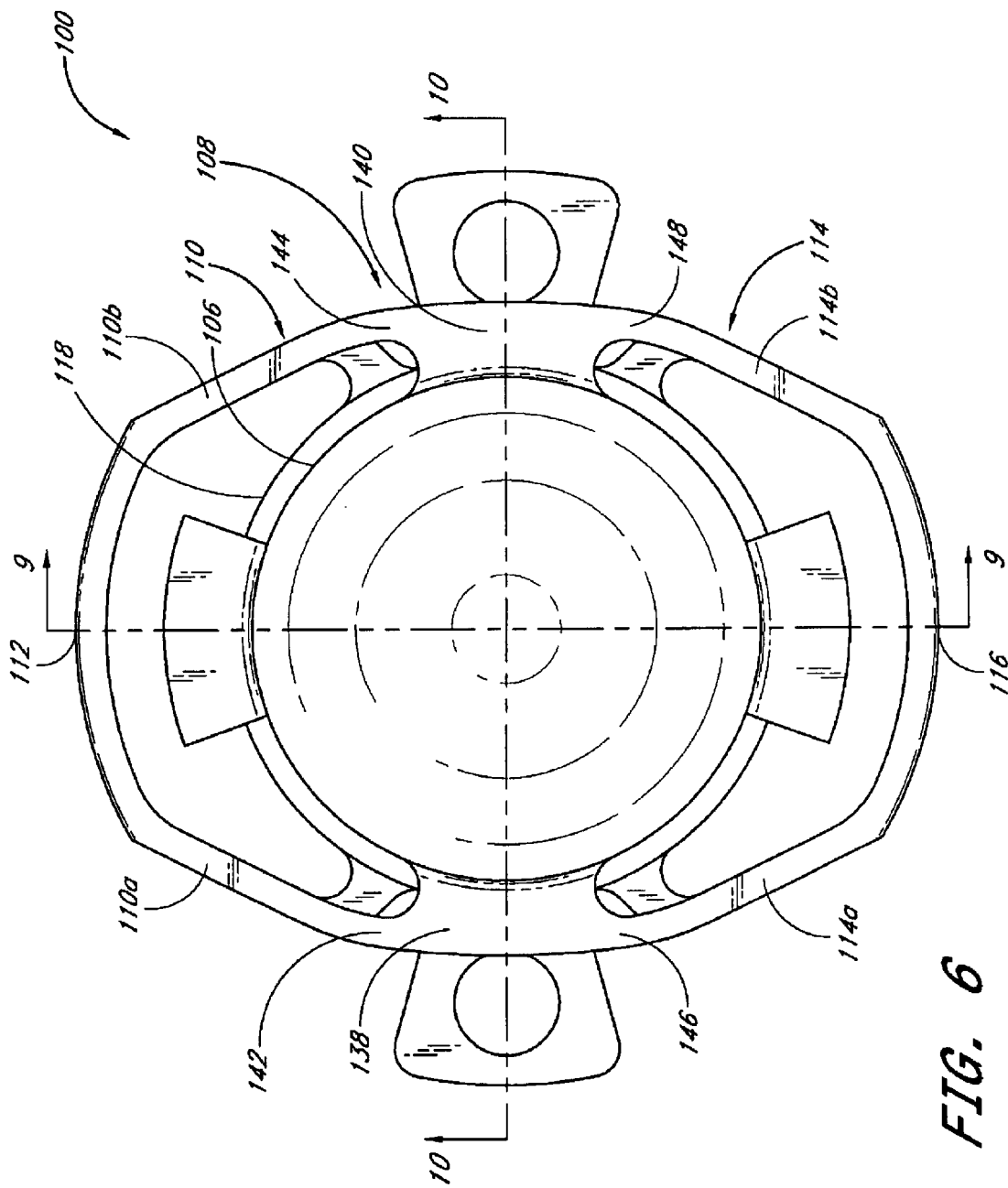
FIG. 6 is a front view of the lens system.

As may be best seen in FIG. 6, the first anterior translation member 110 connects to the anterior viewing element 106 via connection of the left and right arms 110a, 110b to first and second transition members 138, 140 at attachment locations 142, 144. The second anterior translation member 114 connects to the anterior viewing element 106 via connection of left and right arms 114a, 114b to the first and second transition members 138, 140 at attachment locations 146, 148. This is a presently preferred arrangement for the first and second anterior translation members 110, 114; alternatively, the first and second anterior translation members 110, 114 could be connected directly to the anterior viewing element 106, as is the case with the connection of the first and second posterior translation members 122, 124 to the posterior viewing element 118.

However the connection is established between the first and second anterior translation members 110, 114 and the anterior viewing element 106, it is preferred that the attachment locations 142, 144 corresponding to the first anterior translation member 110 be farther away from the first apex 112 than is the closest edge or the periphery of the anterior viewing element 106. This configuration increases the effective length of the first anterior translation member 110/arms 110a, 110b, in comparison to a direct or straight attachment between the apex 112 and the nearest/top edge of the anterior viewing element 106. For the same reasons, it is preferred that the attachment locations 146, 148 associated with the second anterior translation member 114 be farther away from the second apex 116 than is the closest/bottom edge of the anterior viewing element 106.

As best seen in FIG. 7, the first posterior translation member 122 is preferably connected directly to the posterior viewing element 118 via attachment of the left and right arms 122a, 122b to the element 118 at attachment points 150, 152. Likewise, the second posterior translation member 124 is preferably directly connected to the posterior viewing element 118 via connection of the left and right arms 124a, 124b to the element 118 at attachment points 154, 156, respectively. In alternative embodiments, the first and second posterior translation members 124, 122 can be connected to the posterior viewing element via intervening members as is done with the anterior viewing element 106. No matter how these connections are made, it is preferred that the attachment locations 150, 152 be spaced further away from the first apex 112 than is the nearest edge or the periphery of the posterior viewing element 118. Similarly, it is preferred that the attachment locations 154, 156 be spaced further away from the second apex 116 than is the closest edge of the posterior viewing element 118.

By increasing the effective length of some or all of the translation members 110, 114, 122, 124 (and that of the arms 110a, 110b, 114a, 114b, 122a, 122b, 124a, 124b where such structure is employed), the preferred configuration of the attachment locations 142, 144, 146, 148, 150, 152, 154, 156 relative to the first and second apices 112, 116 enables the anterior and/or posterior viewing elements 106, 118 to move with respect to one another a greater distance along the optical axis, for a given angular displacement of the anterior and/or posterior translation members. This arrangement thus facilitates a more responsive spring system for the lens system 100 and minimizes material fatigue effects associated with prolonged exposure to repeated flexing.

In the illustrated embodiment, the attachment location 142 of the first anterior translation member 110 is spaced from the corresponding attachment location 146 of the second anterior translation member 114 along the periphery of the anterior viewing element, and the same relationship exists between the other pairs of attachment locations 144, 148; 150, 154; and 152, 156. This arrangement advantageously broadens the support base for the anterior and posterior viewing elements 106, 118 and prevents them from twisting about an axis parallel to the lateral axis, as the viewing elements move between the accommodated and unaccommodated positions.

It is also preferred that the attachment locations 142, 144 of the first anterior translation member 110 be located equidistant from the first apex 112, and that the right and left arms 110a, 110b of the member 110 be equal in length. Furthermore, the arrangement of the attachment locations 146, 148, arms 114a, 114b and second apex preferably mirrors that recited above regarding the first anterior translation member 110, while the apices 112, 116 are preferably equidistant from the optical axis and are situated 180 degrees apart. This configuration maintains the anterior viewing element 106 orthogonal to the optical axis as the viewing element 106 moves back and forth and the anterior viewing element flexes.

For the same reasons, a like combination of equidistance and equal length is preferred for the first and second posterior translation members 122, 124 and their constituent arms 122a, 122b, 124a, 124b and attachment points 150, 152, 154, 156, with respect to the apices 112, 116. However, as shown the arms 122a, 122b, 124a, 124b need not be equal in length to their counterparts 110a, 110b, 114a, 114b in the first and second anterior translation members 110, 114.

Where any member or element connects to the periphery of the anterior or posterior viewing elements 106, 118, the member defines a connection geometry or attachment area with a connection width W and a connection thickness T (see FIG. 4 and the example illustrated therein, of the connection of the second posterior translation member 124 to the posterior viewing element 118). For purposes of clarity, the connection width is defined as being measured along a direction substantially parallel to the periphery of the viewing element in question, and the connection thickness is defined as measured along a direction substantially perpendicular to the periphery of the viewing element. (The periphery itself is deemed to be oriented generally perpendicular to the optical axis as shown in FIG. 4.) Preferably, no attachment area employed in the lens system 100 has a ratio of width to thickness less than 3. It has been found that such a geometry reduces distortion of the viewing element/optic due to localized forces. For the same reasons, it is also preferred that each of the translation members 110, 114, 122, 124 be connected to the periphery of the respective viewing elements at least two attachment areas, each having the preferred geometry discussed above.

Figure 17:
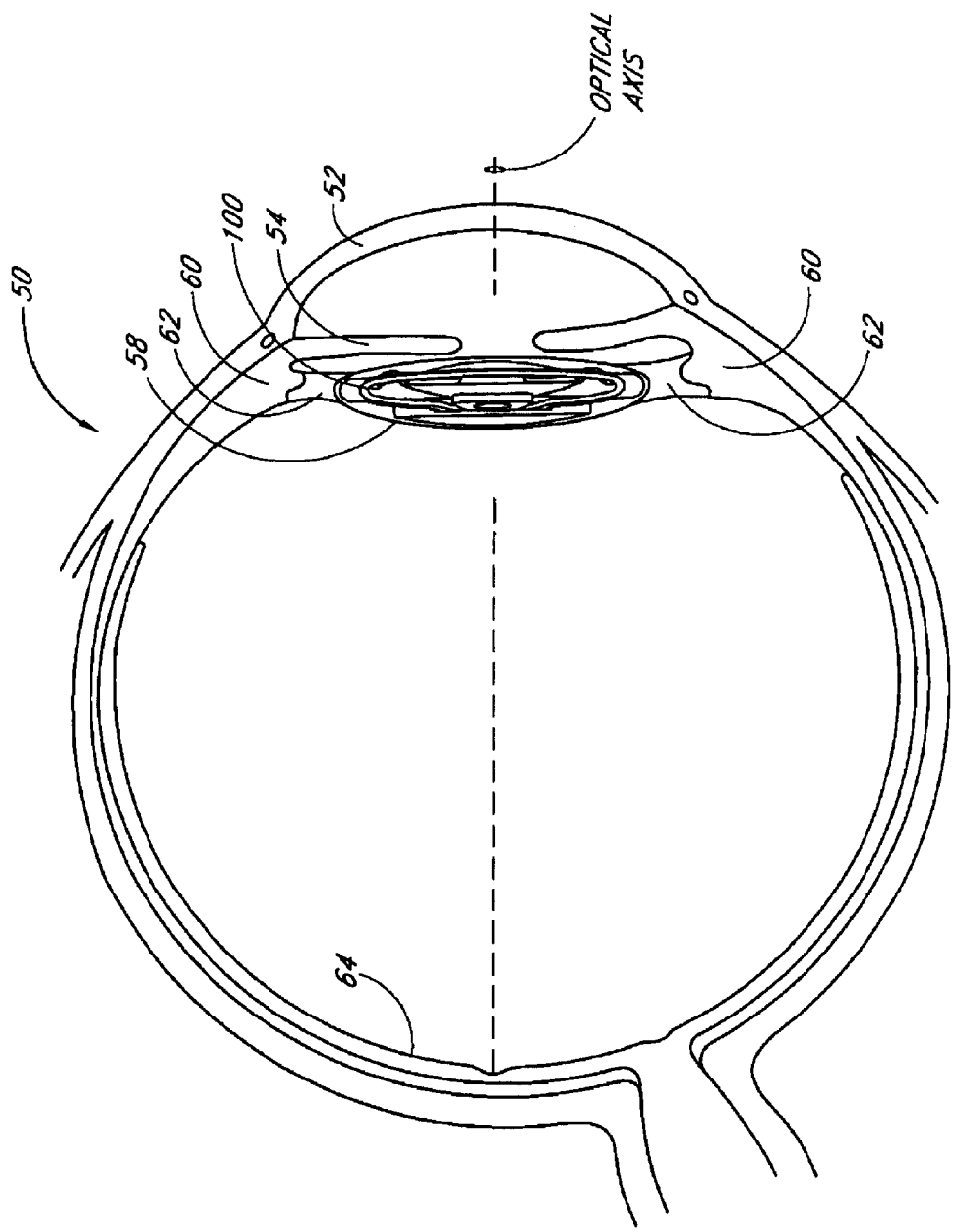
FIG. 17 is a sectional view of the human eye with the lens system implanted in the capsular bag and the lens system in the unaccommodated state.

FIGS. 17.1 and 17.2 show two preferred cross-sectional configurations which may be used along some or all of the length of the translation members and/or arms 110a, 110b, 114a, 114b, 122a, 122b, 124a, 124b. The shape is defined by a relatively broad and flat or slightly curved outer surface 182. It is intended that when in use the outer surface faces away from the interior of the lens system and/or toward the capsular bag 58. The remaining surfaces, proportions and dimensions making up the cross-sectional shape can vary widely but may advantageously be selected to facilitate manufacture of the lens system 100 via molding or casting techniques while minimizing stresses in the arms during use of the lens system.

FIG. 17.3 depicts a number of alternative cross-sectional configurations which are suitable for the translation members and/or arms 110a, 110b, 114a, 114b, 122a, 122b, 124a, 124b. As shown, a wide variety of cross-sectional shapes may be used, but preferably any shape includes the relatively broad and flat or slightly curved outer surface 182.

It is further contemplated that the dimensions, shapes, and/or proportions of the cross-sectional configuration of the translation members and/or arms 110a, 110b, 114a, 114b, 122a, 122b, 124a, 124b may vary along the length of the members/arms. This may be done in order to, for example, add strength to high-stress regions of the arms, fine-tune their spring characteristics, add rigidity or flexibility, etc.

As discussed above, each of the anterior viewing element 106 and the posterior viewing element 118 preferably comprises an optic having refractive power. In one preferred embodiment, the anterior viewing element 106 comprises a biconvex lens having positive refractive power and the posterior viewing element 118 comprises a convexo-concave lens having negative refractive power. The anterior viewing element 106 may comprise a lens having a positive power advantageously less than 55 diopters, preferably less than 40 diopters, more preferably less than 35 diopters, and most preferably less than 30 diopters. The posterior viewing element 118 may comprise a lens having a power which is advantageously between −25 and 0 diopters, and preferably between −25 and −15 diopters. In other embodiments, the posterior viewing element 118 comprises a lens having a power which is between −15 and 0 diopters, preferably between −13 and −2 diopters, and most preferably between −10 and −5 diopters. Advantageously, the total power of the optic(s) employed in the lens system 100 is about 5–35 diopters; preferably, the total power is about 10–30 diopters; most preferably, the total power is about 15–25 diopters. (As used herein, the term "diopter" refers to lens or system power as measured when the lens system 100 has been implanted in the human eye in the usual manner.) It should be noted that if materials having a high index of refraction (e.g., higher than that of silicone) are used, the optics may be made thinner which facilitates a wider range of motion for the optics. This in turn allows the use of lower-power optics than those specified above. In addition, higher-index materials allow the manufacture of a higher-power lens for a given lens thickness and thereby reduce the range of motion needed to achieve a given range of accommodation.

Some lens powers and radii of curvature presently preferred for use with an embodiment of the lens system 100 with optic(s) having a refractive index of about 1.432 are as follows: a +31 diopter, biconvex lens with an anterior radius of curvature of 5.944 mm and a posterior radius of curvature of 5.944 mm; a +28 diopter, biconvex lens with an anterior radius of curvature of 5.656 mm and a posterior radius of curvature of 7.788 mm; a +24 diopter, biconvex lens with an anterior radius of curvature of 6.961 mm and a posterior radius of curvature of 8.5 mm; a −10 diopter, biconcave lens with an anterior radius of curvature of 18.765 mm and a posterior radius of curvature of 18.765 mm; a −8 diopter, concavo-convex lens with an anterior radius of curvature of between 9 mm and 9.534 mm and a posterior radius of curvature of 40 mm; and a −5 diopter, concavo-convex lens with an anterior radius of curvature of between 9 mm and 9.534 mm and a posterior radius of curvature of 20 mm. In one embodiment, the anterior viewing element comprises the +31 diopter lens described above and the posterior viewing element comprises the −10 diopter lens described above. In another embodiment, the anterior viewing element comprises the +28 diopter lens described above and the posterior viewing element comprises the −8 diopter lens described above. In another embodiment, the anterior viewing element comprises the +24 diopter lens described above and the posterior viewing element comprises the −5 diopter lens described above.

The combinations of lens powers and radii of curvature specified herein advantageously minimize image magnification. However, other designs and radii of curvature provide modified magnification when desirable.

The lenses of the anterior viewing element 106 and the posterior viewing element 118 are relatively moveable as discussed above; advantageously, this movement is sufficient to produce an accommodation of at least one diopter, preferably at least two diopters and most preferably at least three diopters. In other words, the movement of the optics relative to each other and/or to the cornea is sufficient to create a difference between (i) the refractive power of the user's eye in the accommodated state and (ii) the refractive power of the user's eye in the unaccommodated state, having a magnitude expressed in diopters as specified above. Where the lens system 100 has a single optic, the movement of the optic relative to the cornea is sufficient to create a difference in focal power as specified above.

Advantageously, the lens system 100 can be customized for an individual patient's needs by shaping or adjusting only one of the four lens faces, and thereby altering the overall optical characteristics of the system 100. This in turn facilitates easy manufacture and maintenance of an inventory of lens systems with lens powers which will fit a large population of patients, without necessitating complex adjustment procedures at the time of implantation. It is contemplated that all of the lens systems in the inventory have a standard combination of lens powers, and that a system is fitted to a particular patient by simply shaping only a designated "variable" lens face. This custom-shaping procedure can be performed to-order at a central manufacturing facility or laboratory, or by a physician consulting with an individual patient. In one embodiment, the anterior face of the anterior viewing element is the designated sole variable lens face. In another embodiment, the anterior face of the posterior viewing element is the only variable face. However, any of the lens faces is suitable for such designation. The result is minimal inventory burden with respect to lens power (all of the lens systems in stock have the same lens powers) without requiring complex adjustment for individual patients (only one of the four lens faces is adjusted in the fitting process).

IV. THE LENS SYSTEM: ALTERNATIVE EMBODIMENTS

FIG. 17.4 depicts another embodiment of the lens system 100 in which the anterior viewing element 106 comprises an optic with a smaller diameter than the posterior viewing element 118, which comprises an optic with a peripheral positive-lens portion 170 surrounding a central negative portion 172. This arrangement enables the user of the lens system 100 to focus on objects at infinity, by allowing the (generally parallel) light rays incident upon the eye from an object at infinity to bypass the anterior viewing element 106. The peripheral positive-lens portion 170 of the posterior viewing element 118 can then function alone in refracting the light rays, providing the user with focused vision at infinity (in addition to the range of visual distances facilitated by the anterior and posterior viewing elements acting in concert). In another embodiment, the anterior viewing element 106 comprises an optic having a diameter of approximately 3 millimeters or less. In yet another embodiment, the anterior viewing element 106 comprises an optic having a diameter of approximately 3 millimeters or less and a refractive power of less than 55 diopters, more preferably less than 30 diopters. In still another embodiment, the peripheral positive-lens portion 170 has a refractive power of about 20 diopters.

FIG. 17.5 shows an alternative arrangement in which, the anterior viewing element 106 comprises an optic having a central portion 176 with refractive power, and a surrounding peripheral region 174 having a refractive power of substantially zero, wherein the central region 176 has a diameter smaller than the optic of the posterior viewing element 118, and preferably has a diameter of less than about 3 millimeters. This embodiment also allows some incident light rays to pass the anterior viewing element (though the zero-power peripheral region 174) without refraction, allowing the peripheral positive-lens portion 170 posterior viewing element 118 to function alone as described above.

Figure 18:
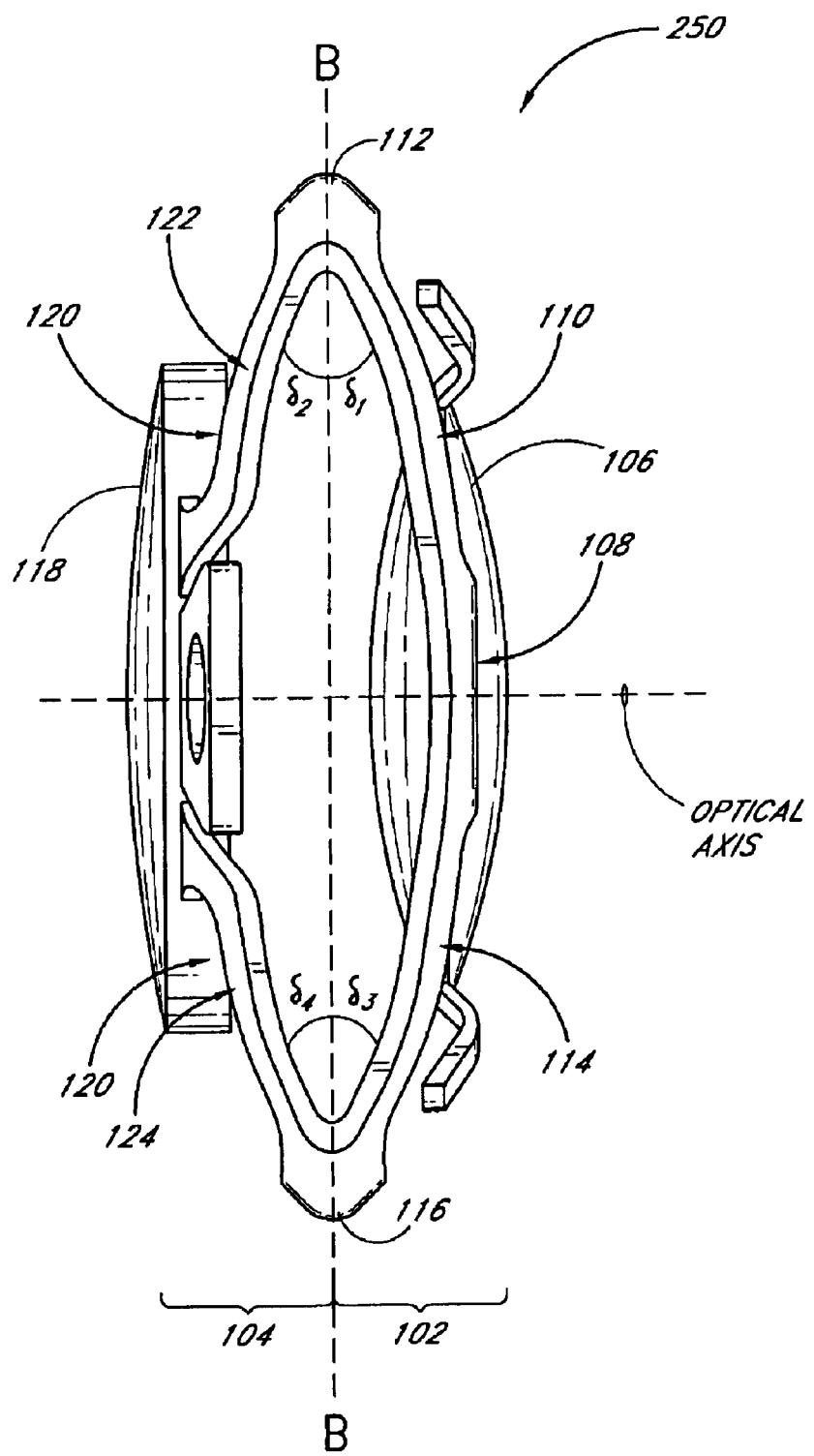
FIG. 18 is a side view of another embodiment of the lens system.
Figure 19:
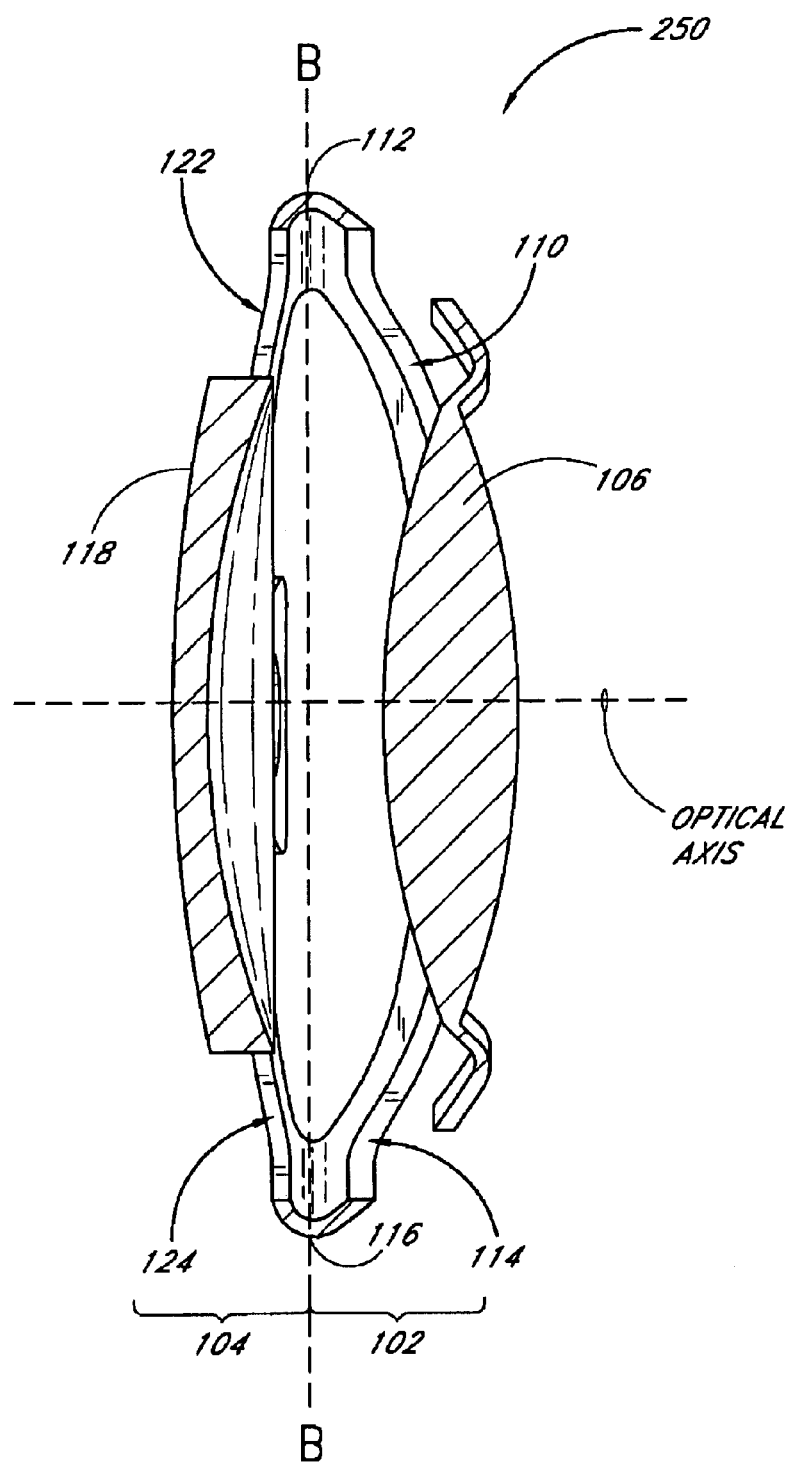
FIG. 19 is a side sectional view of another embodiment of the lens system.

FIGS. 18 and 19 depict another embodiment 250 of the intraocular lens. It is contemplated that, except as noted below, this embodiment 250 is largely similar to the embodiment disclosed in FIGS. 3–17. The lens 250 features an anterior biasing element 108 and posterior biasing element 120 which are arranged asymmetrically as the lens system 100 is viewed from the side. As used herein to describe the biasing elements 108, 120, "asymmetric" or "asymmetrically" means that, as the lens system 100 is viewed from the side, the first anterior translation member 110 and the first posterior translation member 122 extend from the first apex 112 at unequal first anterior and posterior biasing angles $\delta_1$, $\delta_2$ with respect to the line B—B (which represents the edge of a plane which is substantially orthogonal to the optical axis and intersects the first and second apices 112, 116) and/or that the second anterior translation member 114 and the second posterior translation member 124 extend from the second apex 116 at substantially equal second anterior and posterior biasing angles $\delta_3$, $\delta_4$ with respect to the line B—B.

In the embodiment shown in FIGS. 18–19, the first and second anterior biasing angles $\delta_1$, $\delta_3$ are greater than the corresponding first and second posterior biasing angles $\delta_2$, $\delta_4$. This arrangement advantageously maintains the posterior viewing element 118 and apices 112, 116 in a substantially stationary position. Consequently, the moving mass of the lens system 250 is reduced, and the anterior viewing element 106 can move more quickly over a wider range along the optical axis under a given motive force. (Note that even where the posterior biasing element 120 and its constituent first and second posterior translation members 122, 124 are substantially immobile, they are nonetheless "biasing elements" and "translation members" as those terms are used herein.) In another embodiment, the anterior biasing element 108 and posterior biasing element 120 are arranged asymmetrically in the opposite direction, i.e. such that the first and second anterior biasing angles $\delta_1$, $\delta_3$ are smaller than the corresponding first and second posterior biasing angles 62, 64. This arrangement also provides for a wider range of relative movement of the viewing elements, in comparison to a "symmetric" system.

It should be further noted that the viewing elements 106, 118 shown in FIGS. 18–19 are asymmetrically positioned in that the posterior viewing element 118 is closer to the line B—B than is the anterior viewing element 106. It has been found that this configuration yields desirable performance characteristics irrespective of the configuration of the biasing elements 108, 120. In alternative embodiments, the viewing elements 106, 118 may be positioned symmetrically with respect to the line B—B, or they may be positioned asymmetrically with the anterior viewing element 106 closer to the line B—B than the posterior viewing element 118 (see FIG. 4 wherein the line in question is denoted A—A). Furthermore, the symmetry or asymmetry of the biasing elements and viewing elements can be selected independently of each other.

Figure 20:
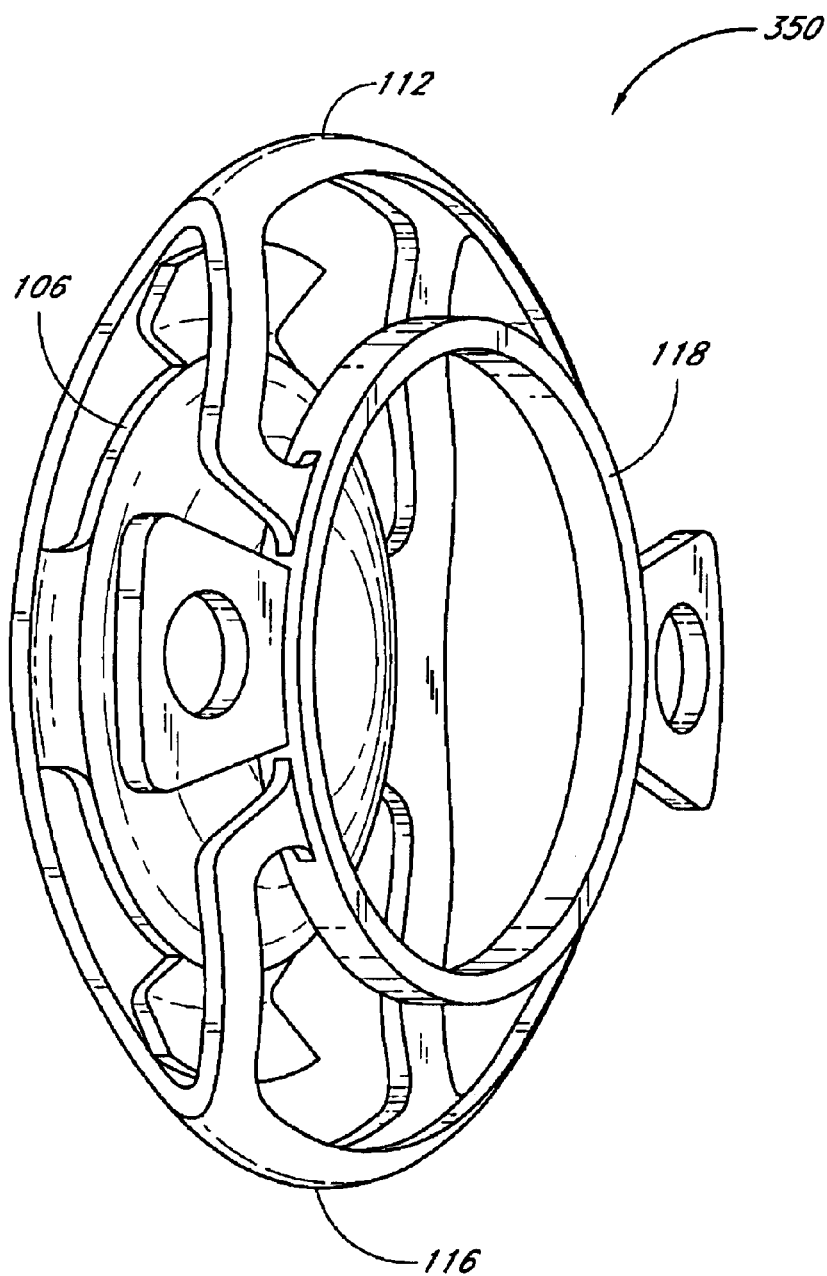
FIG. 20 is a rear perspective view of another embodiment of the lens system.

FIG. 20 shows another embodiment 350 of an intraocular lens in which the posterior viewing element 118 comprises an annular frame member defining a void therein, while the anterior viewing element 106 comprises an optic having refractive power. Alternatively, the posterior viewing element 118 could comprise a zero power lens or a simple transparent member. Likewise, in another embodiment the anterior viewing element 106 could comprise an annular frame member with a void therein or a simple zero power lens or transparent member, with the posterior viewing element 118 comprising an optic having refractive power. As a further alternative, one or both of the anterior and posterior viewing elements 106, 118 may comprise an annular or other perimeter frame member which can receive a removable optic (or a "one-time install" optic) with an interference type fit and/or subsequent adhesive or welding connections. Such a configuration facilitates assembly and/or fine-tuning of the lens system during an implantation procedure, as will be discussed in further detail below.

V. THE LENS SYSTEM: ADDITIONAL FEATURES

Figure 21:
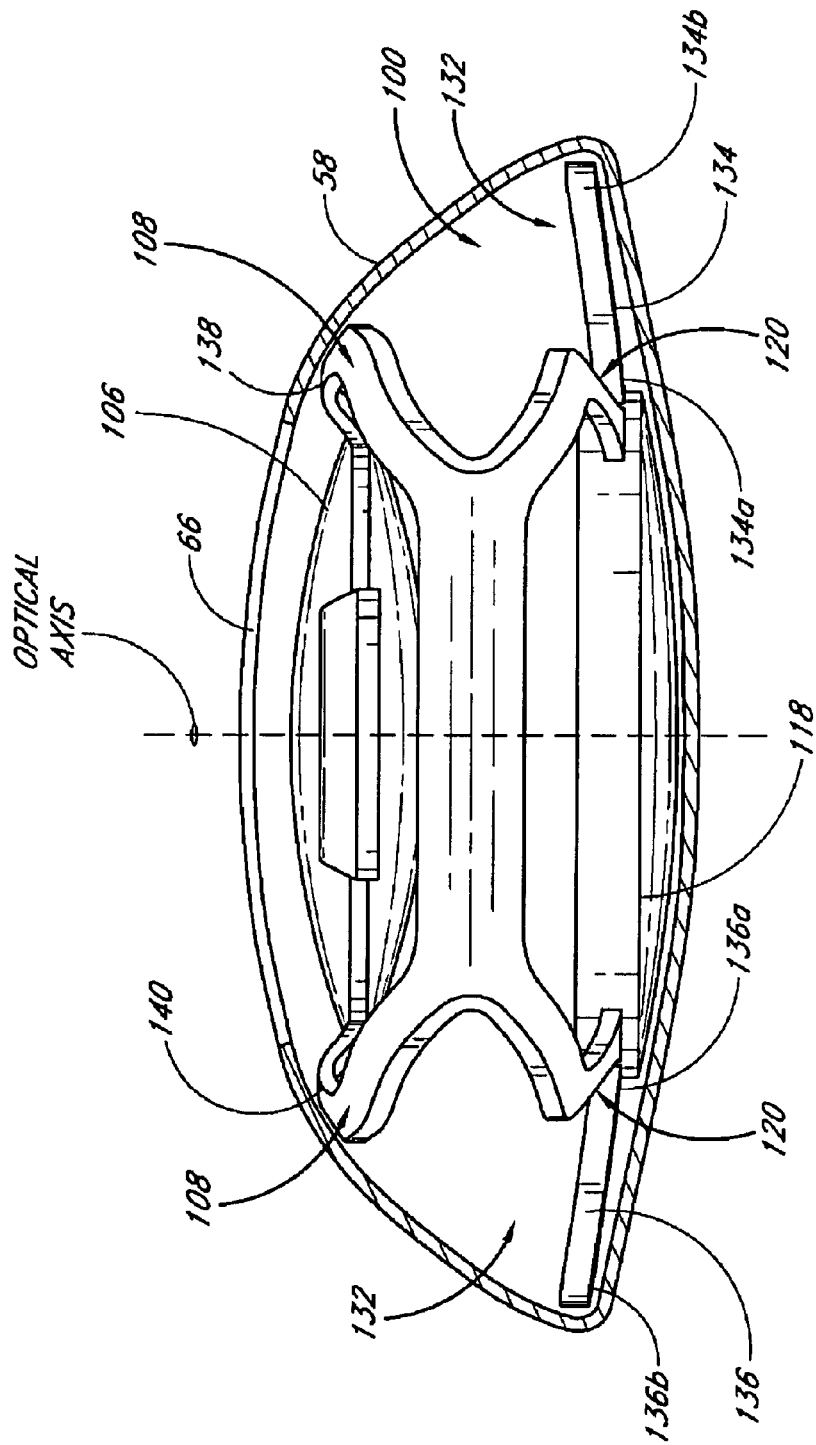
FIG. 21 is a partial top sectional view of another embodiment of the lens system, implanted in the capsular bag.

FIG. 21 depicts the function of the distending portion 132 in greater detail. The lens system 100 is shown situated in the capsular bag 58 in the customary manner with the anterior viewing element 106 and posterior viewing element 118 arranged along the optical axis. The capsular bag 58 is shown with a generally circular anterior opening 66 which may often be cut into the capsular bag during installation of the lens system 100. The first and second distending members 134, 136 of the distending portion 132 distend the capsular bag 58 so that intimate contact is created between the posterior face of the posterior viewing element and/or the posterior biasing element 120. In addition, intimate contact is facilitated between the anterior face of the anterior viewing element 106 and/or anterior biasing element 108. The distending members 134, 136 thus remove any slack from the capsular bag 58 and ensure optimum force coupling between the bag 58 and the lens system 100 as the bag 58 is alternately stretched and released by the action of the ciliary muscle.

Furthermore, the distending members 134, 136 reshape the capsular bag 58 into a taller, thinner configuration along its range of accommodation to provide a wider range of relative motion of the viewing elements 106, 118. When the capsular bag 58 is in the unaccommodated state, the distending members 134, 136 force the capsular bag into a thinner configuration (as measured along the optical axis) in comparison to the unaccommodated configuration of the capsular bag 58 with the natural lens in place. Preferably, the distending members 134, 136 cause the capsular bag 58 to taken on a shape in the unaccommodated state which is about 1.0–2.0 mm thinner, more preferably about 1.5 mm thinner, along the optical axis than it is with the natural lens in place and in the unaccommodated state.

With such a thin "starting point" provided by the distending members 134, 136, the viewing elements 106, 118 of the lens system can move a greater distance apart, and provide a greater range of accommodation, without causing undesirable contact between the lens system and the iris. Accordingly, by reshaping the bag as discussed above the distending members 134, 136 facilitate a range of relative motion of the anterior and posterior viewing elements 106, 118 of about 0.5–4 mm, preferably about 1–3 mm, more preferably about 1–2 mm, and most preferably about 1.5 mm.

The distending portion 132/distending members 134, 136 are preferably separate from the anterior and posterior biasing elements 108, 120; the distending members 134, 136 thus preferably play no part in biasing the anterior and posterior viewing elements 106, 118 apart toward the accommodated position. This arrangement is advantageous because the apices 112, 116 of the biasing elements 108, 120 reach their point of minimum protrusion from the optical axis (and thus the biasing elements reach their minimum potential effectiveness for radially distending the capsular bag) when the lens system 100 is in the accommodated state (see FIG. 16), which is precisely when the need is greatest for a taut capsular bag so as to provide immediate response to relaxation of the ciliary muscles. The preferred distending portion is "static" (as opposed to the "dynamic" biasing members 108, 120 which move while urging the viewing elements 106, 118 to the accommodated position or carrying the viewing elements to the unaccommodated position) in that its member(s) protrude a substantially constant distance from the optical axis throughout the range of motion of the viewing elements 106, 118. Although some degree of flexing may be observed in the distending members 134, 136, they are most effective when rigid. Furthermore, the thickness and/or cross-sectional profile of the distending members 134/136 may be varied over the length of the members as desired to provide a desired degree of rigidity thereto.

The distending portion 132/distending members 132, 134 advantageously reshape the capsular bag 58 by stretching the bag 58 radially away from the optical axis and causing the bag 58 to take on a thinner, taller shape throughout the range of accommodation by the eye. This reshaping is believed to facilitate a broad (as specified above) range of relative motion for the viewing elements of the lens system 100, with appropriate endpoints (derived from the total system thicknesses detailed above) to avoid the need for unacceptably thick optic(s) in the lens system.

If desired, the distending members 134, 136 may also function as haptics to stabilize and fixate the orientation of the lens system 100 within the capsular bag. The openings 134c, 136c of the preferred distending members 134,136 permit cellular ingrowth from the capsular bag upon positioning of the lens system 100 therein. Finally, other methodologies, such as a separate capsular tension ring or the use of adhesives to glue the capsular bag together in selected regions, may be used instead of or in addition to the distending portion 132, to reduce "slack" in the capsular bag.

A tension ring can also act as a physical barrier to cell growth on the inner surface of the capsular bag, and thus can provide additional benefits in limiting posterior capsule opacification, by preventing cellular growth from advancing posteriorly on the inner surface of the bag. When implanted, the tension ring firmly contacts the inner surface of the bag and defines a circumferential barrier against cell growth on the inner surface from one side of the barrier to another.

FIG. 21.1 shows an alternative configuration of the distending portion 132, in which the distending members 134, 136 comprise first and second arcuate portions which connect at either end to the apices 112, 116 to form therewith an integral perimeter member. In this arrangement it is preferred that the distending members and apices form an oval with height I smaller than width J.

FIG. 21.2 shows another alternative configuration of the distending portion 132, in which arcuate rim portions 137 interconnect the apices 112, 116 and the free ends 134b, 136b of the distending members 134, 136. Thus is formed an integral perimeter member with generally higher lateral rigidity than the arrangement depicted in FIG. 21.1.

FIG. 21.3 shows another alternative configuration of the distending portion 132, in which the distending members 134, 136 are integrally formed with the first and second posterior translation members 122, 124. The distending members 134, 136 and translation members 122, 124 thus form common transition members 139 which connect to the periphery of the posterior viewing element 118.

Figure 22:
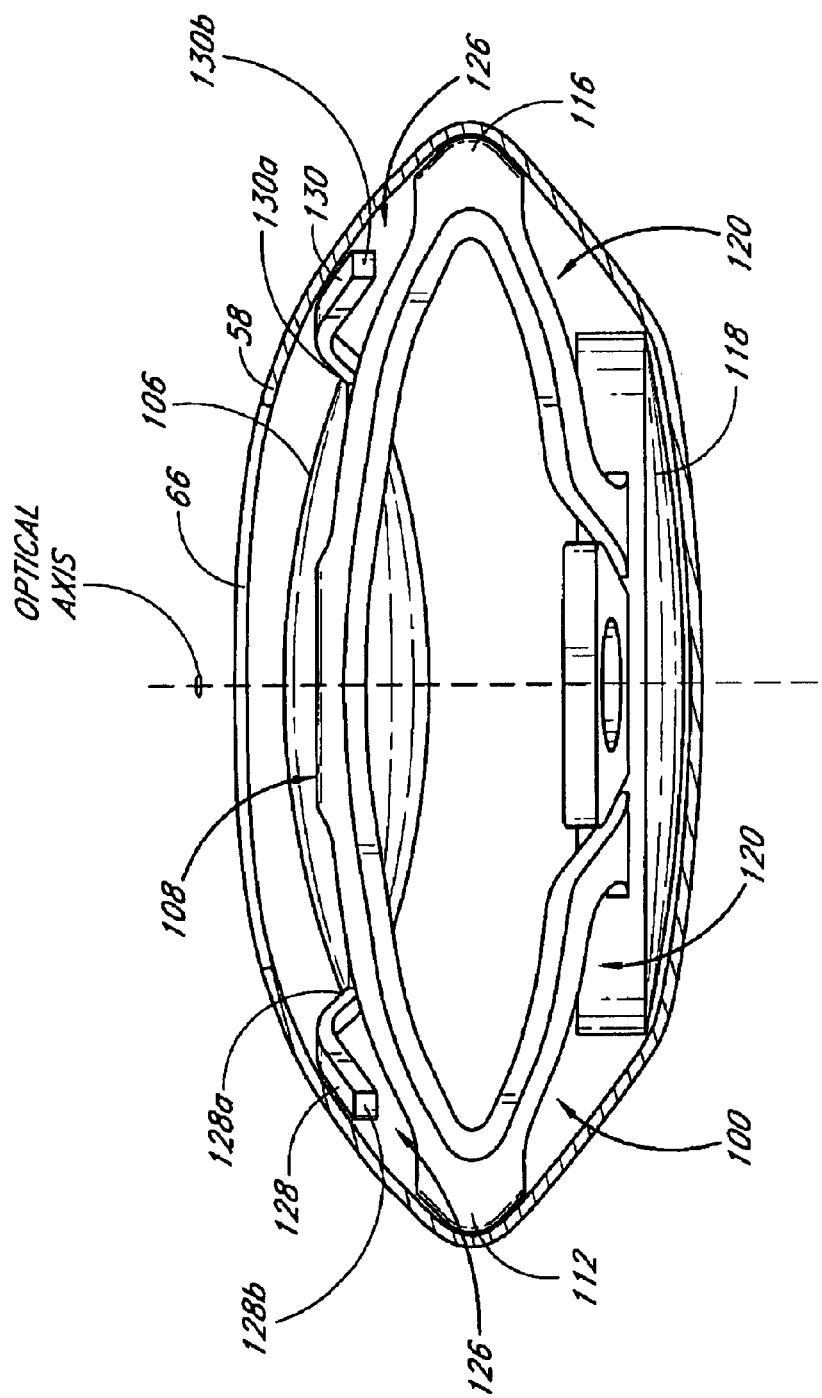
FIG. 22 is a partial side sectional view of another embodiment of the lens system, implanted in the capsular bag.
Figure 24:
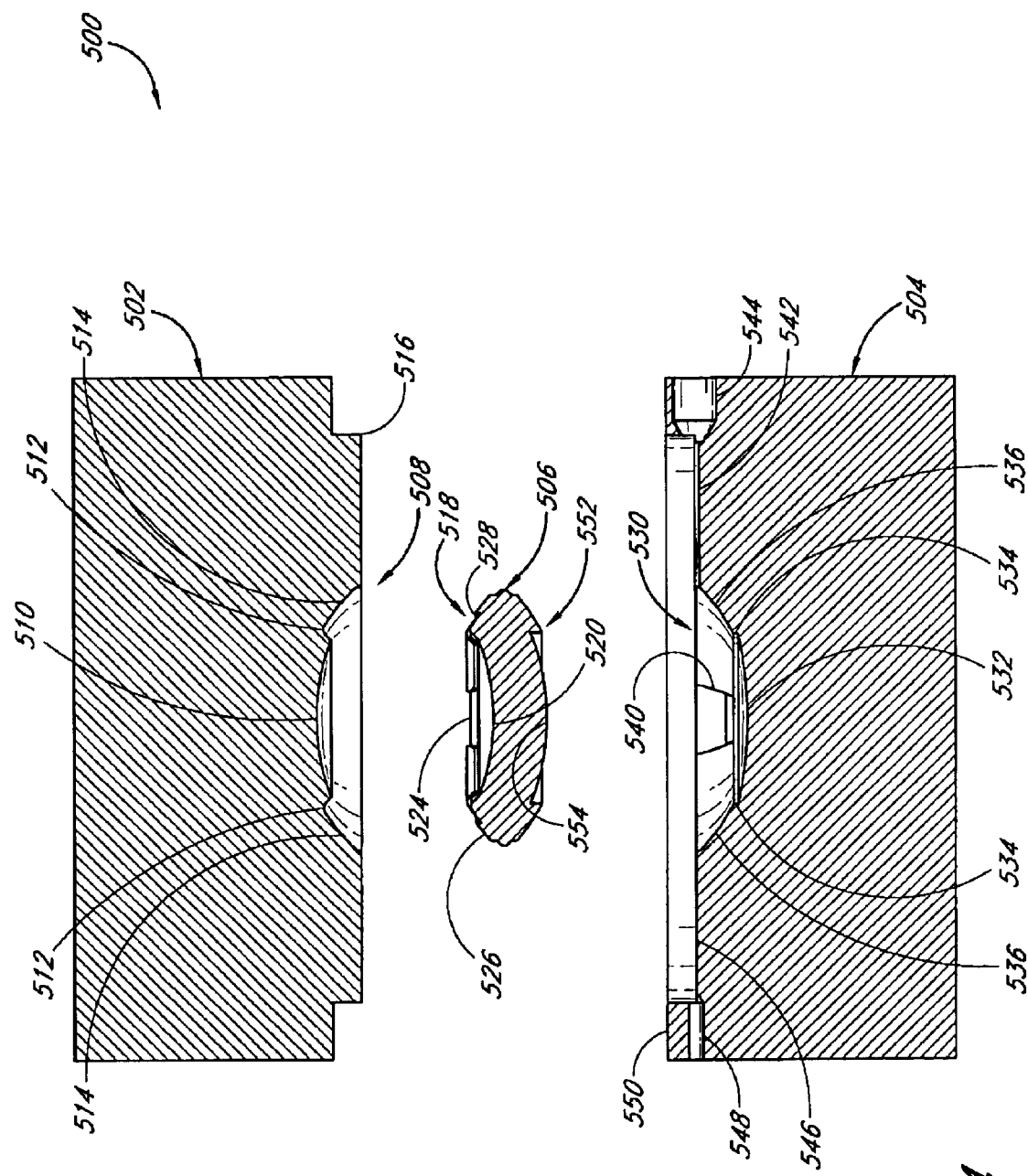
FIG. 24 is a side sectional view of the mold system.
Figure 25:
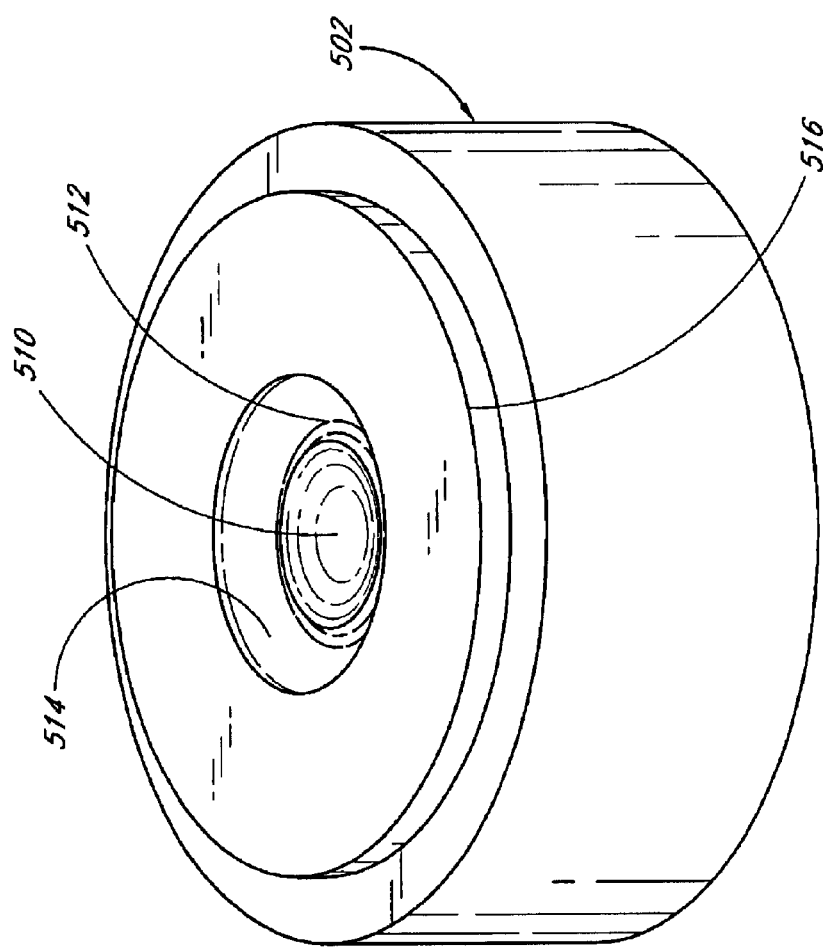
FIG. 25 is a perspective view of a first mold portion.
Figure 26:
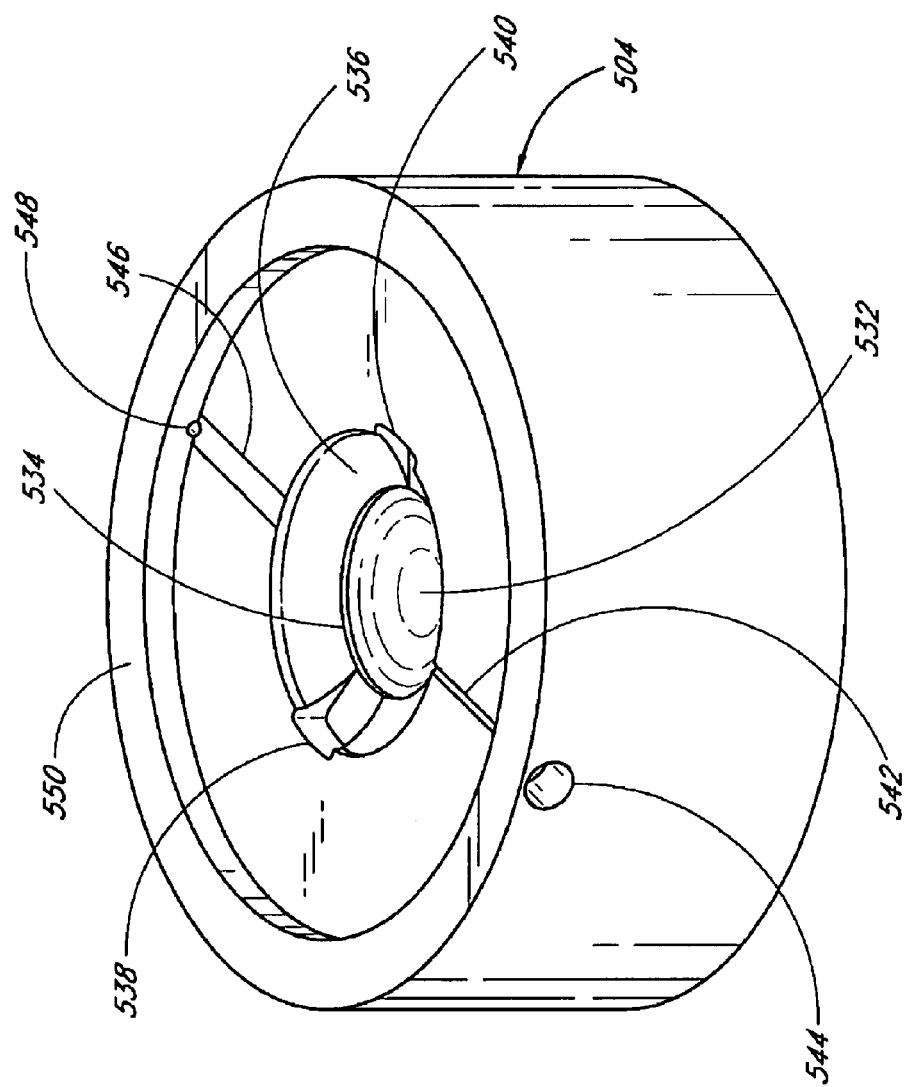
FIG. 26 is a perspective view of a second mold portion.
Figure 27:
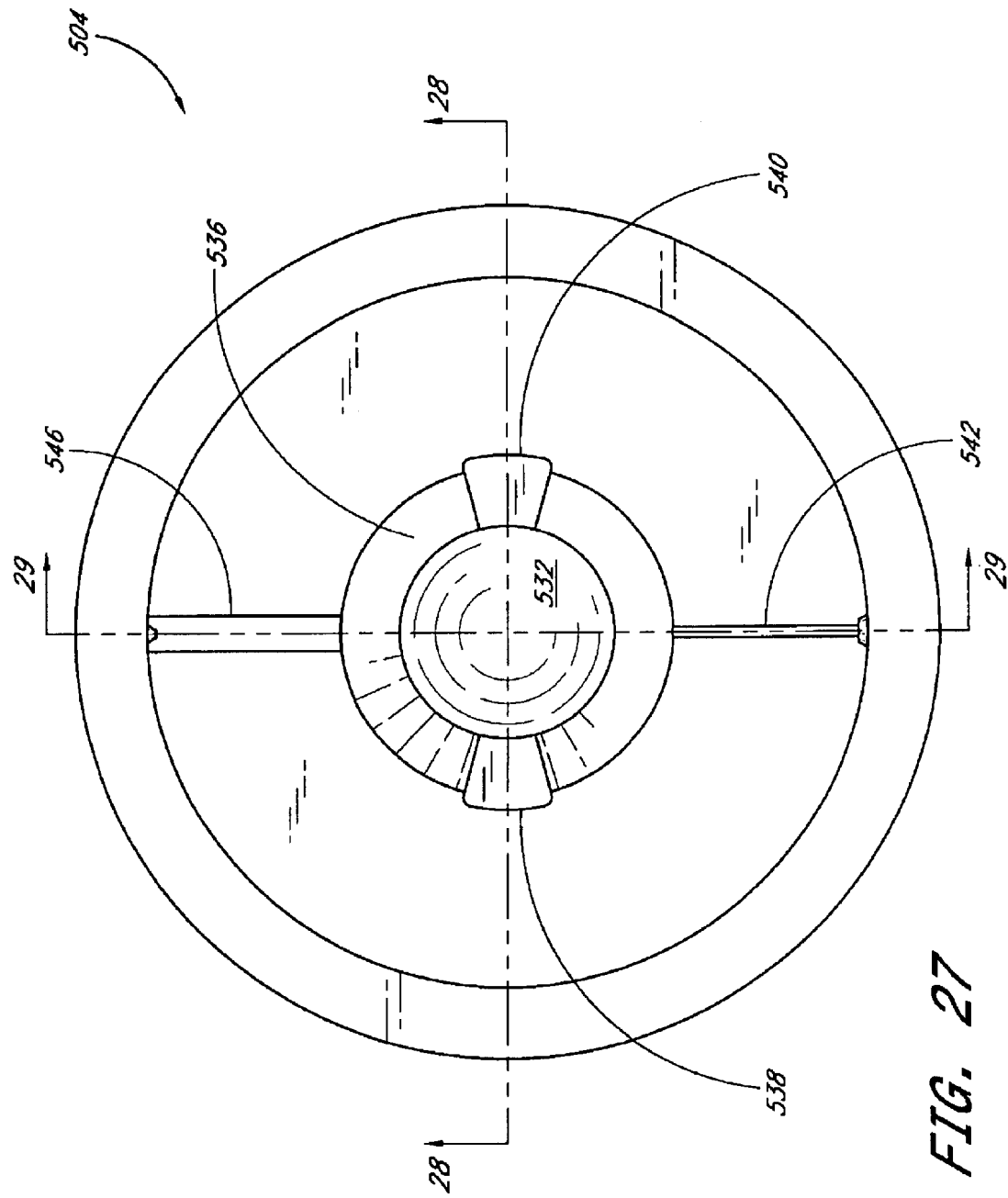
FIG. 27 is a top view of the second mold portion.
Figure 28:
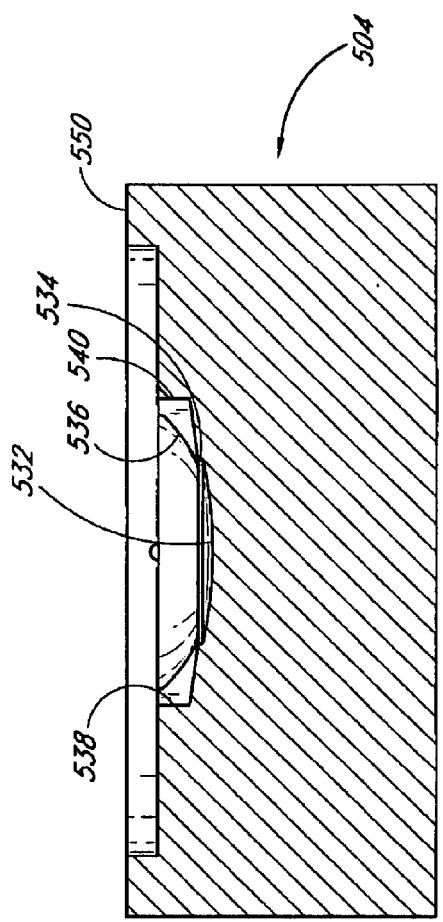
FIG. 28 is a side sectional view of the second mold portion.
Figure 29:
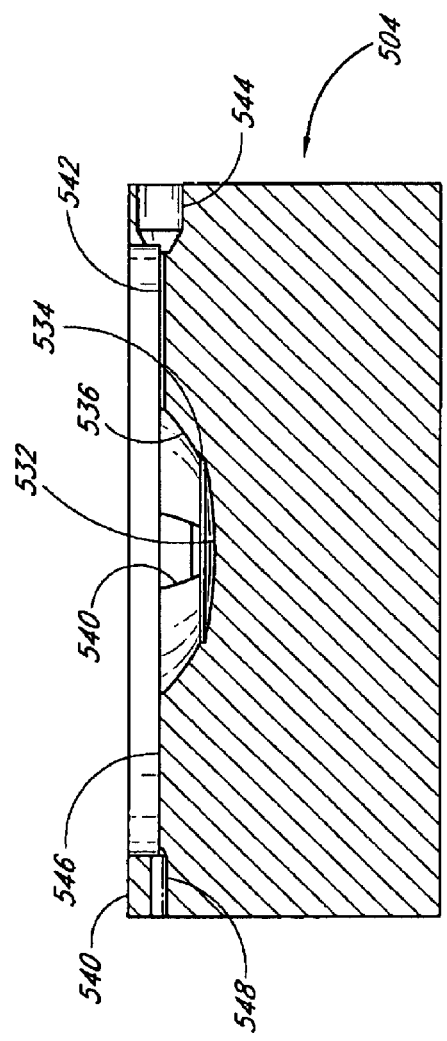
FIG. 29 is another side sectional view of the second mold portion.
Figure 30:
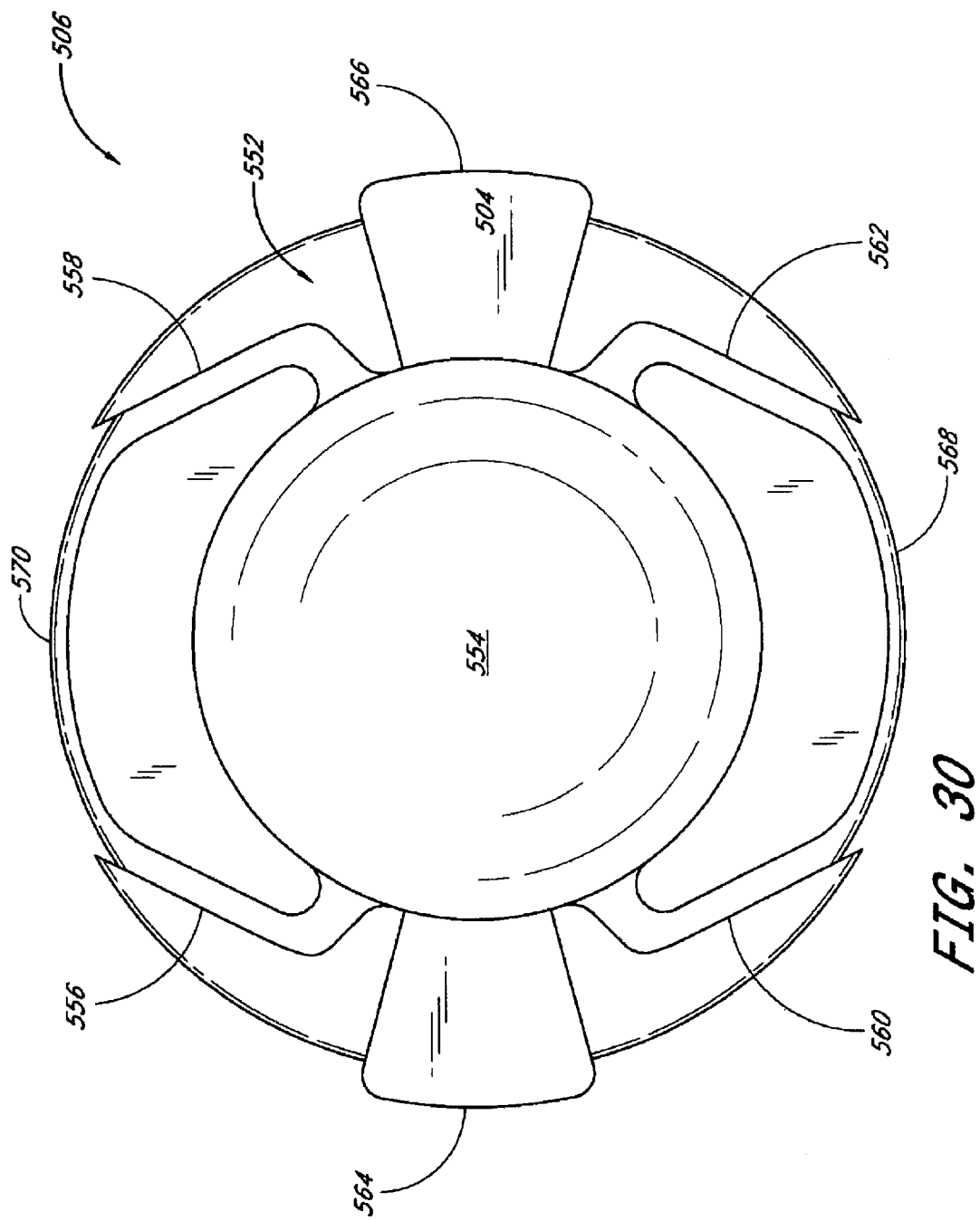
FIG. 30 is a bottom view of a center mold portion.
Figure 33:
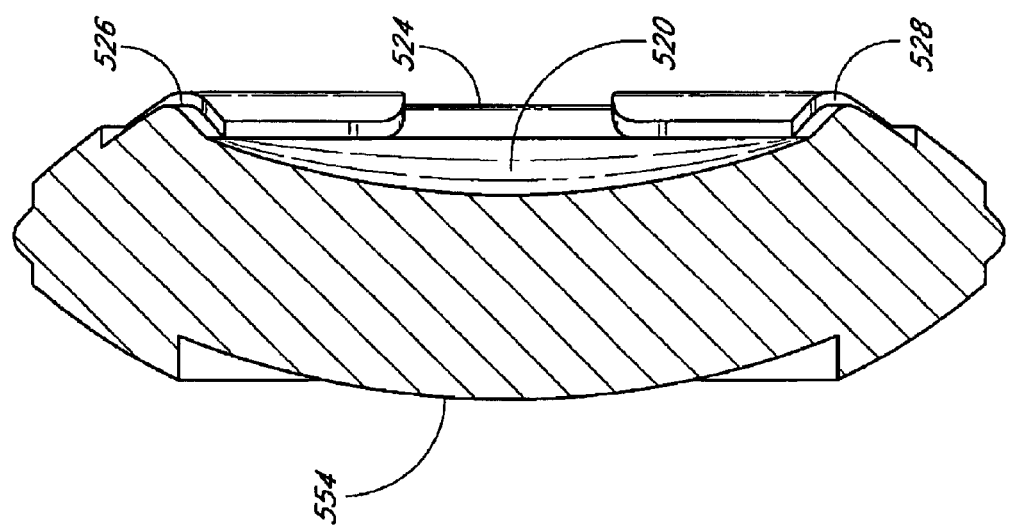
FIG. 33 is another sectional view of the center mold portion.
Figure 32:
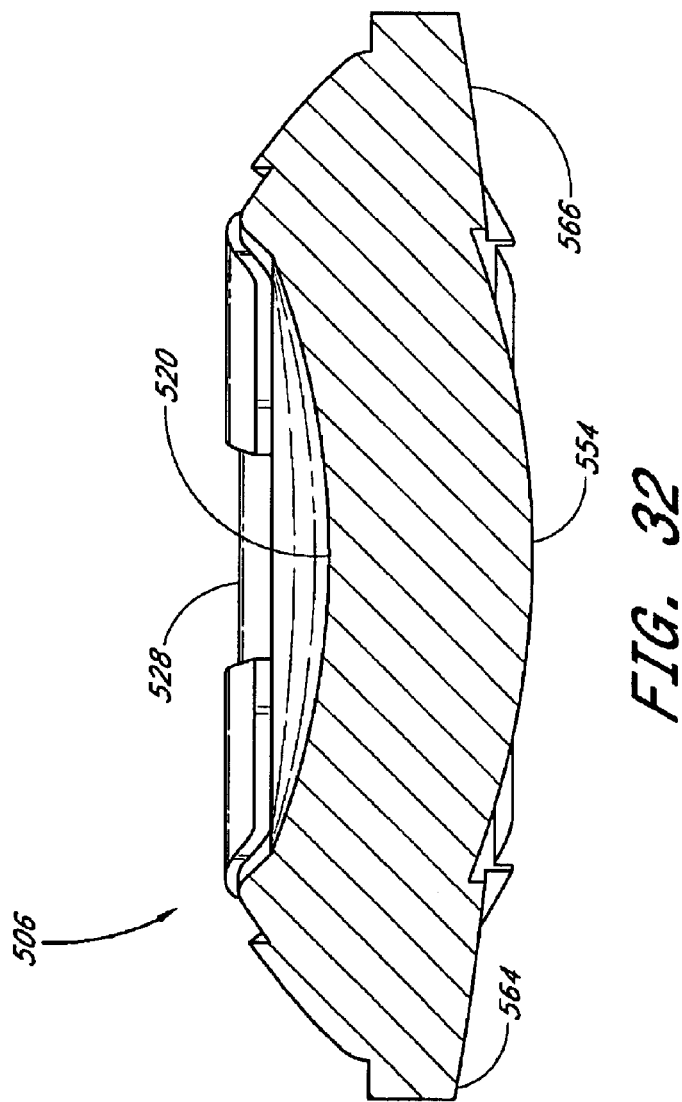
FIG. 32 is a sectional view of the center mold portion.

FIG. 22 shows the function of the retention portion 126 in greater detail. It is readily seen that the first and second retention members 128, 130 facilitate a broad contact base between the anterior portion of the lens system 100 and the anterior aspect of the capsular bag 58. By appropriately spacing the first and second retention members 128, 130, the members prevent extrusion of the anterior viewing element 106 through the anterior opening 66. It is also readily seen that where contact occurs between the anterior aspect of the capsular bag 58 and one or both of the retention members 128, 130, the retention members also participate in force coupling between the bag 58 and the lens system 100 as the bag is stretched and released by the action of the ciliary muscles.

As best seen in FIGS. 21 and 22, the anterior portion 102 of the lens system 100 forms a number of regions of contact with the capsular bag 58, around the perimeter of the anterior viewing element 106. In the illustrated embodiment, at least some of these regions of contact are located on the anteriormost portions of the anterior biasing element 108, specifically at the transition members 138, 140, and at the retention members 128, 130. The transition members and the retention members define spaces therebetween at the edges of the anterior viewing element 106 to permit fluid to flow between the interior of the capsular bag 58 and the portions of the eye anterior of the bag 58. In other words, the anterior portion of the lens system 100 includes at least one location which is spaced from and out of contact with the capsular bag 58 to provide a fluid flow channel extending from the region between the viewing elements 106, 118 to the exterior of the bag 58. Otherwise, if the anterior portion 102 of the lens system 100 seals the anterior opening 66 of the bag 58, the resulting prevention of fluid flow can cause the aqueous humor in the capsular bag to stagnate, leading to a clinically adverse event, and can inhibit the movement of the lens system 100 between the accommodated and unaccommodated states.

If desired, one or both of the retention members 128, 130 may have an opening 129 formed therein to permit fluid flow as discussed above. (See FIG. 21.1.)

The retention members 128, 130 and the transition members 138, 140 also prevent contact between the iris and the anterior viewing element 106, by separating the anterior opening 66 from the anterior face of the viewing element 106. In other words, the retention members 128, 130 and the transition members 138, 140 displace the anterior aspect of the capsular bag 58, including the anterior opening 66, anteriorly from the anterior viewing element 106, and maintain this separation throughout the range of accommodation of the lens system. Thus, if contact occurs between the iris and the lens system-capsular bag assembly, no part of the lens system will touch the iris, only the capsular bag itself, in particular those portions of the bag 58 overlying the retention members 128, 130 and/or the transition members 138, 140. The retention members 128, 130 and/or the transition members 138, 140 therefore maintain a separation between the iris and the lens system, which can be clinically adverse if the contacting portion(s) of the lens system are constructed from silicone.

As depicted in FIG. 22.1, one or more stop members 190 may be located where appropriate on the anterior and/or posterior biasing elements 108, 120 to limit the convergent motion of the anterior and posterior viewing elements 106, 118, and preferably prevent contact therebetween. As the lens system 100 moves toward the unaccommodated position, the stop member(s) located on the anterior biasing element 108 come into contact with the posterior biasing element 120 (or with additional stop member(s) located on thereon), and any stop member(s) located on the posterior biasing element 120 come into contact with the anterior biasing element 108 (or with additional stop member(s) located thereon). The stop members 190 thus define a point or state of maximum convergence (in other words, the unaccommodated state) of the lens system 100/viewing elements 106, 118. Such definition advantageously assists in setting one extreme of the range of focal lengths which the lens system may take on (in those lens systems which include two or more viewing elements having refractive power) and/or one extreme of the range of motion of the lens system 100.

The stop members 190 shown in FIG. 22.1 are located on the first and second anterior translation members 110, 114 of the anterior biasing element 108 and extend posteriorly therefrom. When the anterior and posterior viewing elements 106, 118 move together, one or more of the stop members 190 will contact the posterior translation member(s) 122, 124, thereby preventing further convergent motion of the viewing elements 106, 118. Of course, in other embodiments the stop member(s) 190 can be in any suitable location on the lens system 100.

VI. MOLD TOOLING

FIGS. 23–34 depict a mold system 500 which is suitable for molding the lens system 100 depicted in FIGS. 3–17. The mold system 500 generally comprises a first mold 502, a second mold 504 and a center mold 506. The center mold 506 is adapted to be positioned between the first mold 502 and the second mold 504 so as to define a mold space for injection molding or compression molding the lens system 100. The mold system 500 may be formed from suitable metals, high-impact-resistant plastics or a combination thereof, and can be produced by conventional machining techniques such as lathing or milling, or by laser or electrical-discharge machining. The mold surfaces can be finished or modified by sand blasting, etching or other texturing techniques.

The first mold 502 includes a first mold cavity 508 with a first anterior mold face 510 surrounded by an annular trough 512 and a first perimeter mold face 514. The first mold 502 also includes a projection 516 which facilitates easier mating with the second mold 504.

The center mold 506 includes a first center mold cavity 518 which cooperates with the first mold cavity 508 to define a mold space for forming the anterior portion 102 of the lens system 100. The first center mold cavity 518 includes a central anterior mold face 520 which, upon placement of the center mold 506 in the first mold cavity 508, cooperates with the first anterior mold face 510 to define a mold space for the anterior viewing element 106. In so doing, the first anterior mold face 510 defines the anterior face of the anterior viewing element 106 and the central anterior mold face 520 defines the posterior face of the anterior viewing element 106. In fluid communication with the chamber formed by the first anterior mold face 510 and the central anterior mold face 520 are lateral channels 522, 524 (best seen in FIG. 31) which form spaces for molding the first and second transition members 138, 140, along with the arms 110a, 110b of the first anterior translation member 110 as well as the arms 114a, 114b of the second anterior translation member 114. The first center mold cavity 518 also includes retention member cavities 526, 528 which define spaces for molding the first and second retention members 128, 130 to the anterior viewing element 106.

The second mold 504 includes a second mold cavity 530 with a second posterior mold space 532, a generally cylindrical transition 534 extending therefrom and connecting to a second perimeter mold face 536. Lateral notches 538, 540 (best seen in FIGS. 26 and 27) are formed in the second perimeter mold face 536. The second mold 504 also includes an input channel 542 connected to an input channel opening 544 for introducing material into the mold system 500. Also formed in the second mold 504 is an output channel 546 and an output channel opening 548. A generally cylindrical rim 550 is included for mating with the projection 516 of the first mold 502.

The center mold 506 includes a second center mold cavity 552 which cooperates with the second mold cavity 530 to define a mold space for the posterior portion 104 of the lens system 100. The second center mold cavity 552 includes a central posterior mold face 554 which, upon placement of the center mold 506 in engagement with the second mold cavity 530, cooperates with the second posterior mold face 532 and the transition 534 to define a chamber for forming the posterior viewing element 118. In fluid communication with the chamber formed by the central posterior mold face 554 and the second posterior mold face 532 are lateral channels 556, 558, 560, 562 which provide a mold space for forming the arms 122a, 122b of the first posterior translation member 122 and the arms 124a, 124b of the second posterior translation member 124. The second center mold cavity 552 includes lateral projections 564, 566 which coact with the notches 538, 540 formed in the second mold cavity 530. The chambers formed therebetween are in fluid communication with the chamber defined by the central posterior mold face 554 and the second posterior mold face 532 to form the first and second distending members 134, 136 integrally with the posterior viewing element 118.

The center mold 506 includes a first reduced-diameter portion 568 and a second reduced-diameter portion 570 each of which, upon assembly of the mold system 500, defines a mold space for the apices 112, 116 of the lens system 100.

In use, the mold system 500 is assembled with the center mold 506 positioned between the first mold 502 and the second mold 504. Once placed in this configuration, the mold system 500 is held together under force by appropriate techniques, and lens material is introduced into the mold system 500 via the input channel 542. The lens material then fills the space defined by the first mold 502, second mold 504, and the center mold 506 to take on the shape of the finished lens system 100.

In another embodiment, the lens system 100 or a portion thereof is formed by a casting or liquid-casting procedure in which one of the first or second molds is first filled with a liquid and the center mold is placed then into engagement with the liquid-filled mold. The exposed face of the center mold is then filled with liquid and the other of the first and second molds is placed into engagement with the rest of the mold system. The liquid is allowed or caused to set/cure and a finished casting may then removed from the mold system.

The mold system 500 can advantageously be employed to produce a lens system 100 as a single, integral unit. Alternatively, various portions of the lens system 100 can be separately molded, casted, machined, etc. and subsequently assembled to create a finished lens system. Assembly can be performed as a part of centralized manufacturing operations; alternatively, a physician can perform some or all of the assembly before or during the implantation procedure, to select lens powers, biasing members, system sizes, etc. which are appropriate for a particular patient.

The center mold 506 is depicted as comprising an integral unit with first and second center mold cavities 518, 552. Alternatively, the center mold 506 may have a modular configuration whereby the first and second mold cavities 518, 552 may be interchangeable to adapt the center mold 506 for manufacturing a lens system 100 according to a desired prescription or specification, or to otherwise change the power(s) of the lenses made with the mold. In this manner the manufacture of a wide variety of prescriptions may be facilitated by a set of mold cavities which can be assembled back-to-back or to opposing sides of a main mold structure.

VII. MATERIALS/SURFACE TREATMENTS

Preferred materials for forming the lens system 100 include silicone, acrylics, polymethylmethacrylate (PMMA), block copolymers of styrene-ethylene-butylene-styrene (C-FLEX) or other styrene-base copolymers, polyvinyl alcohol (PVA), polyurethanes, hydrogels or any other suitable polymers or monomers. In addition, any portion of the lens system 100 other than the optic(s) may be formed from stainless steel or a shape-memory alloy such as nitinol or any iron-based shape-memory alloy. Metallic components may be coated with gold to increase biocompatibility. Where feasible, material of a lower Shore A hardness such as 15A may be used for the optic(s), and material of higher hardness such as 35A may be used for the balance of the lens system 100. Finally, the optic(s) may be formed from a photosensitive silicone to facilitate post-implantation power adjustment as taught in U.S. patent application Ser. No. 09/416,044, filed Oct. 8, 1999, titled LENSES CAPABLE OF POST-FABRICATION POWER MODIFICATION, the entire contents of which are hereby incorporated by reference herein.

Methyl-methylacrylate monomers may also be blended with any of the non-metallic materials discussed above, to increase the lubricity of the resulting lens system (making the lens system easier to fold or roll for insertion, as discussed further below). The addition of methyl-methylacrylate monomers also increases the strength and transparency of the lens system.

The optics and/or the balance of the lens system 100 can also be formed from layers of differing materials. The layers may be arranged in a simple sandwich fashion, or concentrically. In addition, the layers may include a series of polymer layers, a mix of polymer and metallic layers, or a mix of polymer and monomer layers. In particular, a nitinol ribbon core with a surrounding silicone jacket may be used for any portion of the lens system 100 except for the optics; an acrylic-over-silicone laminate may be employed for the optics. A layered construction may be obtained by pressing/bonding two or more layers together, or deposition or coating processes may be employed.

In one embodiment, portions of the lens system 100 other than the optic(s) are formed from a shape-memory alloy. This embodiment takes advantage of the exceptional mechanical properties of shape-memory alloys and provides fast, consistent, highly responsive movement of the optic(s) within the capsular bag while minimizing material fatigue in the lens system 100. In one embodiment, one or both of the biasing elements 108, 120 are formed from a shape-memory alloy such as nitinol or any iron-based shape-memory alloy. Due to the flat stress-strain curve of nitinol, such biasing elements provide a highly consistent accommodation force over a wide range of displacement. Furthermore, biasing elements formed from a shape-memory alloy, especially nitinol, retain their spring properties when exposed to heat (as occurs upon implantation into a human eye) while polymeric biasing elements tend to lose their spring properties, thus detracting from the responsiveness of the lens system. For similar reasons, it is advantageous to use shape-memory alloys such as those discussed above in forming any portion of a conventional (non-accommodating) intraocular lens, other than the optic.

Where desired, various coatings are suitable for components of the lens system 100. A heparin coating may be applied to appropriate locations on the lens system 100 to prevent inflammatory cell attachment (ICA) and/or posterior capsule opacification (PCO); naturally, possible locations for such a coating include the posterior biasing element 120 and the posterior face of the posterior viewing element 118. Coatings can also be applied to the lens system 100 to improve biocompatibility; such coatings include "active"

coatings like P-15 peptides or RGD peptides, and "passive" coatings such as heparin and other mucopolysaccharides, collagen, fibronectin and laminin. Other coatings, including hirudin, teflon, teflon-like coatings, PVDF, fluorinated polymers, and other coatings which are inert relative to the capsular bag may be employed to increase lubricity at locations (such as the optics and distending members) on the lens system which contact the bag, or Hema or silicone can be used to impart hydrophilic or hydrophobic properties to the lens system 100.

It is also desirable subject the lens system 100 and/or the mold surfaces to a surface passivation process to improve biocompatibility. This may be done via conventional techniques such as chemical etching or plasma treatment.

Furthermore, appropriate surfaces (such as the outer edges/surfaces of the viewing elements, biasing elements, distending members, retention members, etc.) of the lens system 100 can be textured or roughened to improve adhesion to the capsular bag. This may be accomplished by using conventional procedures such as plasma treatment, etching, dipping, vapor deposition, mold surface modification, etc. As a further means of preventing ICA/PCO, a posteriorly-extending perimeter wall (not shown) may be added to the posterior viewing element 118 so as to surround the posterior face of the posterior optic. The wall firmly engages the posterior aspect of the capsular bag and acts as a physical barrier to the progress of cellular ingrowth occurring on the interior surface of the capsular bag. Finally, the relatively thick cross-section of the preferred anterior viewing element 118 (see FIGS. 9, 10) ensures that it will firmly abut the posterior capsule with no localized flexing. Thus, with its relatively sharp rim, the posterior face of the preferred posterior viewing element 118 can itself serve as a barrier to cellular ingrowth and ICA/PCO. In order to achieve this effect, the posterior viewing element 118 is preferably made thicker than conventional intraocular lenses. As an alternative or supplement to a thick posterior viewing element, cell growth may be inhibited by forming a pronounced, posteriorly-extending perimeter rim on the posterior face of the posterior viewing element 118. Upon implantation of the lens system 100, the rim firmly abuts the inner surface of the capsular bag 58 and acts as a physical barrier to cell growth between the posterior face of the posterior viewing element 118 and the capsular bag 58.

The selected material and lens configuration should be able to withstand secondary operations after molding/casting such as polishing, cleaning and sterilization processes involving the use of an autoclave, or ethylene oxide or radiation. After the mold is opened, the lens should undergo deflashing, polishing and cleaning operations, which typically involve a chemical or mechanical process, or a combination thereof. Suitable mechanical processes include tumbling, shaking and vibration; a tumbling process may involve the use of a barrel with varying grades of glass beads, fluids such as alcohol or water and polishing compounds such as aluminum oxides. Process rates are material dependent; for example, a tumbling process for silicone should utilize a 6" diameter barrel moving at 30–100 RPM. It is contemplated that several different steps of polishing and cleaning may be employed before the final surface quality is achieved.

Figure 34:
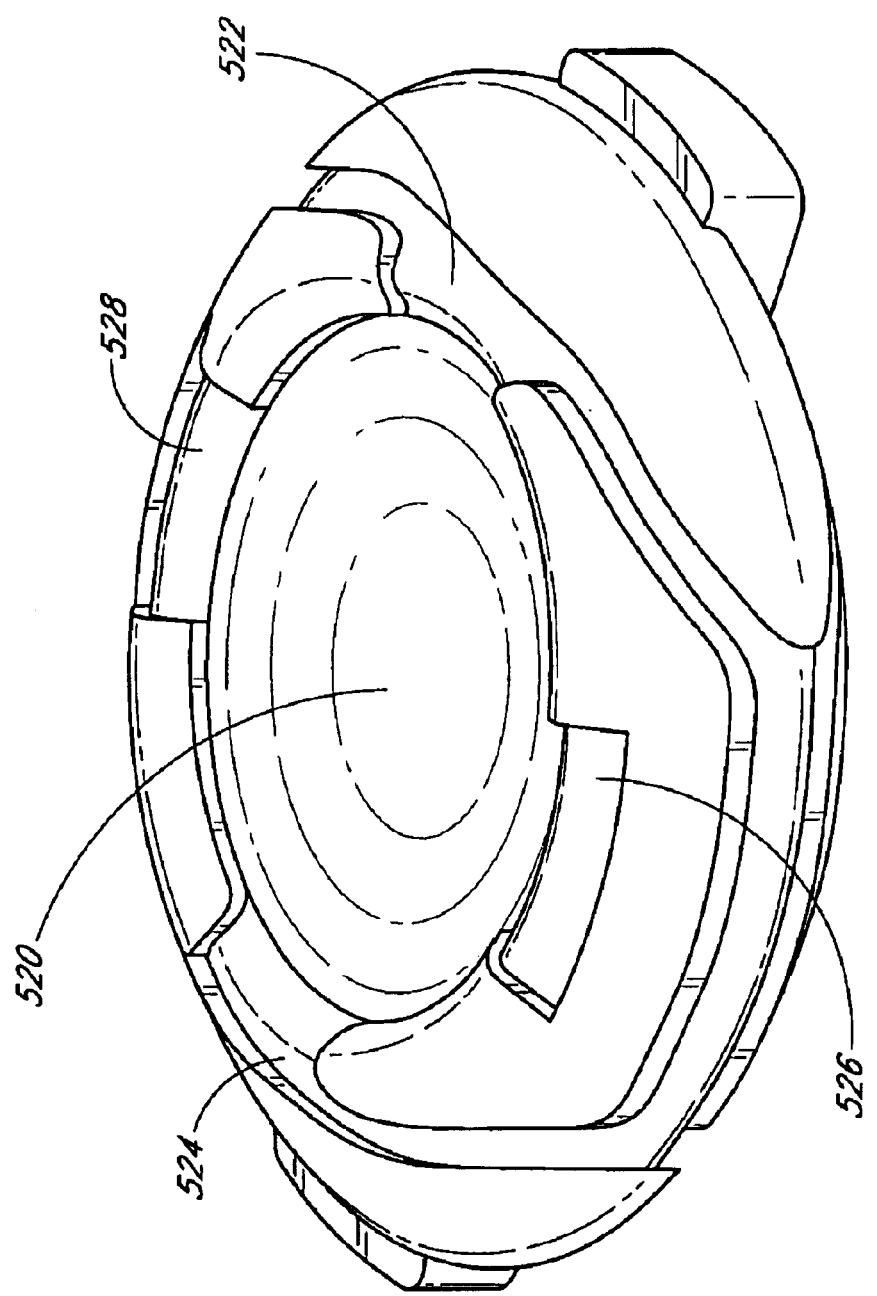
FIG. 34 is a perspective view of the center mold portion.

In one embodiment, the lens system 100 is held in a fixture to provide increased separation between, and improved process effect on, the anterior and posterior viewing elements during the deflashing/polishing/cleaning operations. In another embodiment, the lens system 100 is everted or turned "inside-out" so that the inner faces of the viewing elements are better exposed during a portion of the deflashing/polishing/cleaning. FIG. 34.1 shows a number of expansion grooves 192 which may be formed in the underside of the apices 112, 116 of the lens system 100 to facilitate eversion of the lens system 100 without damaging or tearing the apices or the anterior/posterior biasing elements 108, 120. For the same reasons similar expansion grooves may be formed on the opposite sides (i.e., the outer surfaces) of the apices 112, 116 instead of or in addition to the location of grooves on the underside.

A curing process may also be desirable in manufacturing the lens system 100. If the lens system is produced from silicone entirely at room temperature, the curing time can be as long as several days. If the mold is maintained at about 50 degrees C., the curing time is reduced to about 24 hours; if the mold is preheated to 100–200 degrees C. the curing time can be as short as about 3–15 minutes. Of course, the time-temperature combinations vary for other materials.

VIII. MULTIPLE-PIECE AND OTHER EMBODIMENTS

Figure 35:
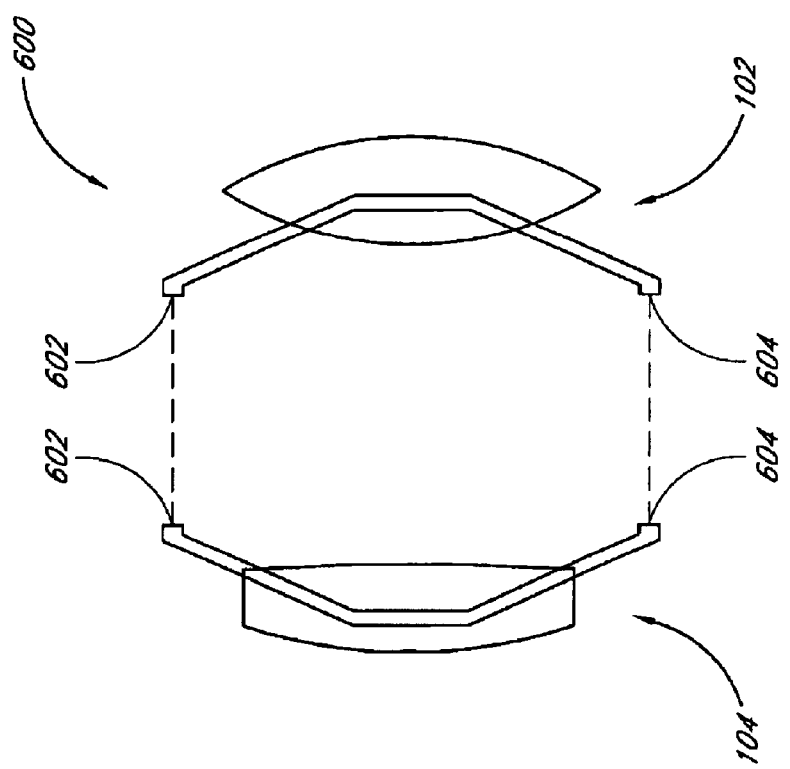
FIG. 35 is a schematic view of another embodiment of the lens system.

FIG. 35 is a schematic view of a two-piece embodiment 600 of the lens system. In this embodiment the anterior portion 102 and the posterior portion 104 are formed as separate pieces which are intended for separate insertion into the capsular bag and subsequent assembly therein. In one embodiment, each of the anterior and posterior portions 102, 104 is rolled or folded before insertion into the capsular bag. (The insertion procedure is discussed in further detail below.) The anterior portion 102 and posterior portion 104 are represented schematically as they may generally comprise any anterior-portion or posterior-portion structure disclosed herein; for example, they may simply comprise the lens system 100 shown in FIGS. 3–17, bisected along the line/plane A—A shown in FIG. 4. The anterior portion 102 and posterior portion 104 of the two-piece lens system 600 will include first and second abutments 602, 604 which are intended to be placed in abutting relation (thus forming the first and second apices of the lens system) during the assembly procedure. The first and second abutments 602, 604 may include engagement members (not shown), such as matching projections and recesses, to facilitate alignment and assembly of the anterior and posterior portions 102, 104.

As a further alternative, the anterior and posterior portions 102, 104 of the lens system 600 may be hingedly connected at one of the abutments 602, 604 and unconnected at the other, to allow sequential (but nonetheless partially assembled) insertion of the portions 102, 104 into the capsular bag. The individual portions may be separately rolled or folded before insertion. The two portions 102, 104 are "swung" together and joined at the unconnected abutment to form the finished lens system after both portions have been inserted and allowed to unfold/unroll as needed.

Figure 36:
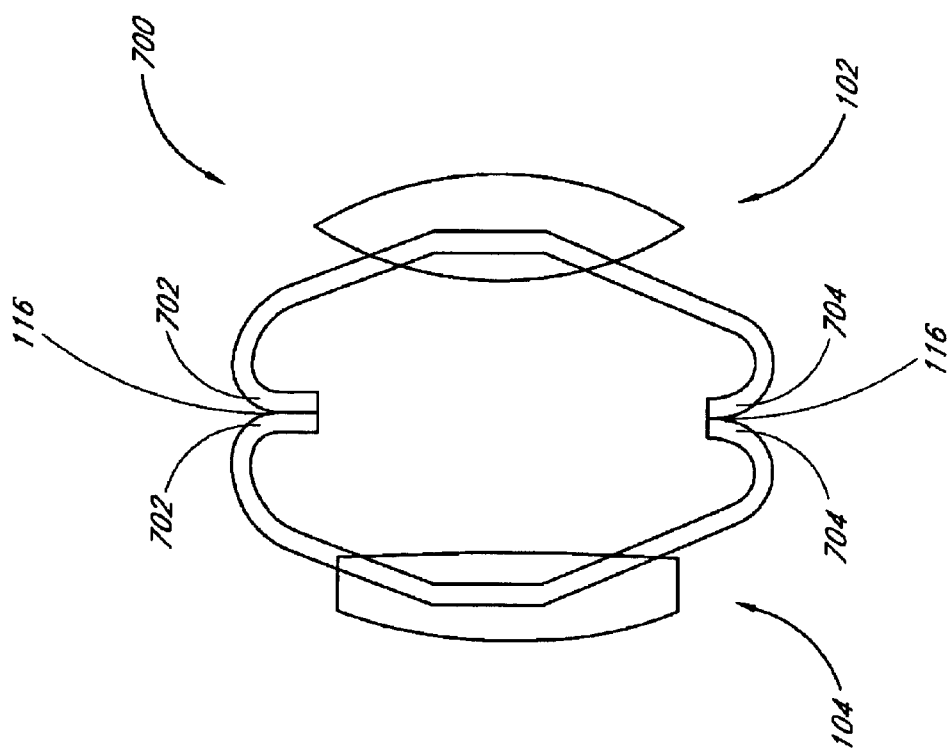
FIG. 36 is a schematic view of another embodiment of the lens system.

FIG. 36 depicts schematically another embodiment 700 of a two-piece lens system. The lens system 700 is desirably similar to the lens system 600 shown in FIG. 35, except for the formation of relatively larger, curled abutments 702, 704 which are assembled to form the apices 112, 116 of the system 700.

Figure 38:
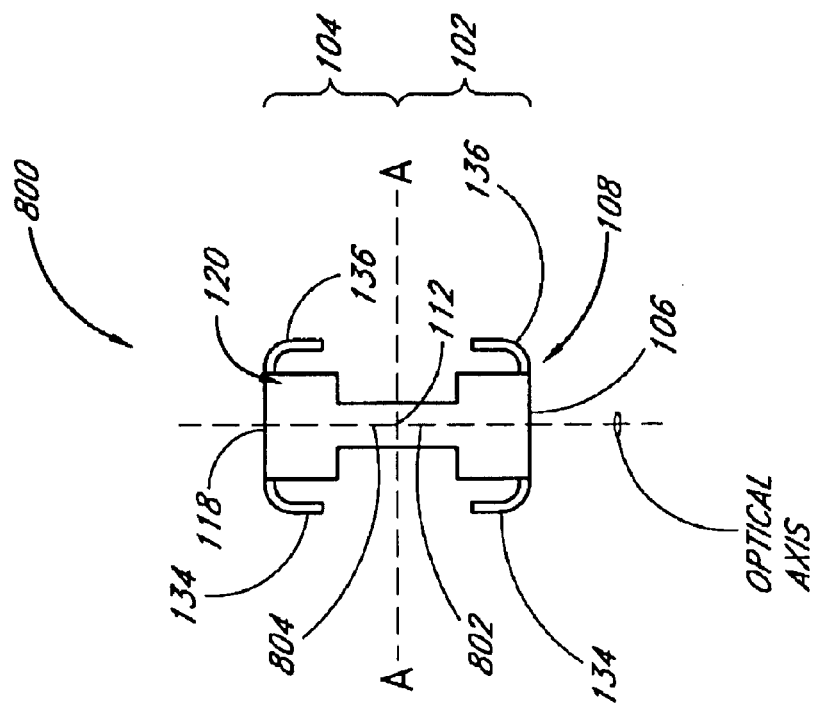
FIG. 38 is a top view of another embodiment of the lens system.
Figure 37:
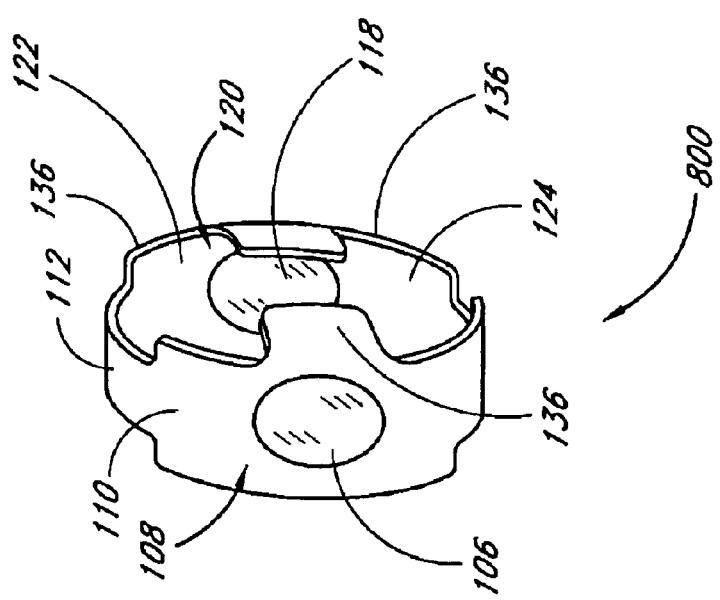
FIG. 37 is a perspective view of another embodiment of the lens system.

FIGS. 37 and 38 show a further embodiment 800 of the lens system, in which the anterior and posterior biasing elements 108, 120 comprise integral "band" like members forming, respectively, the first and second anterior translation members 110, 114 and the first and second posterior translation members 122, 124. The biasing elements 108, 120 also form reduced-width portions 802, 804 which meet at the apices of the lens system 800 and provide regions of high flexibility to facilitate sufficient accommodative movement. The depicted distending portion 132 includes three pairs of distending members 134, 136 which have a curved configuration but nonetheless project generally away from the optical axis.

FIGS. 38.1 and 38.2 depict another embodiment 900 of the lens system, as implanted in the capsular bag 58. The embodiment shown in FIGS. 38.1 and 38.2 may be similar to any of the embodiments described above, except that the biasing elements 108, 120 are dimensioned so that the apices 112, 116 abut the zonules 62 and ciliary muscles 60 when in the unaccommodated state as seen in FIG. 38.1. In addition, the lens system 900 is configured such that it will remain in the unaccommodated state in the absence of external forces. Thus, when the ciliary muscles 60 contract, the muscles 60 push the apices 112, 116 closer together, causing the biasing elements 108, 120 to bow out and the viewing elements 106, 118 to separate and attain the accommodated state as shown in FIG. 38.2. When the ciliary muscles 60 relax and reduce/eliminate the force applied to the apices 112, 116 the biasing elements 108, 120 move the lens system 900 to the unaccommodated state depicted in FIG. 38.1.

FIGS. 38.3 and 38.4 depict biasers 1000 which may be used bias the lens system 100 toward the accommodated or unaccommodated state, depending on the desired operating characteristics of the lens system. It is therefore contemplated that the biasers 1000 may be used with any of the embodiments of the lens system 100 disclosed herein. The bias provided by the biasers 1000 may be employed instead of, or in addition to, any bias generated by the biasing elements 108, 120. In one embodiment (see FIG. 38.3), the biasers 1000 may comprise U-shaped spring members having apices 1002 located adjacent the apices 112, 116 of the lens system 100. In another embodiment (see FIG. 38.4), the biasers 1000 may comprise any suitable longitudinal-compression springs which span the apices 112, 116 and interconnect the anterior and posterior biasing elements 108, 120. By appropriately selecting the spring constants and dimensions of the biasers 1000 (in the case of U-shaped springs, the apex angle and arm length; in the case of longitudinal-compression springs, their overall length), the biasers 1000 can impart to the lens system 100 a bias toward the accommodated or unaccommodated state as desired.

The biasers 1000 may be formed from any of the materials disclosed herein as suitable for constructing the lens system 100 itself. The material(s) selected for the biasers 1000 may be the same as, or different from, the material(s) which are used to form the remainder of the particular lens system 100 to which the biasers 1000 are connected. The number of biasers 1000 used in a particular lens system 100 may be equal to or less than the number of apices formed by the biasing elements of the lens system 100.

IX. IMPLANTATION METHODS

Various techniques may be employed in implanting the various embodiments of the lens system in the eye of a patient. The physician can first access the anterior aspect of the capsular bag 58 via any appropriate technique. Next, the physician incises the anterior of the bag; this may involve making the circular opening 66 shown in FIGS. 21 and 22, or the physician may make a "dumbbell" shaped incision by forming two small circular incisions or openings and connecting them with a third, straight-line incision. The natural lens is then removed from the capsular bag via any of various known techniques, such as phacoemulsification, cryogenic and/or radiative methods. To inhibit further cell growth, it is desirable to remove or kill all remaining epithelial cells. This can be achieved via cryogenic and/or radiative techniques, antimetabolites, chemical and osmotic agents. It is also possible to administer agents such as P15 to limit cell growth by sequestering the cells.

In the next step, the physician implants the lens system into the capsular bag. Where the lens system comprises separate anterior and posterior portions, the physician first folds or rolls the posterior portion and places it in the capsular bag through the anterior opening. After allowing the posterior portion to unroll/unfold, the physician adjusts the positioning of the posterior portion until it is within satisfactory limits. Next the physician rolls/folds and implants the anterior portion in a similar manner, and aligns and assembles the anterior portion to the posterior portion as needed, by causing engagement of mating portions, etc. formed on the anterior and posterior portions.

Where the lens system comprises anterior and posterior portions which are partially assembled or partially integral (see discussion above in the section titled MULTIPLE-PIECE AND OTHER EMBODIMENTS), the physician employs appropriate implantation procedures, subsequently folding/rolling and inserting those portions of the lens system that are separately foldable/rollable. In one embodiment, the physician first rolls/folds one portion of the partially assembled lens system and then inserts that portion. The physician then rolls/folds another portion of the partially assembled lens system and the inserts that portion. This is repeated until the entire system is inside the capsular bag, whereupon the physician completes the assembly of the portions and aligns the lens system as needed. In another embodiment, the physician first rolls/folds all of the separately rollable/foldable portions of the partially assembled lens system and then inserts the rolled/folded system into the capsular bag. Once the lens system is in the capsular bag, the physician completes the assembly of the portions and aligns the lens system as needed.

Figure 39A:
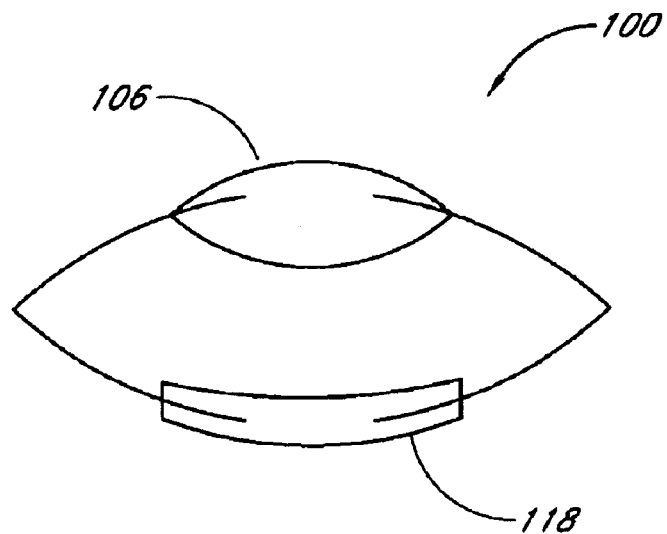
FIG. 39 is a series of schematic views of an insertion technique for use in connection with the lens system

It is contemplated that conventional intraocular lens folding devices, injectors, syringes and/or shooters can be used to insert any of the lens systems disclosed herein. A preferred folding/rolling technique is depicted in FIG. 39, where the lens system 100 is shown first in its normal condition (A). The anterior and posterior viewing elements 106, 118 are manipulated to place the lens system 100 in a low-profile condition (B), in which the viewing elements 106, 118 are out of axial alignment and are preferably situated so that no portion of the anterior viewing element 106 overlaps any portion of the posterior viewing element 118, as viewed along the optical axis. In the low-profile position (B), the thickness of the lens system 100 is minimized because the viewing elements 106, 118 are not "stacked" on top of each other, but instead have a side-by-side configuration. From the low-profile condition (B) the viewing elements 106, 118 and/or other portions of the lens system 100 can be folded or rolled generally about the transverse axis, or an axis parallel thereto. Alternatively, the lens system could be folded or rolled about the lateral axis or an axis parallel thereto. Upon folding/rolling, the lens system 100 is placed in a standard insertion tool as discussed above and is inserted into the eye.

When the lens system 100 is in the low-profile condition (B), the system may be temporarily held in that condition by the use of dissolvable sutures, or a simple clip which is detachable or manufactured from a dissolvable material. The sutures or clip hold the lens system in the low-profile condition during insertion and for a desired time after insertion. By temporarily holding the lens system in the low-profile condition after insertion, the sutures or clip provide time for fibrin formation on the edges of the lens system which, after the lens system departs from the low-profile condition, may advantageously bind the lens system to the inner surface of the capsular bag.

The physician next performs any adjustment steps which are facilitated by the particular lens system being implanted. Where the lens system is configured to receive the optic(s) in "open" frame members, the physician first observes/measures/determines the post-implantation shape taken on by the capsular bag and lens system in the accommodated and/or unaccommodated states and select(s) the optics which will provide the proper lens-system performance in light of the observed shape characteristics and/or available information on the patient's optical disorder. The physician then installs the optic(s) in the respective frame member(s); the installation takes place either in the capsular bag itself or upon temporary removal of the needed portion(s) of the lens system from the bag. If any portion is removed, a final installation and assembly is then performed with the optic(s) in place in the frame member(s).

Where the optic(s) is/are formed from an appropriate photosensitive silicone as discussed above, the physician illuminates the optic(s) (either anterior or posterior or both) with an energy source such as a laser until they attain the needed physical dimensions or refractive index. The physician may perform an intervening step of observing/measuring/determining the post-implantation shape taken on by the capsular bag and lens system in the accommodated and/or unaccommodated states, before determining any needed changes in the physical dimensions or refractive index of the optic(s) in question.

Figure 40:
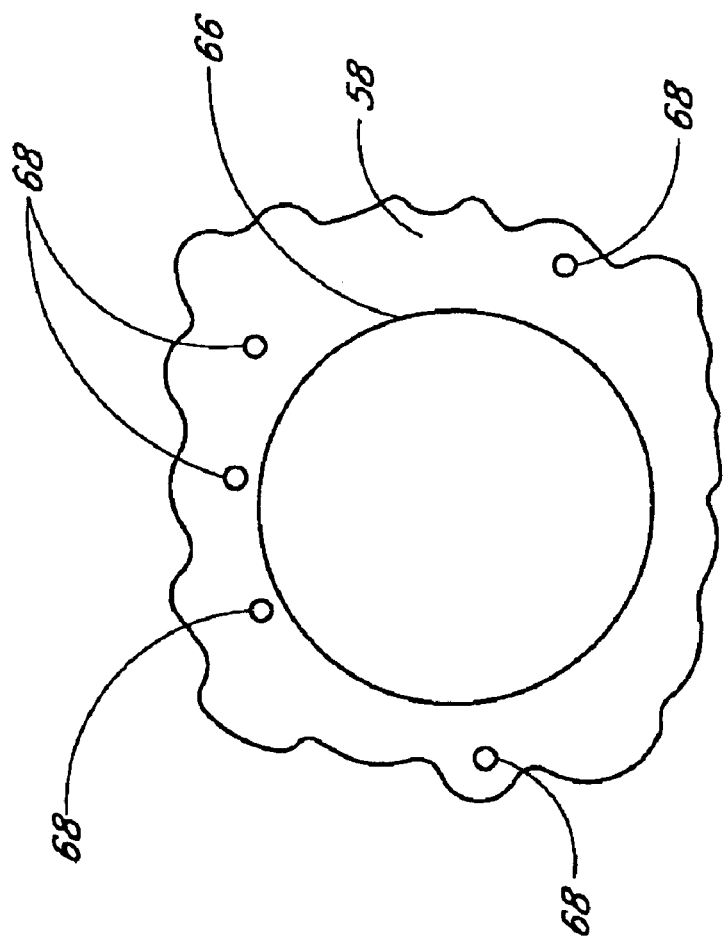
FIG. 40 is a schematic view of fluid-flow openings formed in the anterior aspect of the capsular bag.
Figure 18:
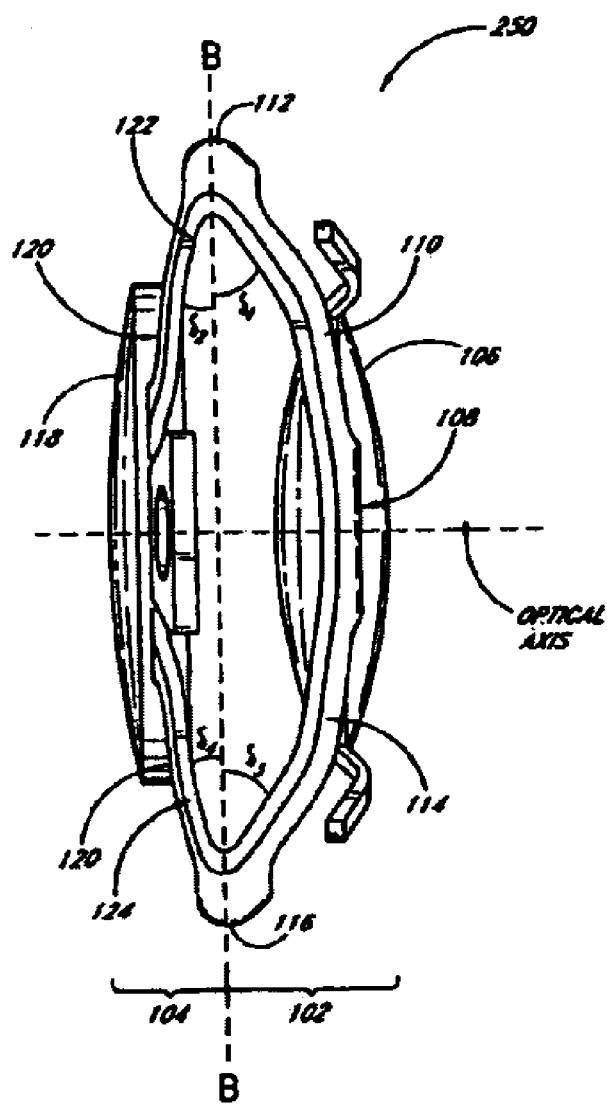

FIG. 40 depicts a technique which may be employed during lens implantation to create a fluid flow path between the interior of the capsular bag 58 and the region of the eye anterior of the capsular bag 58. The physician forms a number of fluid-flow openings 68 in the anterior aspect of the capsular bag 58, at any desired location around the anterior opening 66. The fluid-flow openings 68 ensure that the desired flow path exists, even if a seal is created between the anterior opening 66 and a viewing element of the lens system.

Where an accommodating lens system is implanted, the openings 68 create a fluid flow path from the region between the viewing elements of the implanted lens system, and the region of the eye anterior of the capsular bag 58. However, the technique is equally useful for use with conventional (non-accommodating) intraocular lenses.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. An accommodating intraocular lens for implantation in an eye having an optical axis, said lens comprising:
   an anterior portion comprising:
      an anterior viewing element having a periphery and comprised of an optic having refractive power;
      an anterior biasing element comprising first and second anterior translation members extending from the anterior viewing element; and
   a posterior portion comprising:
      a posterior viewing element having a periphery, said posterior viewing element in spaced relationship to said anterior viewing element;
      a posterior biasing element comprising first and second posterior translation members extending from the posterior viewing element;
   said first anterior translation member and said first posterior translation member meeting at a first apex of said intraocular lens, and said second anterior translation member and said second posterior translation member meeting at a second apex of the intraocular lens, such that force on said anterior portion and said posterior portion causes the separation between said viewing elements to change;
   said anterior and posterior biasing elements being spring-like and biasing said viewing elements apart such that, in the absence of external forces, said anterior and posterior viewing elements are at maximum separation;
   wherein said first anterior translation member is attached to said anterior viewing element at first and second spaced attachment locations, each of the first and second attachment locations being significantly further away from the first apex than the periphery of the anterior viewing element is from the first apex.

2. The lens of claim 1, wherein said first and second anterior translation members extend from respective sides of said anterior viewing element.

3. The lens of claim 2, wherein said first and second posterior translation members extend from respective sides of said posterior viewing element.

4. The lens of claim 1, wherein said first and second anterior translation members extend from respective opposite sides of said anterior viewing element.

5. The lens of claim 4, wherein said first and second posterior translation members extend from respective opposite sides of said posterior viewing element.

6. The lens of claim 1, wherein at least one of said first and second anterior translation members comprises a left arm and a right arm connected to said anterior viewing element at corresponding attachment locations.

7. The lens of claim 1, wherein said first anterior translation member comprises a left arm and a right arm connected to said anterior viewing element at corresponding attachment locations, said attachment locations of said left and right arms of said first anterior translation member being located equidistant from said first apex.

8. The lens of claim 7, wherein said second anterior translation member comprises a left arm and a right arm connected to said anterior viewing element at corresponding attachment locations, said attachment locations of said, left and right arms of said second anterior translation member being located equidistant from said second apex.

9. The lens of claim 8, wherein said attachment location of said left arm of said first anterior translation member is spaced from said attachment location of said left arm of said second anterior translation member about the periphery of said anterior viewing element.

10. The lens of claim 9, wherein said attachment location of said right arm of said first anterior translation member is spaced from said attachment location of said right arm of said second anterior translation member about the periphery of said anterior viewing element.

11. The lens of claim 8, wherein:
   said lens includes an optical axis which is adapted to be substantially coincident with the optical axis of the eye upon implantation of said lens; and
   said first and second apices are situated equidistant from said optical axis of said lens and are arranged 180 degrees apart from each other about said optical axis of said lens.

12. The lens of claim 1, wherein at least a portion of at least one of said first and second anterior translation members has an outer surface which is substantially flat.

13. The lens of claim 1, wherein at least a portion of at least one of said first and second anterior translation members has an outer surface which is generally convex.

14. The lens of claim 1, wherein at least a portion of at least one of said first and second posterior translation members has an outer surface which is substantially flat.

15. The lens of claim 1, wherein at least a portion of at least one of said first and second posterior translation members has an outer surface which is generally convex.

16. The lens of claim 1, wherein:
   said viewing elements having a range of motion that includes an accommodated and an unaccommodated position; and
   said lens further comprises first and second biasers located near said first and second apices, respectively, and configured to bias said viewing elements toward one of said accommodated position and said unaccommodated position.

17. The lens of claim 16, wherein at least one of the biasers is a U-shaped spring member located adjacent to one of said apices.

18. The lens of claim 1, wherein said second anterior translation member is attached to said anterior viewing element at third and fourth spaced attachment locations, each of the third and fourth attachment locations being significantly further away from the second apex than the periphery of the anterior viewing element is from the second apex.

19. The lens of claim 18, wherein said first posterior translation member is attached to said posterior viewing element at fifth and sixth spaced attachment locations, each of the fifth and sixth attachment locations being significantly further away from the first apex than the periphery of the posterior viewing element is from the first apex.

20. The lens of claim 19, wherein said second posterior translation member is attached to said posterior viewing element at seventh and eighth spaced attachment locations, each of the seventh and eighth attachment locations being significantly further away from the second apex than the periphery of the posterior viewing element is from the second apex.

21. The lens of claim 1, wherein at least one of said first anterior translation member, said second anterior translation member, said first posterior translation member and said second posterior translation member comprises a left arm and a right arm, both of said arms connected to the same one of said anterior viewing element and said posterior viewing element at corresponding attachment locations.

22. The lens of claim 1, wherein said first anterior translation member is attached to said anterior viewing element by virtue of said first anterior translation member and said anterior viewing element being formed from the same piece of material.

23. An accommodating intraocular lens for implantation in an eye having an optical axis, said lens comprising:
   an anterior portion comprising:
      an anterior viewing element having a periphery and comprised of an optic having refractive power;
      an anterior biasing element comprising first and second anterior translation members extending from the anterior viewing element;
   a posterior portion comprising:
      a posterior viewing element having a periphery, said posterior viewing element in spaced relationship to said anterior viewing element;
      a posterior biasing element comprising first and second posterior translation members extending from the posterior viewing element;
   said first anterior translation member and said first posterior translation member meeting at a first apex of said intraocular lens, and said second anterior translation member and said second posterior translation member meeting at a second apex of the intraocular lens, such that force on said anterior portion and said posterior portion causes the separation between said viewing elements to change;
   wherein said first anterior translation member is attached to said anterior viewing element at first and second spaced attachment locations, each of the first and second attachment locations being significantly further away from the first apex than the periphery of the anterior viewing element is from the first apex;
   a first anterior abutment connected to said first anterior translation member remote from said anterior viewing element;
   a second anterior abutment connected to said second anterior translation member remote from said anterior viewing element;
   a first posterior abutment connected to said first posterior translation member remote from said anterior viewing element;
   a second posterior abutment connected to said second posterior translation member remote from said posterior viewing element;
   wherein said first anterior abutment and said first posterior abutment are in abutting relation and said second anterior abutment and said second posterior abutment are in abutting relation.

24. The lens of claim 23, wherein:
   said first anterior abutment further comprises first anterior engagement members;
   said first posterior abutment further comprises first posterior engagement members;
   wherein the first anterior engagement members and the first posterior engagement members match so as to the facilitate alignment and assembly of said first anterior abutment and said first posterior abutment.

25. The lens of claim 23, wherein said first anterior abutment and said first posterior abutment are hingedly connected.

26. The lens of claim 23, wherein said anterior abutments and said posterior abutments are curled.

27. The lens of claim 23, wherein said first anterior translation member is attached to said anterior viewing element by virtue of said first anterior translation member and said anterior viewing element being formed from the same piece of material.

28. An accommodating intraocular lens for implantation in an eye having an optical axis, said lens comprising:

an anterior portion comprising:
- an anterior viewing element having a periphery and comprised of an optic having refractive power;
- an anterior biasing element comprising first and second anterior translation members extending from the anterior viewing element; and a posterior portion comprising:
- a posterior viewing element having a periphery, said posterior viewing element in spaced relationship to said anterior viewing element;
- a posterior biasing element comprising first and second posterior translation members extending from the posterior viewing element;

said first anterior translation member and said first posterior translation member meeting at a first apex of said intraocular lens, and said second anterior translation member and said second posterior translation member meeting at a second apex of the intraocular lens, such that force on said anterior portion and said posterior portion causes the separation between said viewing elements to change;

wherein said first anterior translation member is attached to said anterior viewing element at first and second spaced attachment locations, each of the first and second attachment locations being significantly further away from the first apex than the periphery of the anterior viewing element is from the first apex;

wherein said viewing elements having a range of motion that includes an accommodated and an unaccommodated position;

wherein said lens further comprises first and second biasers located near said first and second apices, respectively, and configured to bias said viewing elements toward one of said accommodated position and said unaccommodated position, wherein at least one of the biasers is a longitudinal-compression spring spanning one of said apices and interconnecting the anterior biasing element and the posterior biasing element.

29. The lens of claim 28, wherein said first anterior translation member is attached to said anterior viewing element by virtue of said first anterior translation member and said anterior viewing element being formed from the same piece of material.

30. An accommodating intraocular lens for implantation in an eye having an optical axis, said lens comprising:

an anterior portion comprising:
- an anterior viewing element having a periphery and comprised of an optic having refractive power;
- an anterior biasing element comprising first and second anterior translation members extending from the anterior viewing element; and a posterior portion comprising:
- a posterior viewing element having a periphery, said posterior viewing element in spaced relationship to said anterior viewing element;
- a posterior biasing element comprising first and second posterior translation members extending from the posterior viewing element;

said first anterior translation member and said first posterior translation member meeting at a first apex of said intraocular lens, and said second anterior translation member and said second posterior translation member meeting at a second apex of the intraocular lens, such that force on said anterior portion and said posterior portion causes the separation between said viewing elements to change;

wherein said first and second anterior translation members are curved and the curvature of said first and second anterior translation members changes as the separation between said viewing elements changes;

wherein said first anterior translation member is attached to said anterior viewing element at first and second spaced attachment locations, each of the first and second attachment locations being significantly further away from the first apex than the periphery of the anterior viewing element is from the first apex.

31. The lens of claim 30, wherein at least one of said first and second anterior translation members comprises a left arm and a right arm connected to said anterior viewing element at corresponding attachment locations.

32. The lens of claim 30, wherein said first anterior translation member comprises a left arm and a right arm connected to said anterior viewing element at corresponding attachment locations, said attachment locations of said left and right arms of said first anterior translation member being located equidistant from said first apex.

33. The lens of claim 32, wherein said second anterior translation member comprises a left arm and a right arm connected to said anterior viewing element at corresponding attachment locations, said attachment locations of said left and right arms of said second anterior translation member being located equidistant from said second apex.

34. The lens of claim 33, wherein said attachment location of said left arm of said first anterior translation member is spaced from said attachment location of said left arm of said second anterior translation member about the periphery of said anterior viewing element.

35. The lens of claim 34, wherein said attachment location of said right arm of said first anterior translation member is spaced from said attachment location of said right arm of said second anterior translation member about the periphery of said anterior viewing element.

36. The lens of claim 32, wherein:
- said lens includes an optical axis which is adapted to be substantially coincident with the optical axis of the eye upon implantation of said lens; and
- said first and second apices are situated equidistant from said optical axis of said lens and are arranged 180 degrees apart from each other about said optical axis of said lens.

37. The lens of claim 30, wherein at least a portion of at least one of said first and second anterior translation members has an outer surface which is substantially flat.

38. The lens of claim 30, wherein at least a portion of at least one of said first and second anterior translation members has an outer surface which is generally convex.

39. The lens of claim 30, wherein at least a portion of at least one of said first and second posterior translation members has an outer surface which is substantially flat.

40. The lens of claim 30, wherein at least a portion of at least one of said first and second posterior translation members has an outer surface which is generally convex.

41. The lens claim 30, further comprising:
- a first anterior abutment connected to said first anterior translation member remote from said anterior viewing element;
- a second anterior abutment connected to said second anterior translation member remote from said anterior viewing element;
- a first posterior abutment connected to said first posterior translation member remote from said anterior viewing element;

a second posterior abutment connected to said second posterior translation member remote from said posterior viewing element;

wherein said first anterior abutment and said first posterior abutment are in abutting relation and said second anterior abutment and said second posterior abutment are in abutting relation.

42. The lens claim 41, wherein:

said first anterior abutment further comprises first anterior engagement members;

said first posterior abutment further comprises first posterior engagement members; and the first anterior engagement members and the first posterior engagement members match so as to the facilitate alignment and assembly of said first anterior abutment and said first posterior abutment.

43. The lens of claim 41, wherein said first anterior abutment and said first posterior abutment are hingedly connected.

44. The lens of claim 41, wherein said anterior abutments and said posterior abutments are curled.

45. The lens of claim 30, whrein said second anterior translation member is attached to said anterior viewing element at third and fourth spaced attachment locations, each of the third and fourth attachment locations being significantly further away from the second apex than the periphery of the anterior viewing element is from the second apex.

46. The lens of claim 45, wherein said first posterior translation member is attached to said posterior viewing element at fifth and sixth spaced attachment locations, each of the fifth and sixth attachment locations being significantly further away from the first apex than the periphery of the posterior viewing element is from the first apex.

47. The lens of claim 46, wherein said second posterior translation member is attached to said posterior viewing element at seventh and eighth spaced attachment locations, each of the seventh and eighth attachment locations being significantly further away from the second apex than the periphery of the posterior viewing element is from the second apex.

48. The lens of claim 30, wherein at least one of said first anterior translation member, said second anterior translation member, said first posterior translation member and said second posterior translation member comprises a left arm and a right arm, both of said arms connected to the same one of said anterior viewing element and said posterior viewing element at corresponding attachment locations.

49. The lens of claim 30, wherein said first anterior translation member is attached to said anterior viewing element by virtue of said first anterior translation member and said anterior viewing element being formed from the same piece of material.

* * * * *

UNITED STATES PATENT AND TRADEMARK OFFICE
CERTIFICATE OF CORRECTION

PATENT NO.   : 6,761,737 B2
DATED        : July 13, 2004
INVENTOR(S)  : Gholam-Reza Zadno-Azizi et al.

It is certified that error appears in the above-identified patent and that said Letters Patent is hereby corrected as shown below:

Column 28,
Line 55, after "said" delete ",".

Column 32,
Line 58, after "lens" insert -- of --.

Column 33,
Line 8, after "lens" insert -- of --.
Line 23, delete "whrein" and insert -- wherein --, therefor.

Signed and Sealed this

Sixth Day of September, 2005

JON W. DUDAS
*Director of the United States Patent and Trademark Office*

UNITED STATES PATENT AND TRADEMARK OFFICE
CERTIFICATE OF CORRECTION

PATENT NO. : 6,761,737 B2
DATED : July 13, 2004
INVENTOR(S) : Gholam Zadno-Azizi et al.

Figure 39B:
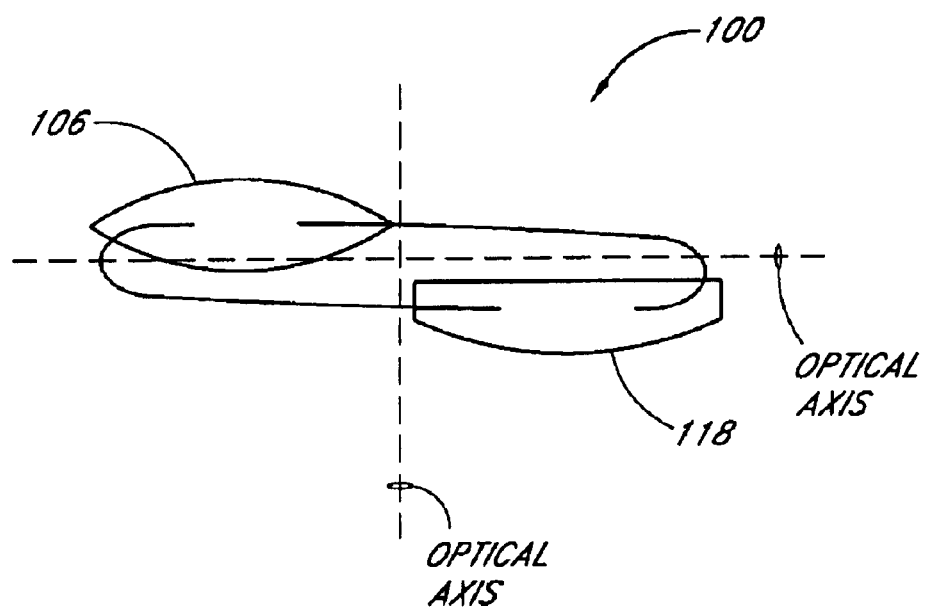
Figure 39B:
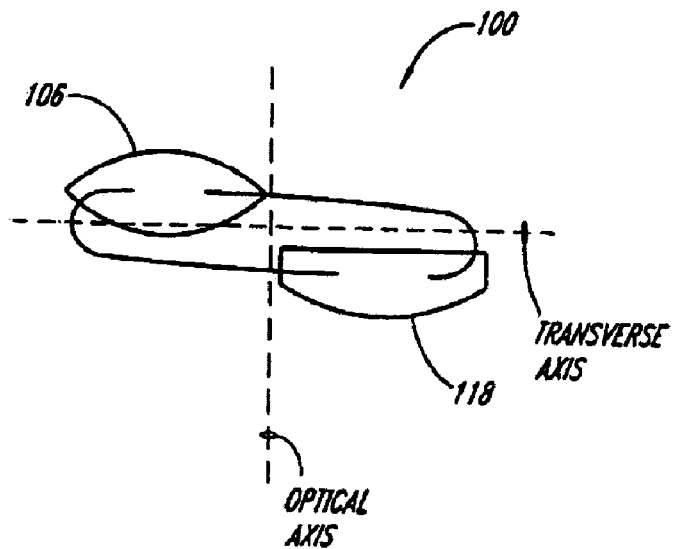

It is certified that error appears in the above-identified patent and that said Letters Patent is hereby corrected as shown below:

Drawings,
Replace Figure 18 and Figure 39B with the attached sheets.

Column 16,
Line 11, delete "substantially equal" and substitute -- unequal --.

Signed and Sealed this

Thirteenth Day of June, 2006

JON W. DUDAS
*Director of the United States Patent and Trademark Office*